(12) United States Patent
Pfahl et al.

(10) Patent No.: US 7,196,108 B2
(45) Date of Patent: *Mar. 27, 2007

(54) BICYCLIC HETEROCYCLES FOR THE TREATMENT OF DIABETES AND OTHER DISEASES

(75) Inventors: Magnus Pfahl, Solana Beach, CA (US); Catherine Tachdjian, San Diego, CA (US); Hussien A. Al-Shamma, Encinitas, CA (US); Andrea Fanjul Giachino, San Diego, CA (US); Karine Jakubowicz-Jaillardon, Villebon sur Yvette (FR); Jianhua Guo, San Diego, CA (US); Richard M. Fine, Ridgewood, NJ (US); Lyle W. Spruce, Chula Vista, CA (US); James W. Zapf, San Diego, CA (US)

(73) Assignees: Incyte San Diego Inc., Wilmington, DE (US); Ortho McNeil Pharmaceutical Inc., Rariton, NJ (US)

( * ) Notice: Subject to any disclaimer, the term of this patent is extended or adjusted under 35 U.S.C. 154(b) by 277 days.

This patent is subject to a terminal disclaimer.

(21) Appl. No.: 10/384,391

(22) Filed: Mar. 6, 2003

(65) Prior Publication Data
US 2004/0034004 A1 Feb. 19, 2004

Related U.S. Application Data

(60) Provisional application No. 60/362,732, filed on Mar. 8, 2002.

(51) Int. Cl.
| | |
|---|---|
| A61K 31/343 | (2006.01) |
| A61K 31/381 | (2006.01) |
| A61K 31/382 | (2006.01) |
| A61K 31/403 | (2006.01) |
| A61K 31/4166 | (2006.01) |
| A61K 31/427 | (2006.01) |
| A61K 31/4353 | (2006.01) |
| A61K 31/538 | (2006.01) |
| A61K 31/5415 | (2006.01) |
| C07D 277/34 | (2006.01) |
| C07D 265/36 | (2006.01) |
| C07D 243/10 | (2006.01) |
| C07D 241/36 | (2006.01) |
| C07D 233/72 | (2006.01) |
| C07D 223/14 | (2006.01) |
| C07D 221/02 | (2006.01) |
| C07D 209/04 | (2006.01) |
| C07D 335/04 | (2006.01) |
| C07D 333/50 | (2006.01) |
| C07D 319/14 | (2006.01) |
| C07D 311/04 | (2006.01) |
| C07D 307/77 | (2006.01) |

(52) U.S. Cl. ............... 514/366; 540/544; 540/553; 540/582; 544/2; 544/63; 544/89; 546/112; 546/113; 548/200; 548/311.1; 548/452; 549/32; 549/377; 549/396; 549/462; 514/211.05; 514/212.07; 514/230.5; 514/252.1; 514/300; 514/366; 514/387; 514/412; 514/453

(58) Field of Classification Search ............... 548/183, 548/200, 311.1, 452; 514/369, 211.05, 212.07, 514/230.5, 252.1, 366, 300, 387, 412, 453; 546/112, 113; 544/2, 63, 89; 540/544, 553, 540/582; 549/32, 377, 396, 462
See application file for complete search history.

(56) References Cited

U.S. PATENT DOCUMENTS

| | | | |
|---|---|---|---|
| 4,051,842 A | 10/1977 | Hazel et al. | |
| 4,140,122 A | 2/1979 | Kühl et al. | |
| 4,383,529 A | 5/1983 | Webster | |
| 4,668,506 A | 5/1987 | Bawa | |

(Continued)

FOREIGN PATENT DOCUMENTS

EP 0 212 617 3/1987

(Continued)

OTHER PUBLICATIONS

Barclay et al., "ortho-Diquaternary aromatic compounds. III. Synthesis and reactions of polyalkyltetralones and derivatives," *Canadian Journal of Chemistry*, 48(17):2763-2775 (1970).

(Continued)

*Primary Examiner*—Kamal A. Saeed
*Assistant Examiner*—Janet Coppins
(74) *Attorney, Agent, or Firm*—Needle & Rosenberg, P.C.

(57) ABSTRACT

The invention relates to certain bicyclic heterocycles havng the structure shown below which are useful in the treatment of diseases related to lipid and carbohydrate metabolism, such as type 2 diabetes, and atherosclerosis.

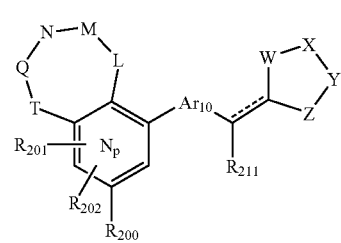

(300)

61 Claims, 8 Drawing Sheets

U.S. PATENT DOCUMENTS

| | | | |
|---|---|---|---|
| 4,713,244 | A | 12/1987 | Bawa et al. |
| 4,788,063 | A | 11/1988 | Fisher et al. |
| 4,931,279 | A | 6/1990 | Bawa et al. |
| 4,971,996 | A | 11/1990 | Shiraishi et al. |
| 5,223,522 | A | 6/1993 | Clark et al. |
| 5,330,998 | A | 7/1994 | Clark et al. |
| 5,512,689 | A | 4/1996 | Quallich |
| 5,523,314 | A | 6/1996 | Bue-Valleskey et al. |
| 5,650,444 | A | 7/1997 | Cagiano et al. |
| 5,691,376 | A | 11/1997 | Cagiano et al. |
| 5,780,676 | A | 7/1998 | Boehm et al. |
| 6,127,415 | A | 10/2000 | Pfahl et al. |
| 6,262,044 | B1 | 7/2001 | Møller et al. |
| 6,515,003 | B1* | 2/2003 | Pfahl et al. .............. 514/369 |
| 6,765,013 | B2 | 7/2004 | Pfahl et al. |
| 6,927,228 | B2 | 8/2005 | Bernardon et al. |
| 2002/0143182 | A1 | 10/2002 | Pfahl et al. |
| 2003/0083357 | A1 | 5/2003 | Pfahl et al. |
| 2003/0105333 | A1 | 6/2003 | Pfahl et al. |
| 2003/0144329 | A1 | 7/2003 | Pfahl et al. |
| 2003/0153606 | A1 | 8/2003 | Pfahl et al. |
| 2003/0216432 | A1 | 11/2003 | Pfahl et al. |
| 2004/0034004 | A1 | 2/2004 | Pfahl et al. |
| 2004/0097566 | A1 | 5/2004 | Pfahl et al. |
| 2005/0014767 | A1 | 1/2005 | Pfahl et al. |
| 2005/0038098 | A1 | 2/2005 | Tachdjian et al. |
| 2005/0070581 | A1 | 3/2005 | Pfahl et al. |

FOREIGN PATENT DOCUMENTS

| | | |
|---|---|---|
| EP | 0 304 493 | 3/1989 |
| EP | 0 343 643 | 11/1989 |
| EP | 1 048 659 | 11/2000 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | WO 97/03682 | 2/1997 |
| WO | WO 97/27191 | 7/1997 |
| WO | WO 99/09965 | 3/1999 |
| WO | WO 99/58127 | 11/1999 |
| WO | WO 00/10573 | 3/2000 |
| WO | WO 00/18748 | 4/2000 |
| WO | WO 00/32598 | 6/2000 |
| WO | WO 00/63196 | 10/2000 |
| WO | WO 00/066167 | 11/2000 |
| WO | WO 01/16122 | 3/2001 |
| WO | WO 01/16123 | 3/2001 |
| WO | WO 01/36402 | 5/2001 |
| WO | WO 02/12210 | 2/2002 |
| WO | WO 02/071827 | 9/2002 |
| WO | WO 02/072009 | 9/2002 |
| WO | WO 02/072543 | 9/2002 |
| WO | WO 02/080935 A1 | 10/2002 |

OTHER PUBLICATIONS

Cacchi et al., "Palladium-Catalyzed Triethylammonium Formate Reduction of Aryl Triflates. A Selective Method for the deoxygenation of phenols," *Tetrahedron Letters*, 27(45):5541-5544 (1986).

Faul et al., "Synthesis of Novel Retinoid X Receptor-Selective Retinoids," *J. Org. Chem.*, 66:5772-5782 (2001).

Iwatsuka et al., "General Survey of Diabetic Features of Yellow KK Mice," *Endocrinol. Japon.* 17:23-35 (1970).

Xiong et al., "Human D-Type Cyclin," *Cell*, 65:691-699 (1991).

Alley et al., "Feasibility of Drug Screening with Panels of Human Tumor Cell Lines Using a Microculture Tetrazolium Assay," *Cancer Re.*, 48:589-601 (1988).

Amin et al., "Nitric Oxide Synthase and Cyclooxygenases: Distribution, Regulation, and Intervention in Arthritis," *Nitric pin. Rheumatol*, 11(3):202-209 (1999).

Aranyos et al., "Novel Electron-Rich Bulky Phospine Ligands Facilitate the Palladium-Catalyzed Preparation of Diaryl Ethers," *J. Am. Chem. Soc.*, 121:4369-4378 (1999).

Baraldi et al., "Exhaled Nitric Oxide Concentrations During Treatmnet of Wheezing Exacerbation in Infants and Young Children," *Am. J. Respir. Crit. Care Med.*, 159 (4 Pt. 1):1284-1288 (1999).

Beilstein Registry No. 29-30, 1975, Compound Registry No. 1120438.

Beilstein Registry No. 52, 1978, Compound Registry No. 4939128.

Black, "Simple Synthesis of 1-Azaadamantan-4-one," *Synthesis*, 829-830 (1981).

Blondet et al., "Convenient Synthesis of 6-Methyl, 8-Methyl and 6,8-Dimethyl Derivatives of 5-Hydroxy-1,2,3,4-Tetrahydro-2-Quinolinone," *Organic Preparation and Procedures Int.*, 25(2):223-228 (1993).

Bradisher et al., "Aromatic Cyclodehydration XXIV. Cyclization of Derivatives of (2-biphenylly)pyruvic Acid," *J. Org. Chem.*, 15(2) 374-376 (1950).

Bredt et al., "Isolation of Nitric Oxide Synthetase, a Calmodulin-Requiring Enzyme," *Proc. Natl. Acad. Sci.*, 87:682-685 (1990).

Brennan et al., "Inhibitory Effect of TNF Antibodies on Synovial Cell Interleukin-1 Prodcution in Rheumatoid Arthritis," *Lancet*, 2:244-247 (1989).

Cantello et al., "A Versatile Route to 2-Arylmethyl-1,2-oxadiazolidine-3,5-diones via Regiospecific Alkyl-ation of 1,2,4-Oxadiazolidine-3,5-dione," *Synlett*, 263-264 (1997).

Cantello et al., "The Synthesis of BRL 49653—A Novel and Potent Antihyperglycaemic Agent," *Bioorganic & Medicinal Chemistry Letters*, 4:1181-1184 (1994).

Chan et al., "New N- and O-Arylations with Phenyloboronic Acids and Curpric Acetate," *Tetrahedron Letters*, 39:2933-2936 (1998).

Chang et al., "The Upjohn Colony of Kka$^y$ Mice: A Model for Obese Type II Diabetes," *Elsevier Science Publishers B.V., Biomedical Division, Diabetes*, pp. 466-470 (1986).

Charpentier et al., "Synthesis, Structure—Affinity Relationships, and Biological Activities of Ligands Binding to Retinoic Acid Receptor Subtypes," *J. Med. Chem.*, 38:4993-5006 (1995).

Choi et al., "Similarity of Colorectal Cancer in Crohn's Disease and Ulcerative Colitis: Implications for Carcinogenesis and Prevention," *Gut*, 35:950-954 (1994).

Cobb et al., "N-(2-Benzoylphenyl)-L-tyrosine PPAR$_\gamma$ Agonists. 3. Structure-Activity Relationship and Optimization of the N-Aryl Substituent," *J. Med. Chem.*, 41:5055-5069 (1998).

Coleman "Diabetes-Obesity Syndromes in Mice," *Diabetes*, 31(1):1-6 (Apr. 1982).

Darses et al., "Palladium-Catalyzed Cross-Coupling Reactions of Arenediazonium Tetrafluoroborates with Aryl and Alkenylboronic Acids," *Bull. Soc. Chem. Fr.*, 133:1095-1102 (1996).

Dawson et al., "Conformational Effects on Retinoid Receptor Selectivity. 2. Effects of Retinoid Bridging Group on Retinoid X Receptor Activity and Selectivity," *J. Med. Chemistry*, 38:3368-3383 (1995).

Dawson et al., "The Synthetic Chemistry of Retinoids," *Biology, Chemistry, and Medicine*, 2$^{nd}$ Edition, Raven Press, Ltd., New York (1994).

Ebisawa et al., "Novel-Thiazolidinedione Derivatives with Retinoid Synergistic Activity," *Biol. Pharma. Bull.*, 21(5):547-549 (1998).

Evans et al., "Synthesis of Diaryl Ethers through the Copper-Promoted Arylation of Phenols with Arylboronic Acids. An Expedient Synthesis of Thyroxine," *Tetrahedron Letters*, 39:2937-2940 (1998).

Farahat et al., "Cytokine Expression in Synovial Membranes of Patients with Rheumatoid Arthritis and Osteoarthritis," *Ann. Rheum. Dis.*, 52: 870-875 (1993).

Ferrell, "Tripping the Switch Fantastic: How A Protein Kinase Cascade Can Convert Graded Inputs into Switch-Like Outputs," *TIBS*, 21:460-466 (1996).

Firooznia et al., "Enantioselective Synthesis of 4-Substituted Phenylalanines By Cross-Coupling Reactions," *Tetrahedron Letters*, 40:213-216 (1999).

Förstermann et al., "Induced RAW 264.7 Macrophages Express Soluble and Particulate Nitric Oxide Synthase: Inhibition By Transforming Growth Factor-," *Eur. J. Pharm.*, 225:161-165 (1992).

Fukuto et al., "Inhibition of Constitutive and Inducible Nitric Oxide Synthase: Potential Selective Inhibition," *Annu. Rev. Pharmacol. Toxicol.* 35:165-194 (1995).

Gahtan et al., "Inflammatory Pathogenesis in Alzheimer's Disease: Biological Mechanisms and Cognitive Sequeli," *Neurosci: Biobehav*, 23:615-633 (1999).

Glauser et al., "Pathogenesis and Potential Strategies for Prevention and Treatment of Septic Shock: An Update," *Clin. Infect Dis.* 18 (Suppl 2):S205-216 (1994).

Gown, et al., "Human Atherosclerosis—II. Immunocytochemical Analysis of the Cellular Composition of Human Atherosclerotic Lesions," *Am. J. Pathol.*, 125(1):191-207 (1986).

Gray et al., "Practical Methylation of Aryl Halides by Suzuki-Miyaura Coupling," *Tetrahedron Letters*, 41:6237-6240 (2000).

Haddach et al., "A New Method for the Synthesis of Ketones: The Palladium-Catalyzed Corss-Coupling of Acid Chlorides with Arylboronic Acids," *Tetrahedron Letters*, 40:3109-3112 (1999).

Harris et al., "Localization of a Pioglitazone Response Element in the Adipocyte Fatty Acid-Binding Protein Gene," *Mol. Pharmacol.*, 45:439-445 (1994).

Hudlicky, "Oxidations in Organic Chemistry," *ACS Monograph*, 186:114-127 (1990).

Hudlicky, "Oxidations in Organic Chemistry," *ACS Monograph*, 186:133-149 (1990).

Indolese, "Suzuki-Type Coupling of Chloroarenes with Arylboronic Acids Catalysed by Nickel Complexes," *Tetrahedron Letters*, 38:3513-3516 (1997).

Ishiyama et al., "Palladium(0)-Catalyzed Cross-Coupling Reaction of Alkoxydiboron with Haloarenes: A Direct Procedure for Arylboronic Esters," *J. Org. Chem.*, 60:7508-7510 (1995).

Ishiyama et al., "Palladium-Catalyzed Carbonylative Cross-Coupling Reaction of Arylboronic Acids with Aryl Electrophiles: Synthesis of Biaryl Ketones," *J. Org. Chem.*, 63:4726-4731 (1998).

Ishiyama et al. "Synthesis of Arylboronates via the Palladium(0)-Catalyzed Cross-Coupling Reaction of Tetra(alkoxo)diborons with Aryl Triflates," *Tetrahedron Letters*, 38:3447-3450 (1997).

Ishiyama et al. "Synthesis of Unsymmetrical Biaryl Ketones via Palladium-Catalyzed Carbonylative Cross-Coupling Reaction of Arylboronic Acids with Iodoarenes," *Tetrahedron Letters*, 34:7595-7598 (1993).

Jung et al., "New Efficient Method for the Total Synthesis of (S,S)-Isodityrosine from Natural Amino Acids," *J. Org. Chem.*, 64:2976-2977 (1999).

Kamidawa et al., "Palladium-Catalyzed Amination of Aryl Bromides Utilizing Arene-Chromium Complexes as Ligands," *J. Org. Chem.*, 63:8407-8410 (1998).

Kawai et al., "Enhancement of Rat Urinary Bladder Tumorigenesis by Lipopolysaccharide-induced inflammation," *Cancer Res.*, 53:5172-5175 (1993).

Kriegler et al., "A Novel Form of TNF/Cachectin is a Cell Surface Cytotoxic Transmembrane Protein: Ramifications for the Complex Physiology of TNF," *Cell*, 53:45-53 (1988).

Kyriakis et al., "Sounding the Alarm: Protein Kinase Cascades Activated by Stress and Inflammation," *J. Biol Chem.*, 271:24313-24316 (1996).

Littke et al., "A Convenient and General Method for Pd-Catalyzed Suzuki Cross-Couplings of Aryl Chlorides and Arylboronic Acids," *Angew. Chem. Int. Ed.*, 37:3387-3388 (1998).

Louie et al., "Palladium-Catalyzed Amination of Aryl Triflates and Importance of Triflate Addition Rate," *J. Org. Chem.*, 62:1268-1273 (1997).

Manickam et al., "New Parts for a Construction Set of Bifunctional Oligo(het)arylene Building Blocks for Modular Chemistry," *Synthesis*, 3:442-446 (2000).

McCann et al., "The Nitric Oxide Hypothesis of Aging," *Exp. Gerontol*, 33(7-8):813-826 (1998).

McCann, "The Nitric Oxide Hypothesis of Brain Aging," *Exp. Gerontol*, 32:431-440 (1997).

Miyaura et al., "Palladium-Catalyzed Cross-Coupling Reactions of Organoboron Compounds," *Chem. Rev.*, 95:2457-2483 (1995).

Molina et al., "The Role of Nitric Oxide in Neurodegeneration—Potential for Pharmacological Intervention," *Drugs & Aging*, 12(4):251-259 (1998).

Moroz et al., "The Ullmann Ether Condensation," *Russ. Chem. Rev.*, 43:679-689 (1974).

Oliff, "The Role of Tumor Necrosis Factor (Cachectin) in Cachexia," *Cell*, 54:141-142 (1988).

Oram, "Molecular Basic of Cholesterol Homeostasis: Lessons from Tangier Disease and ABCA1," *Trends in Molecular Medicines*, 8(4):168-173 (2002).

Paradisi, "Arene Substitution *via* Nucleophilic Addition to Electron Deficient Arenes," *Comprehensive Organic Synthesis*, 4:423-450 (1991).

Petrov et al., "The Arbuzov Rearrangement with Participation of Halogenoacetylenes as a Method of Synthesis of Ethynylphosphonates and other Organo-Phosphorus Compounds," *Russ. Chem. Rev.*, 52:1030-1035 (1983).

Pohlman et al., "An Endothelial Cell Surface Factor(s) Induced in Vitro By Lopopolysaccharide, Interleukin 1, and Tumor Necrosis Factor- Increases Neutrophil Adherence By A CDw18-Dependent Mechanism," *J. Immunol*, 136:4548-4553 (1986).

Pollock et al., "Purification and Characterization of Particulate Endothelium-derived Relaxing Factor Synthase from Cultured and Native Bovine Aortic Endothelial Cells," *Proc. Nat. Acad. Sci.*, 88:10480-10484 (1991).

Pujo-Borrell et al., "HLA Class II Induction In Human Islet Cells By Interferon- Plus Tumour-Necrosis Factor or Lymphotoxin," *Nature*, 326:304-306 (1987).

Rosin et al., "Inflammation, Chromosomal Instability, and Cancer: The Schistosomiasis Model" *Cancer Res.*, 54 (7 Suppl):1929s-1933s (1994).

Ross "Atherosclerosis—An Inflammatory Disease," *New England Journal of Medicine*, 340(2):115-126 (Jan. 1999).

Rust et al. "Tangier disease is caused by mutations in the gene encoding ATP-binding cassette transporter 1," *Nature Genetics*, 22:352-355 (Aug. 1999).

Sanders, "Asthma, Viruses, and Nitric Oxide," *Proc. Soc. Exp. Biol. Med.*, 220(3):123-132 (1999).

Schandendorf et al., "Retinoic Acid Receptor-γ Selective Retinoids Exert Antiproliferative Effects on Human Melanoma Cell Growth *Inv Vitro*," *International Journal of Oncology*, 5:1325-1331 (1994).

Serfaty-Lacrosniere et al., "Homozygous Tangier disease and cardiovascular disease," *Atherosclerosis*, 107:85-98 (1994).

Shao et al., "p53 Independent $G_0/G_1$ Arrest and Apoptosis Induced by a Novel Retinoid in Human Breast Cancer Cells," *Oncogene*, 11:493-504 (1995).

Smith et al., "The Active Form of Tumor Necrosis Factor Is A Trimer," *J. Biol. Chem.*, 262:6951-6954 (1987).

Sparrow et al., "A Potent Synthetic LXR Agonist is More Effective than Cholesterol Loading at Inducing ABCA1 mRNA and Stimulating Cholesterol Efflux," *Journal of Biological Chemsitry*, 277(12):10021-10027 (2002).

Spruce et al., "Heteroarotinoids. Synthesis, Characterization, and Biological Activity in Terms of an Assessment of these Systems to Inhibit the Induction of Ornithine Decarboxylase Activity and to Induce Terminal Differentiation of HL-60 Cells," *J. Med. Chem.*, 30:1474-1482 (1987).

Stanforth, "Catalytic Cross-Coupling Reactions in Biaryl Synthesis," *Tetrahedron*, 54:263-303 (1998).

Stirling et al., "Increase In Exhaled Nitric Oxide Levels in patients With Difficult Asthma and Correlation With Symptoms and Disease Severity Despite Treatment With Oral and Inhaled Corticosteroids," *Thorax*, 53(12):1030-1034 (1998).

Strieter et al., "Endothelial Cell Gene Expression of a Neutrophil Chemotactic Factor by TNF-, LPS, and IL-1," *Science*, 243:1467-1469 (1989).

Suzuki, "New Synthetic Transformations Via Organoboron Compounds," *Pure & Applied Chem.*, 66:213-222 (1994).

Teboul et al., "Thiazolidinediones and Fatty Acids Convert Myogenic Cells Into Adipose-like Cells," *J. Biol. Chem.*, 270:28183-28187 (1995).

Thompson et al., "Effect of carcinogen dose and age at administration on induction of mammary carcinogenesis by 1-methyl-1-nitrosourea," *Carginogenesis*, 13(9):1535-1539 (1992).

Thorns et al., "nNOS Expressing Neurons in the Entorhinal Cortex and Hippocampus Are Affected in Patients With Alzheimer's Disease," *Exp. Neurol.*, 150:14-20 (1998).

Tietze et al., "The Knoevenagel Reaction," *Comprehensive Organic Synthesis*, 2:341-394 (1991).

Tracey et al., "Anti-Cachectin/TNF Monoclonal Antibodies Prevent Septic Shock During Lethal Bacteraemia," *Nature*, 330:662-664 (1987).

Tracey et al., "Tumor Necrosis Factor: A Pleiotropic Cytokine and Therapuetic Target," *Ann. Rev. Med.*, 45:491-503 (1994).

Uysal et al., "Protection From Obesity-induced Insulin Resistance in Mice Lacking TNF- Function," *Nature*, 389:610-614 (1997).

Wadsworth, "Synthetic Applications of Phosphoryl-Stabilized Anions," *Organic Reactions*, 25:73-253 (1977).

Walter et al., "The High Density Lipoprotein—and Apolipoprotein A-1-Induced Mobilization of Cellular Cholesterol is Impaired in Fibroblasts from Tangier Disease Subjects," *Biochemical and Biophysical Research Communications*, 205(1):850-856 (1994).

Watanabe et al., "Synthesis of Sterically Hindered Biaryls via the Palladium-Catalyzed Cross-Coupling Reaction of Arylboronic Acids or Their Esters With Haloarenes," *Synlett.*, 207-210 (1992).

Weiberth et al., "Copper(I)-Activated Addition of Grignard Reagents to Nitriles. Synthesis of Ketimines, Ketones, and Amines," *J. Org. Chem.*, 52:3901-3904 (1987).

Willson et al., "The Structure-Activity Relationship Between Peroxisome Proliferator-Activated Receptor Agonism and the Antihyperglycemic Activity of Thiazolidinediones," *J. Med. Chem.*, 39:665-668 (1996).

Wolfe et al., "Scope and Limitations of the Pd/BINAP-Catalyzed Amination of Aryl Bromides," *J. Org. Chem.*, 65:1144-1157 (2000).

Wolfe et al., "Simple, Efficient Catalyst System for the Palladium-Catalyzed Amination of Aryl Chlorides, Bromides and Triflates," *J. Org. Chem.*, 65:1158-1174 (2000).

Yun et al., "Neurobiology of Nitric Oxide," *Crit. Rev. Neurobiol.*, 10:291-316 (1996).

Zask et al., "Synthesis of 3-Mercapto-2(5H)-Furanones via Reaction of Dilithio-2,4-thiazolidinedione With -Halo Ketones," *Tetrahedron Letters*, 34 (17):2719-2722 (1993).

Zask et al., "Synthesis and Antihyperglycemic Activity of Novel 5-(naphthalenylsufonyl)-2,4-thiazolidinediones," *J.Med.Chem.*, 33:1418-1423 (1990).

\* cited by examiner

Figure 6. Synthesis of Dihydrobenzopyrrole Precursors

Synthesis of Compounds of the Invention

BICYCLIC HETEROCYCLES FOR THE TREATMENT OF DIABETES AND OTHER DISEASES

RELATED APPLICATIONS

This application claims priority to the U.S. Provisional Application Serial No. 60/362,732, filed Mar. 8, 2002, the disclosure of which application is hereby incorporated in its entirety by this reference.

BACKGROUND OF THE INVENTION

Type 2 diabetes, also referred to as non-insulin dependent diabetes mellitus (NIDDM), afflicts between 80 and 90% of all diabetic patients in developed countries. In the United States alone, approximately 15 million people, and more than 100 million worldwide, are affected. Because this disorder is a late onset disease and occurs often in overweight persons it can be expected that the number of patients suffering from this disease will increase further. Patients suffering from type 2 diabetes usually still produce insulin but become increasingly resistant to their own insulin and to insulin therapy. A promising new class of drugs has been recently introduced that resensitizes patients to their own insulin (insulin sensitizers), thereby reducing the requirement for exogenous insulin. Troglitazone (Resulin™) and rosiglitazone (Avandia™) are among the first representatives of a class of drugs approved for the treatment of type 2 diabetes in the United States and several other countries. These drugs, however, have side effects including rare but severe liver toxicities (i.e., troglitazone) and they can increase body weight in humans. Such side effects are of major concern for patients who might require treatment for diabetes for a decade or longer. Therefore, new and better drugs for the treatment of type 2 diabetes and related disorders are needed.

One property of the compounds of this invention is that in many cases they can convert preadipocyte cells to adipocytes i.e. induce adipocyte differentiation. The ability of a molecule to induce differentiation of a particular cell type or cell types is also known to often correlate to anticancer activities.

Small molecules that can be effective for the treatment of diabetes and/or disorders of carbohydrate metabolism were disclosed in U.S. Pat. No. 6,515,003, issued Feb. 4, 2003, based on U.S. patent application Ser. No. 09/652,810, filed Aug. 31, 2000, which claimed priority to U.S. Provisional Patent Application No. 60/151,670, filed Aug. 31, 1999. Related small molecules that can be useful in the treatment of certain cancers were disclosed in PCT Patent Application WO 01/16122, published Mar. 8, 2001, which claimed priority to the same U.S. Provisional Patent Application No. 60/151,670 cited above. The disclosures of all the above-described patent documents are hereby incorporated herein by this reference, for both their chemical structural disclosures, their teachings of the biological activities of those compounds, and methods for their use as pharmaceutical compositions.

There is however a continuing need for new drugs for the treatment of type 2 diabetes and associated disorders of carbohydrate and/or lipid metabolism, including hyperlipidemia and hypercholesterolemia. In particular, new drugs that can control the blood sugar levels of diabetics, and simultaneously control hyperlipidemia and/or hypercholesteremia so as to lessen or prevent atherosclerosis would be of high value for the treatment of diabetes.

SUMMARY OF THE INVENTION

The present invention relates to substituted heterocycles which are useful in the treatment of type 2 diabetes and related diseases related to carbohydrate metabolism. Unexpectedly, it has been discovered that the drugs can simultaneously treat disorders related to lipid metabolism, such as hyperlipidemia and/or hypercholesterolemia, which can be associated with atherosclerosis.

The compounds of the invention can also be useful in treating diseases of uncontrolled proliferation, such as cancers.

Some embodiments of the invention relate to a first genus of compounds of Formula (300):

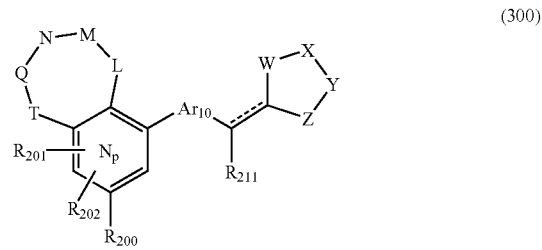

(300)

wherein:
a) $R_{200}$, $R_{201}$ and $R_{202}$ are independently selected from hydrogen, hydroxyl, a halogen, amino, or an organic residue comprising 1 to 12 carbon atoms;

b) $N_p$ are the number of heteroaryl ring nitrogens selected from 0, 1 or 2;

c) L, M, N, Q and T residues are independently selected from —C(O)—, —C(S)—, —O—, —S—, —N($R_{203}$)—, —N($R_{204}$)—, —C($R_{205}$)($R_{206}$)—, —C($R_{207}$) ($R_{208}$)—, or —C($R_{209}$)($R_{210}$)— residues, and from zero to two of the L, M, N, Q or T residues can be absent;

wherein:
  i) $R_{200}$, $R_{201}$, $R_{202}$, $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic residue comprising 1 to 12 carbon atoms; or two of the $R_{203}$, $R_{204}$, $R_{205}$, $R_{206}$, $R_{207}$, $R_{208}$, $R_{209}$ and $R_{210}$ residues can be connected together to form an exocyclic substituent residue comprising 1 to 6 ring carbon atoms and from 0 to 3 optional ring heteroatoms selected from O, S, or N; and
  ii) L, M, N, Q and T do not form an amide residue;

d) $Ar_{10}$ is an aryl, substituted aryl, heteroaryl, or substituted heteroaryl residue comprising from 3 to 6 ring carbon atoms and from 0 to 3 optional ring heteroatoms selected from O, S, or N;

e) $R_{211}$ is hydrogen, hydroxy, or an organic residue comprising 1 to 10 carbon atoms;

f) - - - is either present or absent;

g) W, X, Y and Z are independently or together —C(O)—, —C(S)—, —S—, —O— or —NH—, to form a 2,4-thiazolidinedione, 2-thioxo-thiazolidine-4-one, 2,4-imidazolidinedione or 2-thioxo-imidazolidine-4-one residue; or a pharmaceutically acceptable salt thereof.

In related embodiments, the invention relates to a second genus of compounds having the structure

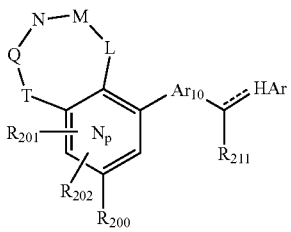

wherein:
a) p is 0, 1 or 2;
b) L, M, N, Q and T residues are independently selected from, —O—, —S—, —S(O)—, —S(O)$_2$—, —N(R$_{203}$)—, —N(R$_{204}$)—, —C(R$_{205}$)(R$_{206}$)—, —C(R$_{207}$) (R$_{208}$)—, or —C(R$_{209}$)(R$_{210}$)— residues, with the proviso that one or two of the L, M, N, Q or T radicals can be absent;
c) R$_{200}$, R$_{201}$, R$_{202}$, R$_{203}$, R$_{204}$, R$_{205}$, R$_{206}$, R$_{207}$, R$_{208}$, R$_{209}$, and R$_{210}$ are independently selected from hydrogen, hydroxyl, a halogen, amino, or an organic radical;
d) Ar$_{10}$ is an aryl, substituted aryl, heteroaryl, or substituted heteroaryl radical;
e) the bicyclic radical

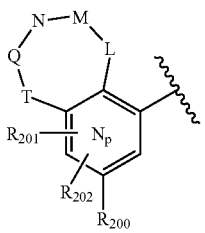

comprises from 6 to 20 carbon atoms;
f) R$_{211}$ is hydrogen, hydroxy, or an organic radical;
g) - - - is either present or absent; and
h) HAr has the structure

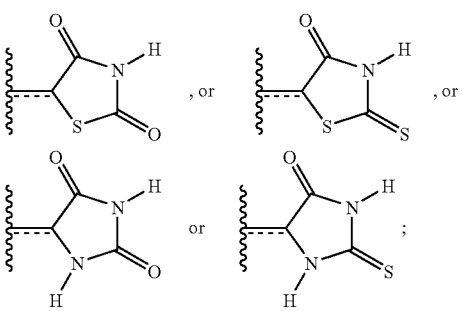

or a pharmaceutically acceptable salt thereof.

In another aspect, this invention relates to the use of the compounds of the inventions disclosed above for modulating lipid metabolism, carbohydrate metabolism, or lipid and carbohydrate metabolism. The compounds are also useful for treating diseases of uncontrolled cellular proliferation such as cancer; and the treatment of inflammatory diseases.

This invention also relates to a method for the treatment of type 2 diabetes and related diseases, by modulating lipid metabolism, carbohydrate metabolism, or lipid and carbohydrate metabolism. The methods comprise administering to a mammal, preferably a human, diagnosed as needing such treatment or modulation, one or more of the compounds of the invention or a pharmaceutical composition thereof. The invention also provides for a method of treatment of a disease of uncontrolled cellular proliferation comprising administering to a mammal diagnosed as having a disease of uncontrolled cellular proliferation and a method of treating an inflammatory disease comprising administering one or more of the compounds of the invention to a mammal diagnosed as having an inflammatory disease such as atherosclerosis.

In another aspect, this invention relates to a pharmaceutical composition comprising one or more compounds disclosed herein in admixture with one or more pharmaceutically acceptable excipients.

DETAILED DESCRIPTION

Figure 1:
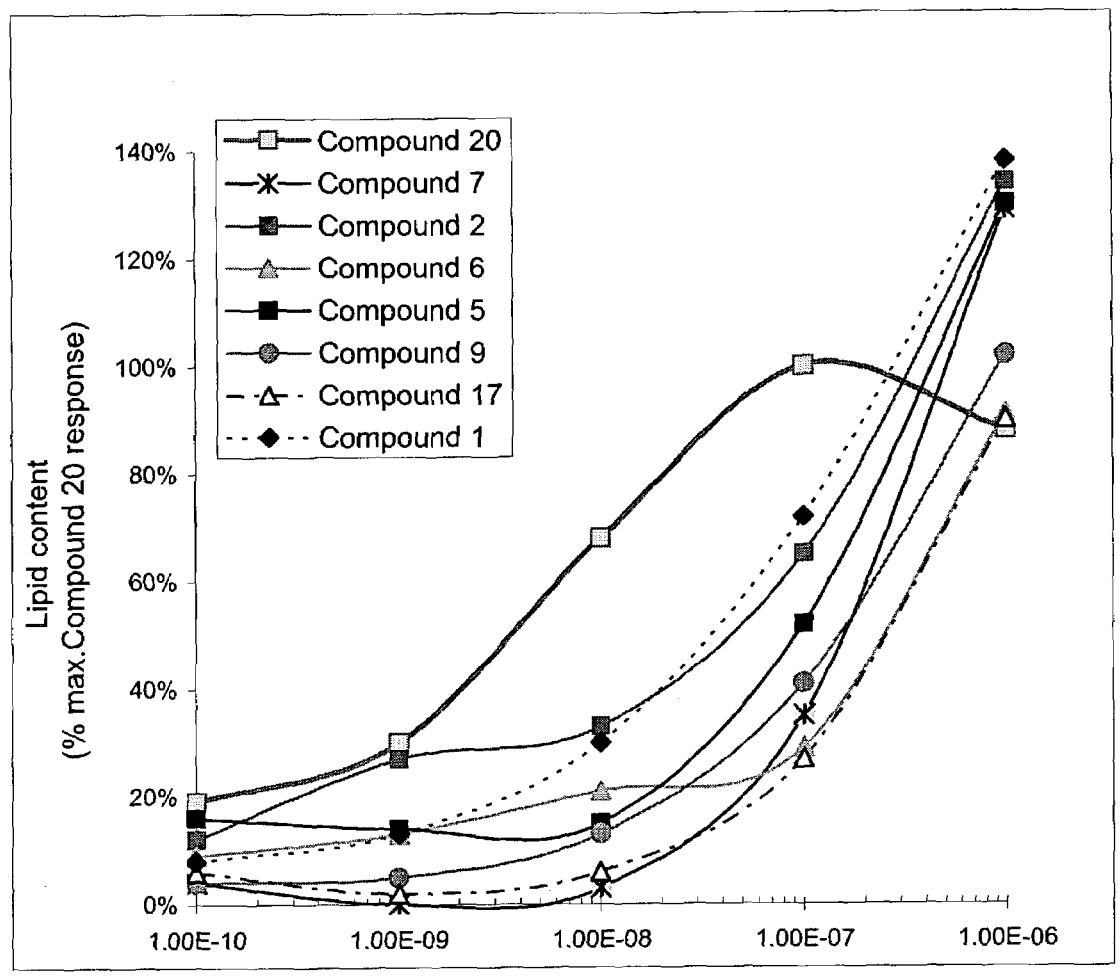
FIG. 1 shows the activity of the compounds of the invention for inducing the differentiation of 3T3-L1 preadipocytes into adipocytes.

The present invention can be understood more readily by reference to the following detailed description of various embodiments of the invention and the Examples included therein and to the Figures and their previous and following description. Before the present compounds, compositions, and/or methods are disclosed and described, it is to be understood that this invention is not limited to specific synthetic methods, specific pharmaceutical carriers or formulations, or to particular modes of administering the compounds of the invention, as such can, of course, vary. It is also to be understood that the terminology used herein is for the purpose of describing particular embodiments only and is not intended to be limiting.

DEFINITIONS

In the specification and Formulae described herein the following terms are hereby defined.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

By the term "effective amount" of a compound as provided herein is meant a sufficient amount of the compound to provide the desired regulation of a desired function, such as gene expression, protein function, or a disease condition. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The term "alkyl" denotes a hydrocarbon group or residue which is structurally similar to a non-cyclic alkane compound modified by the removal of one hydrogen from the non-cyclic alkane and the substitution therefore of a non-hydrogen group or residue. Alkyls comprise a noncyclic, saturated, straight or branched chain hydrocarbon residue having from 1 to 12 carbons, or 1 to 8 carbons, or 1 to 6 carbons. Examples of such alkyl radicals include methyl, ethyl, n-propyl, iso-propyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms.

The term "substituted alkyl" denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When more than one substituent group is present then they can be the same or different. The organic substituent groups can comprise from 1 to 12 carbon atoms, or from 1 to 6 carbon atoms, or from 1 to 4 carbon atoms. The term "substituted alkyl" denotes a radical containing 1 to 12 carbons of the above definitions that are substituted with one or more groups, but preferably one, two or three groups, selected from hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different.

The term "hydroxyalkyl" denotes an alkyl radical substituted with one or more hydroxy radicals. Lower hydroxyalkyl radicals comprise from 1 to 4 carbon atoms. Examples of hydroxyalkyl groups include hydroxymethyl radicals (—CH$_2$OH), 1-hydroxyethyl (—CH(OH)CH$_3$), 2-hydroxyethyl radicals (—CH$_2$CH$_2$OH), and like higher homologs.

The term "alkoxyalkyl" denotes an alkyl radical substituted with an alkoxy or a hydroxyalkyl radical. Lower alkoxyalkyl groups comprise from 1 to 6 carbon atoms. Examples of alkoxyalkyl groups include alkoxymethyl radicals (—CH$_2$—O—R, where R is an alkyl radical), alkoxyethyl radicals (—CH$_2$CH$_2$—O—R, wherein R is an alkyl radical).

The term "alkenyl" denotes an alkyl residue as defined above that comprises at least one carbon-carbon double bond. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "substituted alkenyl" denotes an alkenyl residue as defined above definitions that is substituted with one or more groups, but preferably one, two or three groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "alkynyl" denotes a residue as defined above that comprises at least one carbon-carbon double bond. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "substituted alkynyl" denotes an alkylnyl residue of the above definition that is substituted with one or more groups, but preferably one or two groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "cycloalkyl" denotes a hydrocarbon group or residue which is structurally similar to a cyclic alkane compound modified by the removal of one hydrogen from the cyclic alkane and substitution therefore of a non-hydrogen group or residue. Cycloalkyl groups, or residues radical contain 3 to 18 carbons, or preferably 4 to 12 carbons, or 5 to 8 carbons. Examples include as cyclopropyl, cyclobutyl, cyclopentyl, cyclohexyl, cycloheptyl, decahydronapthyl, adamantyl, and like residues. The term "cycloalkyl" denotes a radical containing 3 to 8 carbons, such as cyclopropyl, cyclobutyl, cyclopentyl, cyclohexyl, cycloheptyl and the like. The term "substituted cycloalkyl" denotes a cycloalkyl as defined above that is further substituted with one or more groups selected from halogen, alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one group, they can be the same or different.

The term "substituted cycloalkyl" denotes a cycloalkyl residue as defined above that is further substituted with one, two, or more additional organic or inorganic groups that can include but are not limited to halogen, alkyl, substituted alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

The term "cycloalkenyl" denotes a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like. The term "substituted cycloalkenyl" denotes a cycloalkyl as defined above further substituted with one or more groups selected from halogen, alkyl, hydroxyl, alkoxy, substituted alkoxy, haloalkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkenyl is substituted with more than one group, they can be the same or different. The organic substituent groups can comprise from 1 to 12 carbon atoms, or from 1 to 6 carbon atoms, or from 1 to 4 carbon atoms.

The term "alkoxy" as used herein denotes an alkyl residue, defined above, attached directly to a oxygen to form an ether residue. Examples include methoxy, ethoxy, n-propoxy, iso-propoxy, n-butoxy, t-butoxy, iso-butoxy and the like.

The term "substituted alkoxy" denotes an alkoxy residue of the above definition that is substituted with one or more substituent groups, but preferably one or two groups, which include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "mono-substituted amino" denotes an amino substituted with one organic substituent groups, which include but are not limited to alkyl, substituted alkyl or arylalkyl wherein the terms have the same definitions found hereinabove.

The term "di-substituted amino" denotes an amino residue substituted with two radicals that can be same or different selected from aryl, substituted aryl, alkyl, substituted alkyl or arylalkyl wherein the terms have the same definitions found throughout. Some examples include dimethylamino, methylethylamino, diethylamino and the like.

The term "haloalkyl" denotes a alkyl residue as defined above, substituted with one or more halogens, preferably fluorine, such as a trifluoromethyl, pentafluoroethyl and the like.

The term "haloalkoxy" denotes a haloalkyl residue as defined above, that is directly attached to an oxygen to form trifluoromethoxy, pentafluoroethoxy and the like.

The term "acyl" denotes a R—C(O)— residue containing 1 to 8 carbons. Examples include but are not limited to formyl, acetyl, propionyl, butanoyl, iso-butanoyl, pentanoyl, hexanoyl, heptanoyl, benzoyl and the like.

The term "acyloxy" denotes a an acyl radical as defined above directly attached to an oxygen to form an R—C(O) O— residue. Examples include but are not limited to acetyloxy, propionyloxy, butanoyloxy, iso-butanoyloxy, benzoyloxy and the like.

The term "aryl" denotes an ring radical containing 6 to 18 carbons, or preferably 6 to 12 carbons, having at least one six-membered aromatic "benzene" residue therein. Examples of such aryl radicals include phenyl and naphthyl. The term "substituted aryl" denotes an aryl ring radical as defined above that is substituted with one or more, or preferably 1, 2, or 3 organic or inorganic substituent groups, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups can comprise from 1 to 12 carbon atoms, or from 1 to 6 carbon atoms, or from 1 to 4 carbon atoms.

The term "heteroaryl" denotes an aryl ring radical as defined above, wherein at least one of the carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can comprise from 1 to 12 carbon atoms, or from 1 to 6 carbon atoms, or from 1 to 4 carbon atoms.

The term "halo" or "halogen" refers to a fluoro, chloro, bromo or iodo group.

The term "thioalkyl" denotes a sulfide radical containing 1 to 8 carbons, linear or branched. Examples include methylsulfide, ethyl sulfide, isopropylsulfide and the like.

The term "thiohaloalkyl" denotes a thioalkyl radical substituted with one or more halogens. Examples include trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include carbomethoxy, carboethoxy, carboisopropoxy and the like.

The term "alkylcarboxamide" denotes a single alkyl group attached to the amine of an amide, wherein alkyl has the same definition as found above. Examples include N-methylcarboxamide, N-ethylcarboxamide, N-(iso-propyl)carboxamide and the like. The term "substituted alkylcarboxamide" denotes a single "substituted alkyl" group, as defined above, attached to the amine of an amide.

The term "dialkylcarboxamide" denotes two alkyl or arylalkyl groups that are the same or different attached to the amine of an amide, wherein alkyl has the same definition as found above. Examples of a dialkylcarboxamide include N,N-dimethylcarboxamide, N-methyl-N-ethylcarboxamide and the like. The term "substituted dialkylcarboxamide" denotes two alkyl groups attached to the amine of an amide, where one or both groups is a "substituted alkyl", as defined above. It is understood that these groups can be the same or different. Examples include N,N-dibenzylcarboxamide, N-benzyl-N-methylcarboxamide and the like.

The term "arylalkyl" defines an alkylene, such as —CH$_2$— for example, which is substituted with an aryl group that can be substituted or unsubstituted as defined above. Examples of an "arylalkyl" include benzyl, phenethylene and the like.

The term "organic residue" defines a carbon containing residue, i.e. a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono- or di-substituted amino, amide groups, etch. Organic resides-can preferably comprise 1 to 18 carbon atoms, 1 to 15, carbon atoms, 1 to 12 carbon atoms, 1 to 8 carbon atoms, or 1 to 4 carbon atoms.

The term "amide" as defined hereby and used in the instant specification refers to a functional group or residue that contains a carbonyl (CO) group bound to a nitrogen atom, i.e. a residue having the formula:

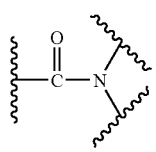

A residue of a chemical species, as used in the specification and concluding claims, refers to the a structural fragment, or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —OCH$_2$CH$_2$O— repeat units in the polyester, regardless of whether ethylene glycol is used to prepare the polyester.

Similarly, a 2,4-thiazolidinedione residue in a chemical compound refers to one or more 2,4-thiazolidinedione moieties of the compound, regardless of whether the residue was obtained by reacting 2,4-thiazolidinedione to obtain the compound.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

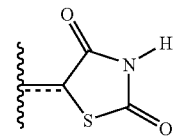

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Inorganic radicals," as the term is defined and used herein contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

"Organic radicals" as the term is defined and used herein contain one or more carbon atoms. An organic radical can have, for example, 1–26 carbon atoms, 1–18 carbon atoms, 1–12 carbon atoms, 1–6 carbon atoms, or 1–4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1–10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

COMPOUNDS OF THE INVENTION

Some embodiments of the invention relate to a first genus of bicyclic compounds of Formula (300):

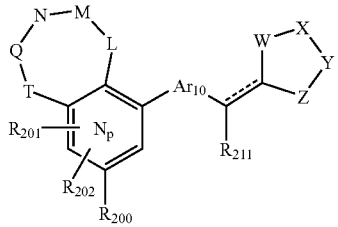

(300)

wherein:
a) $R_{200}$, $R_{201}$ and $R_{202}$ are independently selected from hydrogen, hydroxyl, a halogen, amino, or an organic residue comprising 1 to 12 carbon atoms;
b) $N_p$ are the number of heteroaryl ring nitrogens selected from 0, 1 or 2;
c) L, M, N, Q and T residues are independently selected from —C(O)—, —C(S)—, —O—, —S—, —N(R$_{203}$)—, —N(R$_{204}$)—, —C(R$_{205}$)(R$_{206}$)—, —C(R$_{207}$)(R$_{208}$)—, or —C(R$_{209}$)(R$_{210}$)— residues, and from zero to two of the L, M, N, Q or T residues can be absent;
wherein:
i) $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic residue comprising 1 to 12 carbon atoms; or two of the $R_{203}$, $R_{204}$, $R_{205}$, $R_{206}$, $R_{207}$, $R_{208}$, $R_{209}$ and $R_{210}$ residues can be connected together to form an exocyclic substituent residue comprising 1 to 6 ring carbon atoms and from 0 to 3 optional ring heteroatoms selected from O, S, or N; and
ii) L, M, N, Q and T do not form an amide residue;
d) $Ar_{10}$ is an aryl, substituted aryl, heteroaryl, or substituted heteroaryl residue comprising from 3 to 6 ring carbon atoms and from 0 to 3 optional ring heteroatoms selected from O, S, or N;
e) $R_{211}$ is hydrogen, hydroxy, or an organic residue comprising 1 to 10 carbon atoms;
f) - - - is either present or absent;

g) W, X, Y and Z are independently or together —C(O)—, —C(S)—, —S—, —O— or —NH—, to form a 2,4-thiazolidinedione, 2-thioxo-thiazolidine-4-one, 2,4-imidazolidinedione or 2-thioxo-imidazolidine-4-one residue;

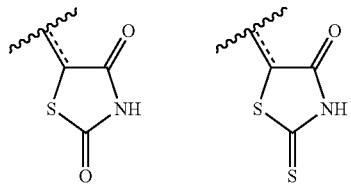

2,4-thiazolidinedione  2-thioxo-thiazolidine-4-one

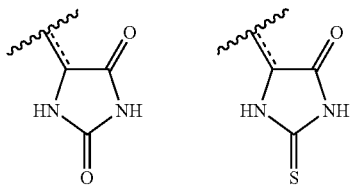

2,4-imidazolidinedione  2-thioxo-imidazolidine-4-one or
a pharmaceutically acceptable salt thereof.

The genus of compounds described above shall be termed herein the "first" genus of bicyclic compounds.

In a related but alternative embodiment, the invention relates to another "second" genus of bicyclic compounds having the structure

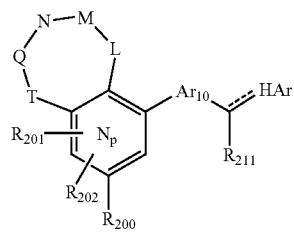

wherein:
a) p is 0, 1 or 2;
b) L, M, N, Q and T residues are independently selected from, —O—, —S—, —S(O)—, —S(O)$_2$—, —N(R$_{203}$)—, —N(R$_{204}$)—, —C(R$_{205}$)(R$_{206}$)—, —C(R$_{207}$)(R$_{208}$)—, or —C(R$_{209}$)(R$_{210}$)— radicals, with the proviso that one or two of the L, M, N, Q or T radicals can be absent;
c) $R_{200}$, $R_{201}$, $R_{202}$, $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic radical comprising 1 to 12 carbon atoms;
d) $Ar_{10}$ is an aryl, substituted aryl, heteroaryl, or substituted heteroaryl radical comprising 2 to 18 carbon atoms;

e) the radical

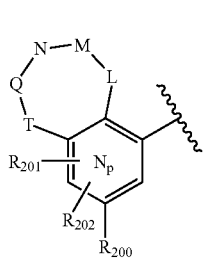

comprises from 6 to 20 carbon atoms;

f) $R_{211}$ is hydrogen, hydroxy, or an organic residue comprising 1 to 10 carbon atoms;

g) - - - is either present or absent; and h) HAr has the structure

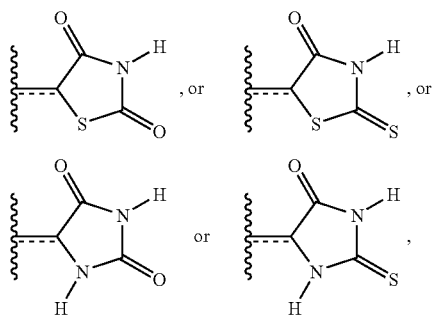

or a pharmaceutically acceptable salt thereof.

The two genuses of compounds disclosed immediately above share a number of common features, but differ in some aspects. The description of further and more detailed embodiments to follow below is intended to be applicable, to the extent possible and reasonable, to both the "first" and "second" genuses of compounds described above. Some differences between the first and second genuses will be noted.

In the embodiments relating to the first genus of compounds, the W, X, Y and Z radicals, together with a carbon atom, form one of four separate five membered heterocycles, selected from a 2,4-thiazolidinedione, 2-thioxo-thiazolidine-4-one, 2,4-imidazolidinedione or 2-thioxo-imidazolidine-4-one residue or radical, the structures of which are shown in the drawings below:

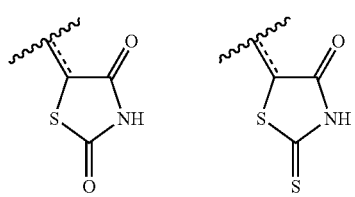

2,4-thiazolidinedione  2-thioxo-thiazolidine-4-one

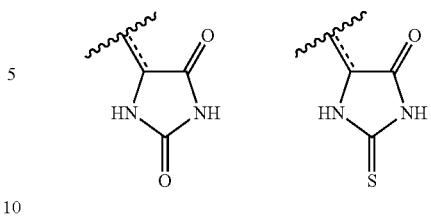

2,4-imidazolidinedione  2-thioxo-imidazolidine-4-one

For purposes of ease of reference and brevity, the 2,4-thiazolidinedione, 2-thioxo-thiazolidine-4-one, 2,4-imidazolidinedione or 2-thioxo-imidazolidine-4-one heterocyclic residues can be generically termed "HAr" heterocyclic residues or radicals. The second genus of compounds above employs the "HAr" terminology, but intends the same set of four heterocyclic residues or radicals, namely 2,4-thiazolidinedione, 2-thioxo-thiazolidine-4-one, 2,4-imidazolidinedione or 2-thioxo-imidazolidine-4-one radicals or residues.

The compounds of the invention, including both the first and second genuses, comprise at least one "bicyclic" residue or radical of the following formula:

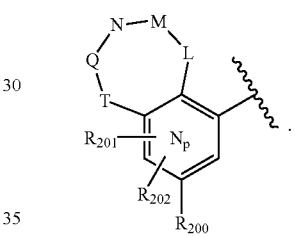

In the first genus of compounds, the L, M, N, Q and T radicals or residues are independently selected from —C(O)—, —C(S)—, —O—, —S—, —N($R_{203}$)—, —N($R_{204}$)—, —C($R_{205}$)($R_{206}$)—, —C($R_{207}$)($R_{208}$)—, or —C($R_{209}$)($R_{210}$)— residues, with the proviso that L, M, N, Q and T do not form an amide residue. In the second genus of compounds, the L, M, N, Q and T radicals or residues are independently selected from —O—, —S—, —S(O)—, —S(O)$_2$—, —N($R_{203}$)—, —N($R_{204}$)—, —C($R_{205}$)($R_{206}$)—, —C($R_{207}$)($R_{208}$) —, or —C($R_{209}$)($R_{210}$)— radicals. It should be noted that the ring comprising the L, M, N, Q and T radicals or residues is not an aromatic ring.

It should be understood that, with respect to the descriptions, formulas and drawings above, the "N" in the "LMNQT" ring can represent a nitrogen atom or one of the two listed —N($R_{203}$)—, or —N($R_{204}$)— radicals, but the N could also represent any of the listed residues.

In both genuses of compounds, the $R_{200}$, $R_{201}$, $R_{202}$, $R_{203}$, $R_{204}$, $R_{205}$, $R_{206}$, $R_{207}$, $R_{208}$, $R_{209}$, and $R_{210}$ residues or radicals can be independently selected from residues or radicals that can include but are not limited to hydrogen, hydroxyl, a halogen, amino, or an organic residue. Examples of suitable organic residues or radicals include but are not be limited to an alkyl, substituted alkyl, haloalkyl, alkenyl, substituted alkenyl, alkynyl, substituted alkynyl, acyloxy, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide residue. In certain embodiments, the organic residues or radicals comprise from 1 to 12 carbon atoms, or 1 to 8 carbon atoms, or 1 to 6 carbon atoms, or 1 to 4 carbon atoms.

It is also to be understood that one or two of the L, M, N, Q or T residues can be absent. For example, the bicyclic residues can comprise a "LMNQT" ring that has from five to seven atoms in the non-aromatic ring. Examples of such bicyclic residues include:

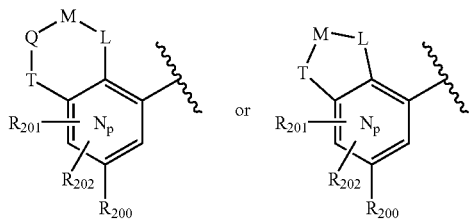

Although not wishing to be bound by theory, the compounds of the invention, including the bicyclic radical and its various substituents are selected so as to have a geometry, size, and polarity that is suitable to allow the compounds of the invention to interact with and substantially fill, yet fit within, the binding regions of the target biological molecules, so as to contribute to the effective binding of the compounds to the binding sites in the biological target molecules. Therefore, in some embodiments, the bicyclic radical or residue, together with the L, M, N, Q and T and all the associated $R_{200}$, $R_{201}$, $R_{202}$, $R_{203}$, $R_{204}$, $R_{205}$, $R_{206}$, $R_{207}$, $R_{208}$, $R_{209}$, and $R_{210}$ substituent radicals a comprise from 6 to 20 carbon atoms, or from 7 to 18 carbon atoms, or from 8 to 16 carbon atoms, or from 9 to 14 carbon atoms.

In certain embodiments, the bicyclic residues comprise at least one ring heteroatom or heteroatomic group, which can be present at any one of the L, M, N, Q, or T positions. For example, L, M, N, Q and T together with a substituted or unsubstituted aryl can form a bicyclic ring residue or radical with one heteroatom or heteroatomic group having the Formulas (305a–f):

(305a)
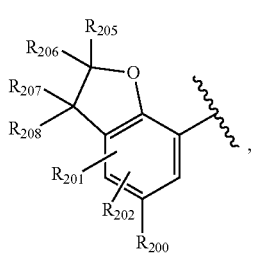

(305b)
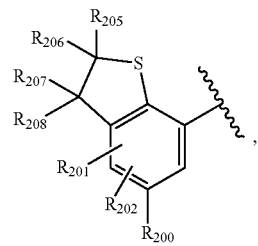

(305c)
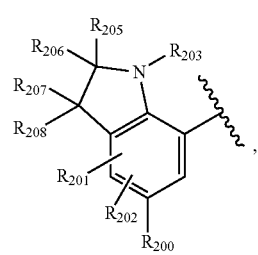

(305d)
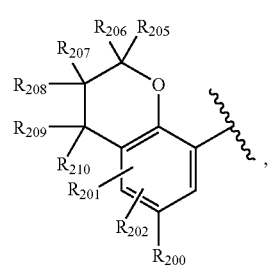

(305e)
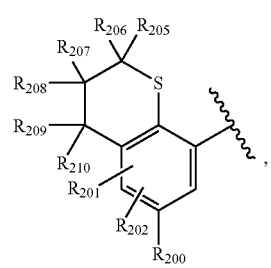

(305f)
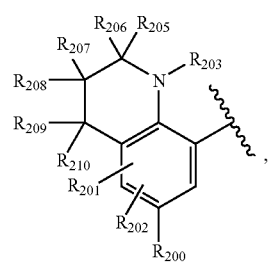

In other embodiments, L, M, N, Q and T together with a substituted or unsubstituted aryl can form a bicyclic ring residue or radical with two heteroatoms or heteroatomic groups, as exemplified by the radicals having the Formulas (305g–k):

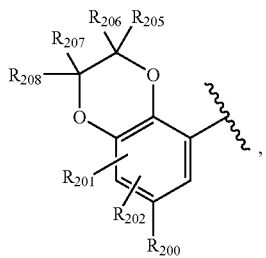
(305g)

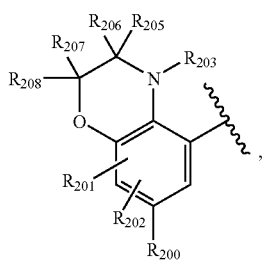
(305h)

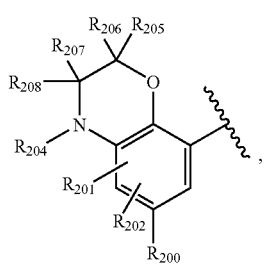
(305i)

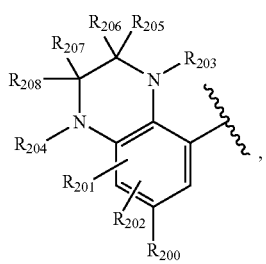
(305j)

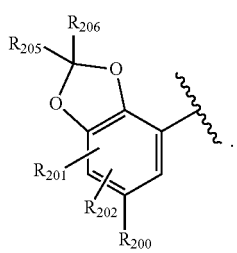
(305k)

In some embodiments of the bicyclic residues or radicals, nitrogen is present in the aryl ring of the bicyclic residue, i.e. p=1, so that L, M, N, Q and T together with a substituted or unsubstituted heteroaryl form a bicyclic pyridine residue or radical. Examples of such bicyclic pyridine radicals include but are not limited to Formulas (305l–m):

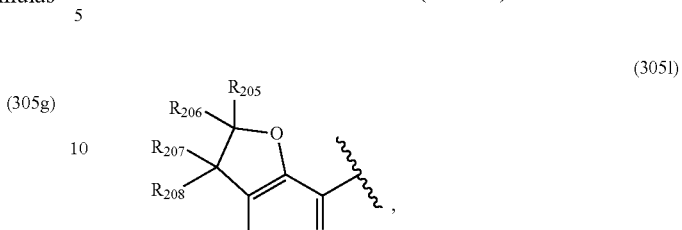
(305l)

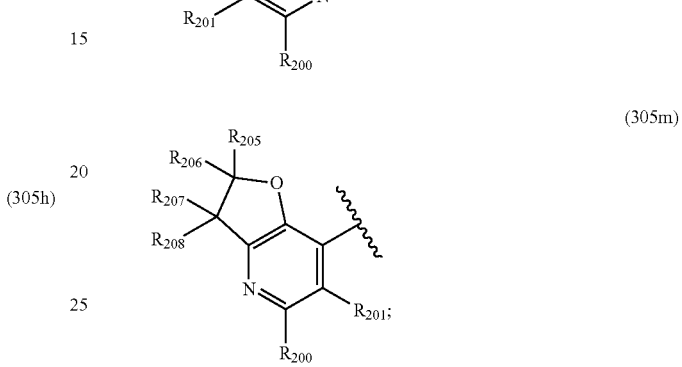
(305m)

Alternatively, the heteroaryl ring can comprise heteroaromatic residues having two nitrogen atoms, i.e. p=2. An example of such a bicyclic "pyrimidene" residue or radical is shown below.

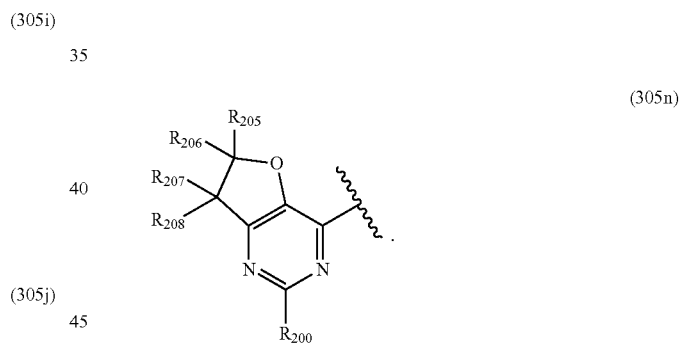
(305n)

The $R_{200}$, $R_{201}$, $R_{202}$, $R_{203}$, $R_{204}$, $R_{205}$, $R_{206}$, $R_{207}$, $R_{208}$, $R_{209}$, and $R_{210}$ substituents for the bicyclic residues or radicals of the invention can be independently selected from inorganic or organic residues or radicals, Suitable substituents include but are not limited to hydrogen, an alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide.

Some embodiments of the invention relate to compounds wherein L, M, N, Q and T together form a partially reduced benzopyran ring of Formula (306):

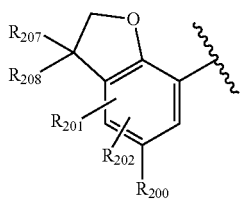

(306)

wherein:

$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{207}$ and $R_{208}$ are independently or together alkyl or substituted alkyl.

Some embodiments of the invention relate to where L, M, N, Q and T together form a partially reduced benzothiofuran ring of Formula (307):

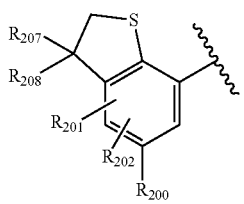

(307)

wherein:

$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{207}$ and $R_{208}$ are independently or together alkyl or substituted alkyl.

Some embodiments of the invention relate to where L, M, N, Q and T together form a partially reduced benzopyrrole ring of Formula (308):

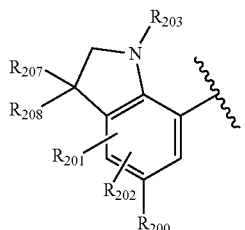

(308)

wherein:

$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{203}$, $R_{207}$ and $R_{208}$ are independently or together hydrogen, alkyl or substituted alkyl.

In many embodiments of the compounds of the invention, $R_{200}$ is not hydrogen. In some embodiments, $R_{200}$ is selected from an alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide.

In some embodiments, the $R_{200}$ residue or radical is selected from an alkyl, substituted alkyl, aryl, substituted aryl, heteroaryl, or substituted heteroaryl having 1 to 10 carbon atoms or 2–8 carbon atoms or 3–6 carbon atoms. Hydroxyalkyls or alkoxyalkyls are sometimes favored substituted alkyls.

In some embodiments $R_{200}$ is an alkyl. Some examples $R_{200}$ is a straight or branched alkyl of $C_1$–$C_8$. In other examples $R_{200}$ is a straight or branched alkyl of $C_1$–$C_6$. In still other examples $R_{200}$ is a straight or branched alkyl of $C_1$–$C_4$, such as methyl, ethyl, i-propyl, n-propyl, i-butyl, n-butyl, and t-butyl.

In some embodiments $R_{200}$ is an alkyl of $C_1$–$C_4$ that is branched. In some embodiments, isobutyl groups are preferred $R_{200}$ groups.

In some embodiments $R_{200}$ is an alkoxy of $C_1$–$C_8$ that is either straight chain or branched. In other examples $R_{200}$ is an alkoxy of $C_1$–$C_6$ that is either straight chain or branched.

In still other examples $R_{200}$ is an alkoxy of $C_1$–$C_4$ that is either straight chain or branched.

In some embodiments $R_{200}$ is an aryl or substituted aryl. In other embodiments $R_{200}$ is a heteroaryl or substituted heteroaryl. Some representative examples of substituted aryls and substituted heteroaryl shown in Formulae (310a and 310b):

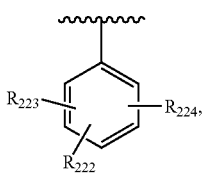
(310a)

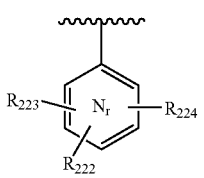
(310b)

wherein $R_{222}$, $R_{223}$ and $R_{223}$ are organic or inorganic radicals. Suitable radicals include but are not limited to hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide; and $N_r$ represent the number of nitrogen in the ring wherein "r" is 1, 2 or 3 thus forming a substituted or unsubstituted pyridyl, pyrimidinyl or triazinyl respectively. Some other embodiments where $R_{200}$ is a heteroaryl or substituted heteroaryl include five-membered rings. Some interesting heteroaryl and substituted heteroaryl residues are five membered rings, where some representative examples are of the Formulae (312a–x):

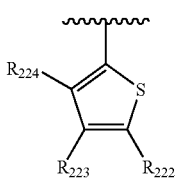
(312a)

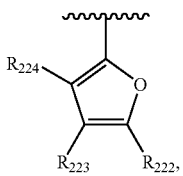
(312b)

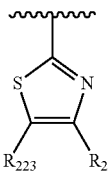
(312c)

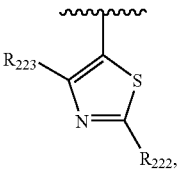
(312d)

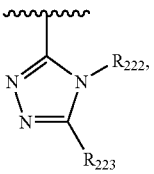
(312e)

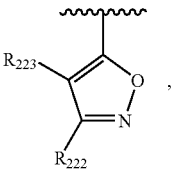
(312f)

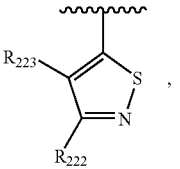
(312g)

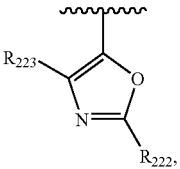
(312h)

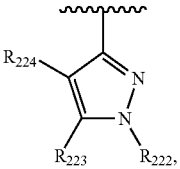
(312i)

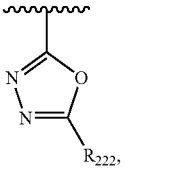
(312j)

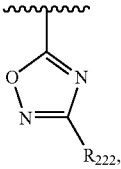
(312k)

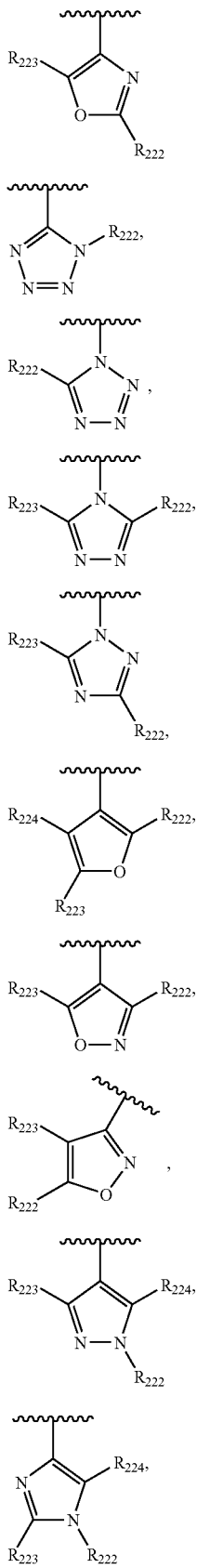

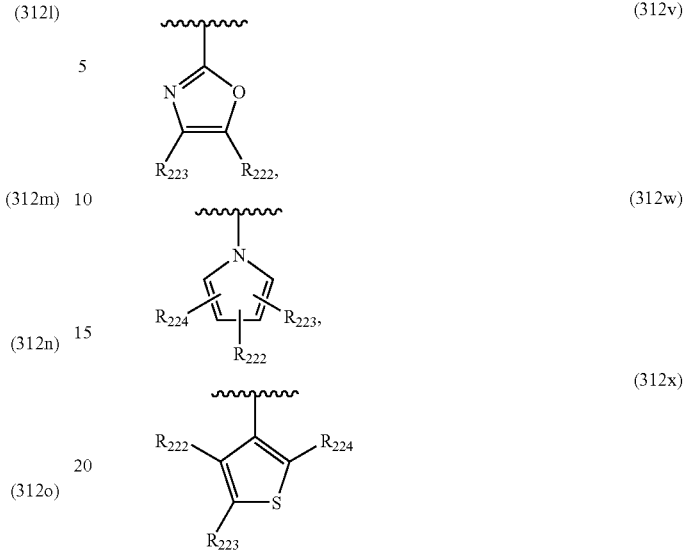

wherein $R_{222}$, $R_{223}$ and $R_{224}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide. In some embodiments, $R_{222}$, $R_{223}$ and $R_{224}$ are hydrogen, a halogen, or a $C_1$–$C_4$ alkyl.

It is to be understood that compounds of Formula (312a–x) possessing heteroaryl residues wherein N—$R_{222}$ is a hydrogen, tautomers are possible and are within the scope of the invention. For example, triazole (312e) can exist in several tautomeric forms when $R_{222}$ is hydrogen. These forms can be represented as shown:

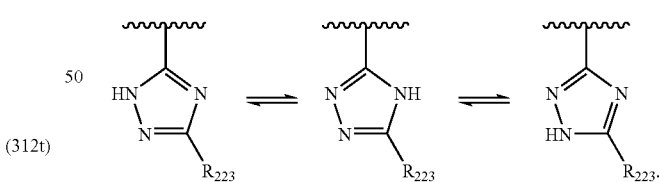

Other represented structures that can exist as various tautomeric forms include, for example, (312i), (312m), (312t) and (312u).

Some embodiments of the invention relate to compounds of the first or second genuses wherein —C($R_{205}$)($R_{206}$)—, —C($R_{207}$)($R_{208}$)— and —C($R_{209}$)($R_{210}$)— independently form a cycloalkyl optionally substituted with O, S or N-alkyl. For example, in some embodiments of bicyclic residues (305a–n) and (306)–(308), the $R_{207}$ and $R_{208}$ radicals can optionally be bonded together to form an additional exocyclic cycloalkyl radical, which can optionally comprise 1 or 2 heteroatoms selected from —O—, —S—, —NH—, or —N(alkyl)-. Representative examples of such exocyclic cycloalkyls with optional heteroatoms include but are not limited to exocyclic cyclopropyl, cyclobutyl, cyclopentyl, tetrahydrofuranyl, pyrrolidinyl and like radicals. For example, for residues of formula (305a), the ($R_{207}$) and ($R_{208}$) substituents of the —C($R_{207}$)($R_{208}$)— radical can be bonded together form a cycloalkyl having the Formulae (309a–c).

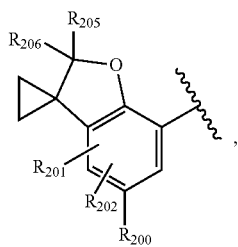
(309a)

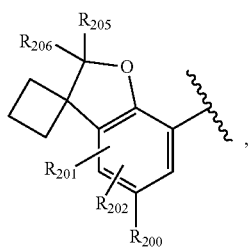
(309b)

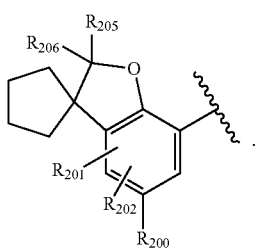
(309c)

Some embodiments of the invention relate to compounds of the invention wherein —C($R_{209}$)($R_{210}$)— form a cycloalkyl optionally substituted with —O—, —S—, —NH—, or —N(alkyl)-. Representative examples of bicyclic radicals of Formula (305d) wherein —C($R_{209}$)($R_{210}$)— together form a cycloalkyl are of the Formulae (309d–f).

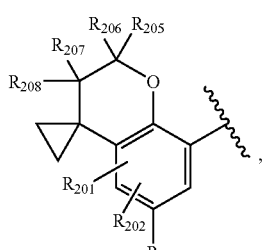
(309d)

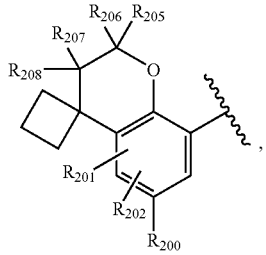
(309e)

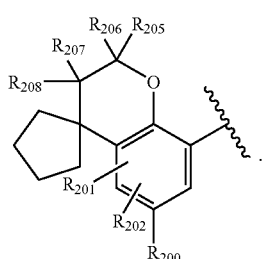
(309f)

Any two of the $R_{203}$, $R_{204}$, $R_{205}$, $R_{206}$, $R_{207}$, $R_{208}$, $R_{209}$ and $R_{210}$ residues can also be connected together to form an exocyclic substituent residue comprising 1 to 6 ring carbon atoms and from 0 to 3 optional ring heteroatoms selected from O, S, or N.

The $Ar_{10}$ residue is an aryl, substituted aryl, heteroaryl, or substituted heteroaryl residue. Although not wishing to be bound by theory, the compounds of the invention, including the $Ar_{10}$ radical and/or its various substituents are selected so as to have a geometry, size, and polarity that is suitable to allow the compounds of the invention to interact with and substantially fill, yet fit within, the binding regions of the target biological molecules, so as to contribute to the effective binding of the compounds to the binding sites in the biological target molecules. Therefore, in some embodiments, the $Ar_{10}$ radical or residue, together with all its associated substituent radicals together comprise from 2 to 18 carbon atoms, or from 3 to 16 carbon atoms, or from 4 to 12 carbon atoms, or from 5 to 10 carbon atoms.

In many embodiments, $Ar_{10}$ comprises from 3 to 6 ring carbon atoms and from 0 to 3 optional ring heteroatoms selected from O, S, or N. The aryl and heteroaryl rings (whether substituted or unsubstituted) include benzene, pyridine, pyrimidene, and pyrazine rings. The $Ar_{10}$ residue is at least disubstituted in the sense that it is bonded to both the bicyclic residue and the carbon atom connecting to the heterocyclic ring comprising W, X, Y and Z. The $Ar_{10}$ residue can have any ring substitution geometry (i.e. the bicyclic reside and the carbon atom substituents can be any of ortho, meta, and para with respect to each other.

Nevertheless, it has been found that in certain embodiments, especially those relating to the use of the compounds as agents for the treatment of diabetes, lipid or carbohydrate metabolism, or adipocyte differentiation, compounds having an $Ar_{10}$ residue with a "meta" ring geometry can be unexpectedly advantageous. Examples of such meta substituted $Ar_{10}$ residues include compounds of the Formulas (315a), (315b), (315c) or (315d):

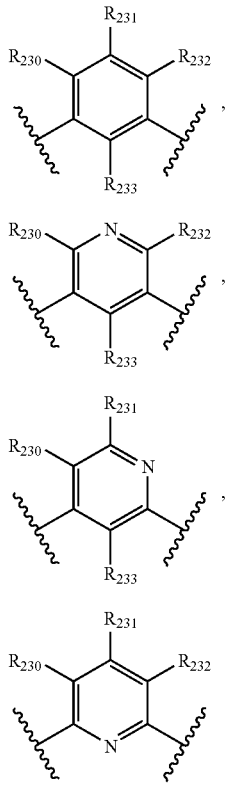

(315a)

(315b)

(315c)

(315d)

The $R_{230}$, $R_{231}$, $R_{232}$ and $R_{233}$ substituents for $Ar_{10}$ are independently selected from hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide. In many embodiments, each of the $R_{230}$, $R_{231}$, $R_{232}$ and $R_{233}$ substituents, if they are an organic residue or radical, will comprise between 1 to 8 carbons, or 1 to 6 carbons, or 1 to four carbons.

In some embodiments $R_{230}$ is not hydrogen. Although not wishing to be bound by theory, it is believed that such substituents can unexpectedly improve the activity of the compounds as agents for modulating lipid or carbohydrate metabolism, adipocyte differentiation, and/or producing anti-diabetic and/or anti-cholesteremic activity. In some embodiments, preferred $R_{125}$ residues are an alkyl, substituted alkyl, haloalkyl, alkoxy, substituted alkoxy, haloalkoxy, halogen, amino, mono-substituted amino, or disubstituted amino residue, particularly those comprising from 1 to 6 carbons, or 1 to four carbons.

In some embodiments $Ar_{10}$ is Formula (317a), (317b), (317c) or (317d):

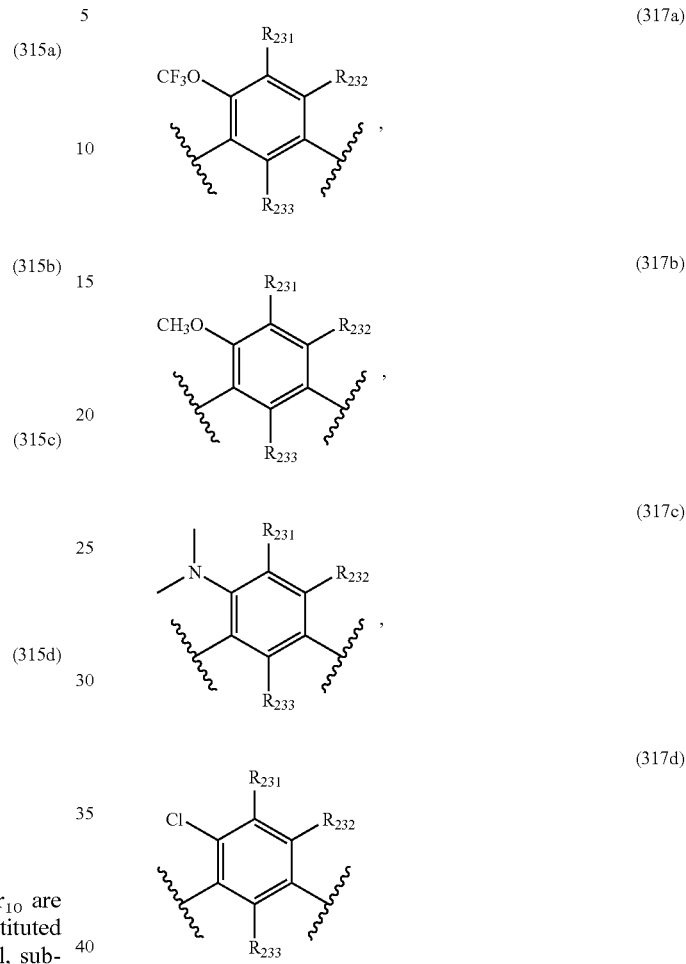

wherein $R_{231}$, $R_{232}$ and $R_{233}$ are independently or together hydrogen or halogen.

In some embodiments - - - represents a bond present, and therefore there is a carbon-carbon double bond between the carbon atom bonded to the $R_{211}$ substituent and the heterocycle comprising the W, X, Y, and Z radicals, and the compound is a "benzylidene" compound having Formula (320):

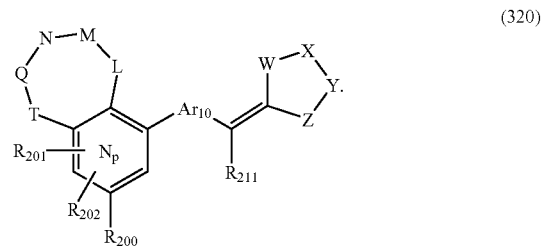

(320)

In some embodiments - - - represents a bond absent, and therefore there is a carbon-carbon single bond between the carbon atom bonded to the $R_{211}$ substituent and the heterocycle comprising the W, X, Y, and Z radicals, and the compound is a "benzyl" compound having Formula (322):

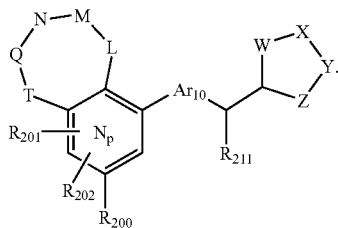
(322)

In some embodiments $R_{211}$ is hydrogen, alkyl, substituted alkyl, hydroxy, alkoxy or haloalkoxy. In some embodiments $R_{211}$ is hydrogen or alkyl. In many embodiments, $R_{211}$ is hydrogen.

The compounds of the invention can also be described more narrowly than the first and second genuses of embodiments described above. Two examples of such narrower descriptions are set forth below, but the meanings of the various relevant terms and symbols are intended the same as those same terms and symbols as described in the more detailed descriptions set forth above.

In one narrower description of the invention, the invention relates to a compound having the structure

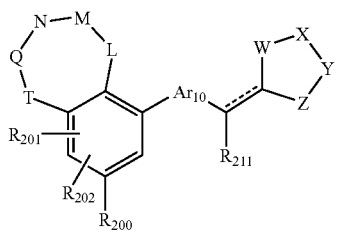

wherein:

a) the bicyclic radical

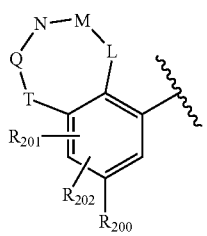

has the structure

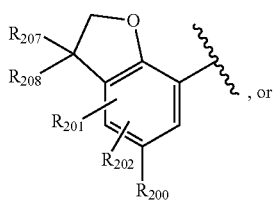, or

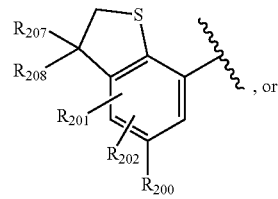, or

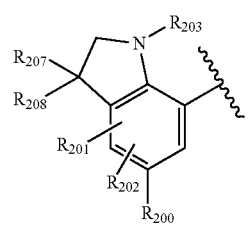

wherein $R_{200}$ comprises 1 to 10 carbon atoms and is selected from the group consisting of an alkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide;

$R_{201}$ and $R_{202}$ are independently selected from hydrogen or a halogen; and $R_{203}$, $R_{207}$ and $R_{208}$ are independently selected from hydrogen or an alkyl comprising 1 to 4 carbon atoms.

b) W, X, Y and Z form a heterocycle having the structure

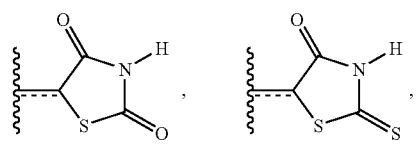

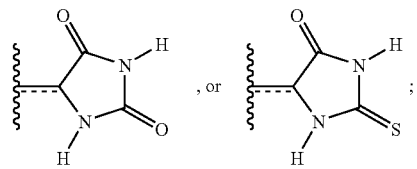

c) - - - is either present or absent;

d) $Ar_{10}$ has the structure

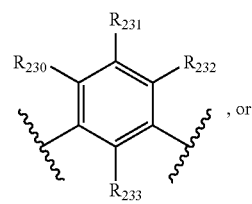, or

-continued

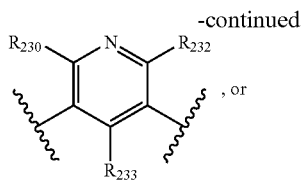

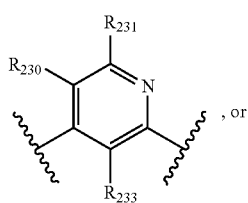

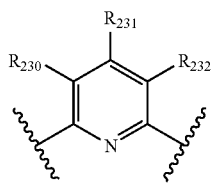

wherein $R_{230}$, $R_{231}$, $R_{232}$ and $R_{233}$ are independently selected from hydrogen, alkyl, haloalkyl, halogen, hydroxyl, acyloxy, amino, mono-substituted amino, di-substituted amino, acyl, alkoxy, haloalkoxy, thioalkyl, alkylsulfoxide, alkylsulfonyl, carboxy, carboalkoxy, alkylcarboxamide, or dialkylcarboxamide, with the proviso that $R_{230}$ is not hydrogen; and e) $R_{211}$ is hydrogen or an alkyl having from 1 to 4 carbon atoms;

or a pharmaceutically acceptable salt thereof.

In yet another embodiment, the invention relates to a compound having the structure

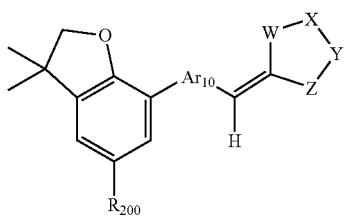

wherein:

a) $R_{200}$ comprises 1 to 10 carbon atoms and is selected from the group consisting of an alkyl, haloalkyl, halogen, cyano, nitro, hydroxyl, acyloxy, amino, monoalkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide;

b) W, X, Y and Z form a heterocycle having the structure

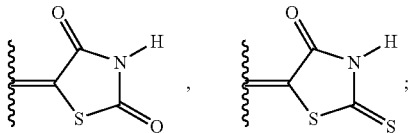

c) $Ar_{10}$ has the structure

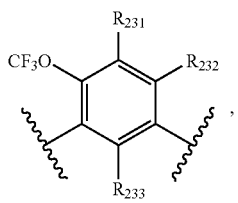

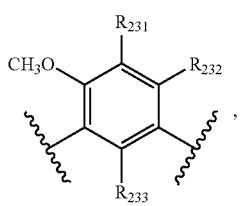

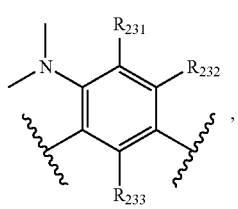

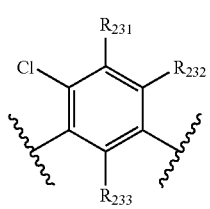

wherein $R_{231}$, $R_{232}$ and $R_{233}$ are independently selected from hydrogen or a halogen.

The compounds disclosed herein can exist in various tautomeric forms. For example, 2,4-thiazolidinedione-containing compounds disclosed herein can exist in the form of tautomers (324a), (324b) and (324c).

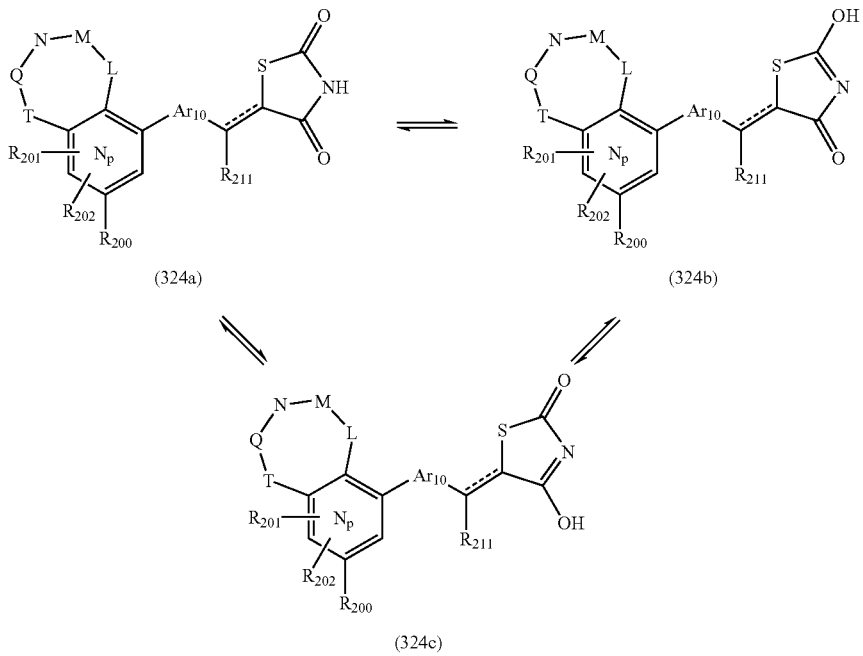

(324a)        (324b)

(324c)

It is understood by those skilled in the art that tautomers can also exist with compounds of the invention that contain the heterocycle 2-thioxo-thiazolidine-4-one, 2,4-imidazolidinedione or 2-thioxo-imidazolidine-4-one. For convenience, all of the tautomers can be presented herein by a single formula, but it is understood that all tautomers are within the scope of the invention.

When - - - is present both E and Z configurations are within the scope of the invention. For example, 2,4-thiazolidinedione and 2-thioxo-4-thiazolidinedione compounds of the invention can have the following structures respectively:

sodium or potassium; alkaline earth metals, such as calcium; and trivalent metals, such as aluminum. The only constraint with respect to the selection of the cation is that it should not unacceptably increase the toxicity.

As already noted above, the 5 membered heterocyclic ring radical comprising the W, X, Y, and Z groups form one of four heterocycles, selected from a 2,4-thiazolidinedione, 2-thioxo-thiazolidine-4-one, 2,4-imidazolidinedione or 2-thioxo-imidazolidine-4-one residue, which can be collectively termed "HAr" heterocycles. The four possible HAr heterocylic residues are shown in the drawing below:

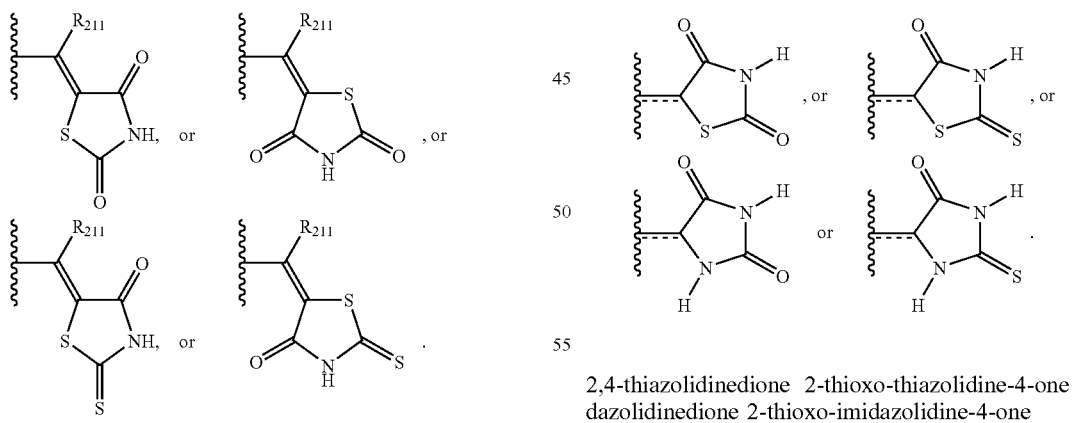

2,4-thiazolidinedione  2-thioxo-thiazolidine-4-one  2,4-imidazolidinedione  2-thioxo-imidazolidine-4-one All four of the HAr heterocycles shown above comprise at least one ring nitrogen atom bonded to a hydrogen atom. The nitrogen-bound hydrogen atoms of all four of the HAr heterocyles are sufficiently acidic so as to react with common laboratory bases such as organic amine compounds, hydroxide salts, and the like.

When only one of the two isomers is shown in this specification or in the claims, it should be presumed that both isomers and mixtures thereof are intended unless the context makes it plain that only a single isomer is intended.

The compounds disclosed herein can also include salts of the compounds, such as salts with cations. Cations with which the compounds of the invention can form pharmaceutically acceptable salts include alkali metals, such as The acidity of the four HAr heterocycles provides a ready method for preparing salts of the compounds of the invention, by reaction with an appropriate base, so as to generate an anion from the compound of the invention and a cation derived from the base employed. The salts formed by such reactions have the structure

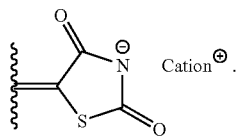

A wide variety of bases can be employed to produce such salts, including monovalent alkali metal hydroxides, divalent alkaline earth metal hydroxides, or bases comprising trivalent metal salts such as aluminum. Alternatively, organic bases such as primary, secondary, or tertiary amines can react with the acidic hydrogens of the compounds of the invention to form ammonium salts. The base and/or its associated cation can be chosen so as to provide desirable solubility, toxicity, and/or bioavailability characteristics in the salt after formation of the desired salts. The identity of the base and/or the resulting cation will of course vary somewhat with the identity of the compound of the invention, and the nature of the pharmaceutical composition to be employed and its physical form as a solid or liquid, and the nature of any solvents and/or carriers to be employed.

The United States Food and Drug Administration has published a list of pharmaceutically acceptable cations for pharmaceutically acceptable salts that includes aluminum, calcium, lithium, magnesium, potassium, sodium, and zinc cations, ammonium cations formed by the reactions of acidic compounds with benzathine, chloroprocaine, choline, diethanolamine, ethylenediamine, meglumine, procaine, t-butylamine, and tris(hydroxymethyl)aminomethane ("Tris"). Such "pharmaceutically acceptable" salts are often employed and/or evaluated for use in the invention simply because of the likelihood of decreased FDA regulatory scrutiny of Example 25 provides an example of the synthesis of a particularly useful "Tris" ammonium salt of one of the compounds of the invention.

Also, one or more compounds disclosed herein can include zwitterionic salts formed by reaction of a nitrogen contained internally within the compound, such as an amine, aniline, substituted aniline, pyridyl and like residues with the acidic hydrogen of the HAr group. Alternatively, a basic nitrogen contained internally within the compound can be reacted with an external acid, such as HCl, sulfuric acid, a carboxylic acid or the like.

The present invention provides, but is not limited to, the specific compounds set forth in the Examples.

Making Compounds of the Invention

Figure 4:
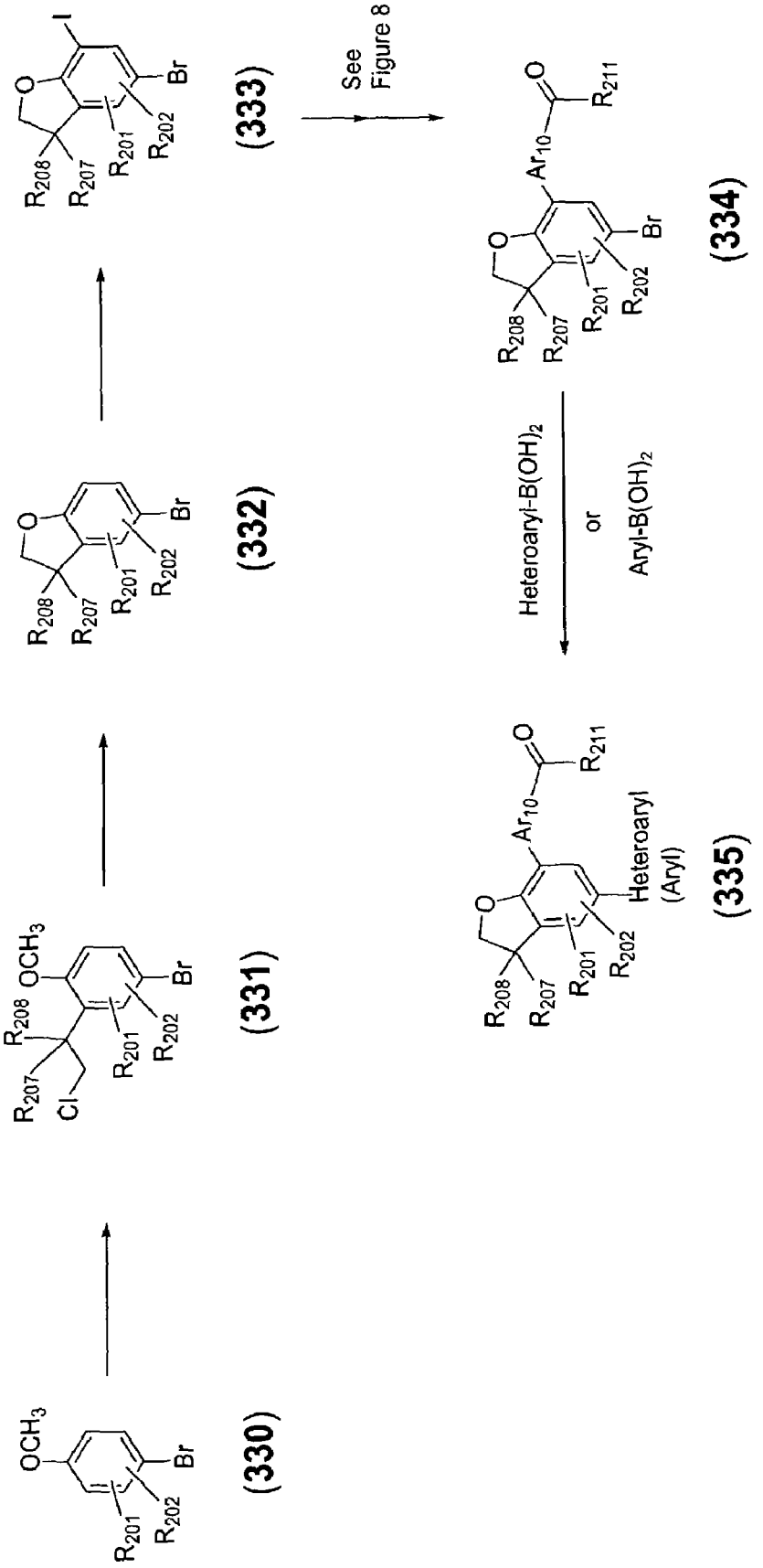
FIG. 4 shows examples of methods for synthesizing certain synthetic precursors of the dihydrobenzofuran compounds disclosed herein.

Various synthetic methods can be employed in the making of the compounds disclosed herein. A representative set of synthetic pathways is shown in FIGS. 4–7 for the making of the aryl group that can be used in the coupling with $Ar_{10}$ and subsequently to the compounds of Formula (300). One method, for example as shown in FIG. 4, includes the use of anisole (330) that can be alkylated with, for example, 3-chloro-2-methyl-propene, to give anisole (331). By selecting the desired chloro-propene the groups $R_{207}R_{208}$ can be introduced into compounds of the invention. Anisole (331) is subsequently cyclized in the presence of pyridine hydrochloride and quinoline with heat to give the dihydro-benzofuran (332). The dihydro-benzofuran (332) can be iodinated to compound (333) and subsequently coupled using methods described below herein to give biaryl (334). Different groups can be introduced at this stage in the synthesis. For example, biaryl (334) can undergo another coupling reaction, such as a Suzuki coupling reaction and other methods described herein below, to give biaryl (335) wherein different heteroaryls or aryl groups can be introduced as shown in FIG. 4.

Figure 5:
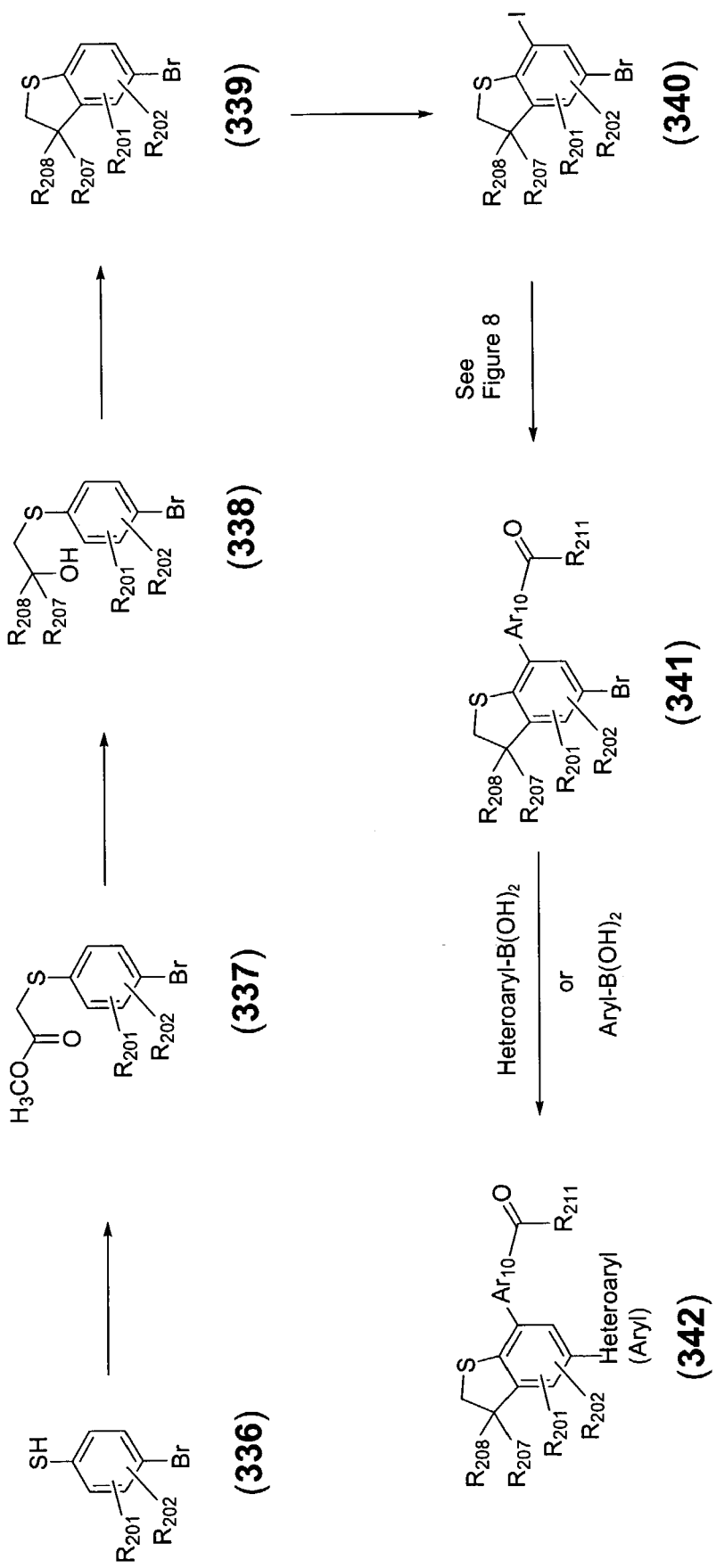
FIG. 5 shows examples of methods for synthesizing certain synthetic precursors of the dihydrobenzothiofuran compounds disclosed herein.

Another method, for example shown in FIG. 5, includes the use of aryl thiol (336) that can be alkylated with an alpha-halo acetate to give ester (337). The ester can be converted to a 3° alcohol (338) by methods known in the art, such as through a Grignard reagent. The groups $R_{207}R_{208}$ can be introduced into compounds of the invention by the selection of the appropriate Grignard. Alcohol (338) is cyclized using, for example, a Lewis acid, such as $AlCl_3$, to give dihydro-benzothiophene (339). In a similar manner as described above herein, dihydro-benzothiophene (339) can be iodinated to compound (340). Compound (340) can be converted to biaryl (341) and subsequently modified to biaryl (342). Coupling reactions to biaryls wherein a sulfur is present in the molecule can provide difficulties with certain catalyses. However, there are various procedures in the art that allow such couplings in the presence of a sulfur atom, such as, Cram, et al., *J. Org. Chem.* 55:4622–4634 (1990) and Savarin, et al., *Org. Letters* 3:2149–2152 (2001).

Figure 6:
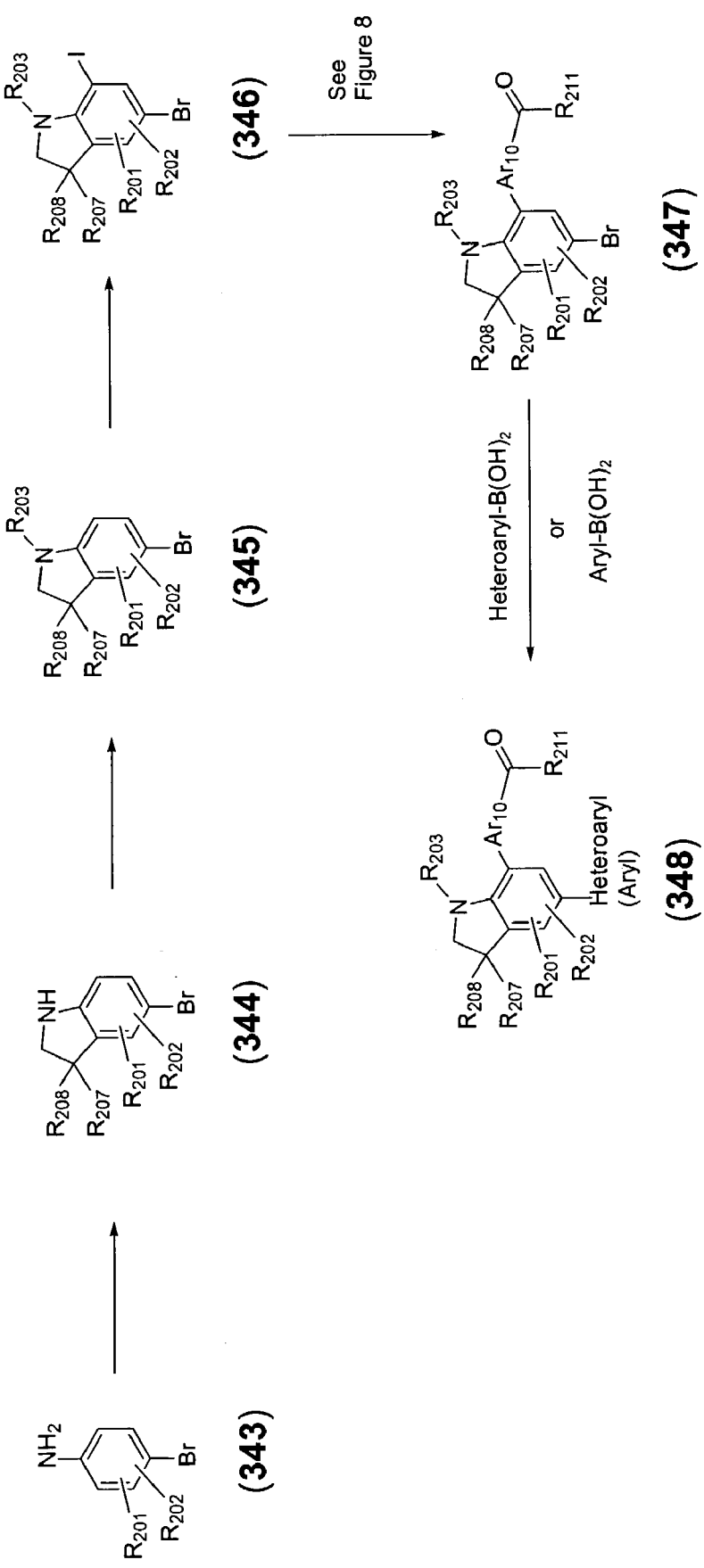
FIG. 6 shows examples of methods for synthesizing certain synthetic precursors of the dihydrobenzopyrrole compounds disclosed herein.

Another method, for example shown in FIG. 6, includes the use of aniline (343) that can be cyclized in a similar manner as described by Kraus, et al. *Tetrahedron Letters* 40:2039–2040 (1999) to give dihydro-indole (344). At this stage, $R_{203}$ can be introduced by allowing $R_{203}$-LG to react with the nitrogen anion of dihydro-indole (344), wherein LG is a leaving group, such as, for example, Cl, Br, I, OTf, and the like to give dihydro-indole (345). Dihydro-indole (345) can be iodinated to give dihydro-indole (346) and using methods described herein above dihydro-indole (346) is converted to biaryl (347) and subsequently into aryl or heteroaryl modified biaryl (348). It will be appreciated that biaryls (334), (341) and (347) can be converted into a boron derivative, such as a boron ester or boronic acid, and subsequently coupled with an aryl or heteroaryl halide to give the corresponding coupled biaryl (335), (342) and (348) respectively.

Figure 7:
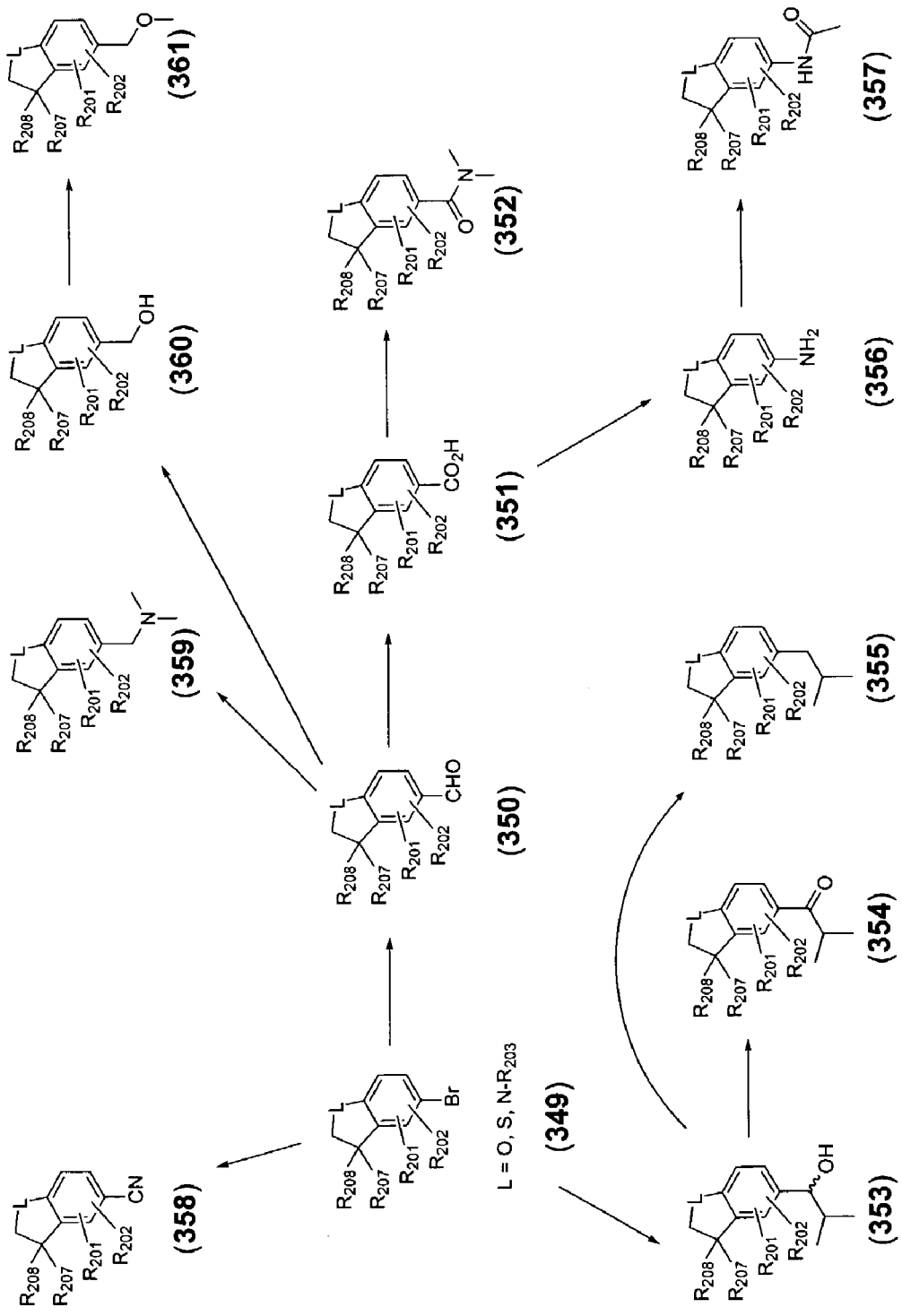
FIG. 7 shows examples of methods for introducing various types of R$_{200}$ substituents into synthetic precursors used to synthesize the compounds disclosed herein.

Another method, for example shown in FIG. 7, uses aryl bromide (349) to prepare a variety of $R_{200}$ groups. For example, aryl bromide (349) can be converted to aldehyde (350) through an aryl lithium intermediate and DMF or equivalent thereof. Aldehyde (350) can be oxidized using methods in the art, such as, $KMnO_4$ or similar oxidant, to give carboxylic acid (351). Carboxylic acid (351) can either be coupled with a variety of amines, such as, for example, dimethyl amine, to give amide (352) or allowed to undergo a Curtius Rearrangement to give aniline (356). Such rearrangements can be accomplished using, for example, diphenylphosphorylazide. Aniline (356) can be allowed to react with a variety of electrophiles such as, for example, acetyl choride to give amide (357). Aldehyde (350) can also under reductive amination with amines in the presence of reducing reagents, such as, for example, sodium cyanoborohydride, to give amine (359). Aldehyde (350) can also be reduced to give benzyl alcohol (360) and subsequently converted to ether (361) using a base and an alkyl-LG, wherein LG is a leaving group such as those described above herein. Aryl bromide (349) can also be converted into an aryl lithium intermediate, in a manner described above, and allow to react with an aldehyde or ketone, for example isobutyraldehyde, to give alcohol (353). Alcohol (353) can either be oxidized to ketone (354) or deoxygenated using, for example, triethylsilane in TFA, to give arylalkyl (355). Aryl bromide (349) can also be converted into benzonitrile (358) using methods known in the art, such as CuCN in quinoline with heat. Benzonitriles can be converted into a variety of heterocycles using methods known in the art.

Figure 8:
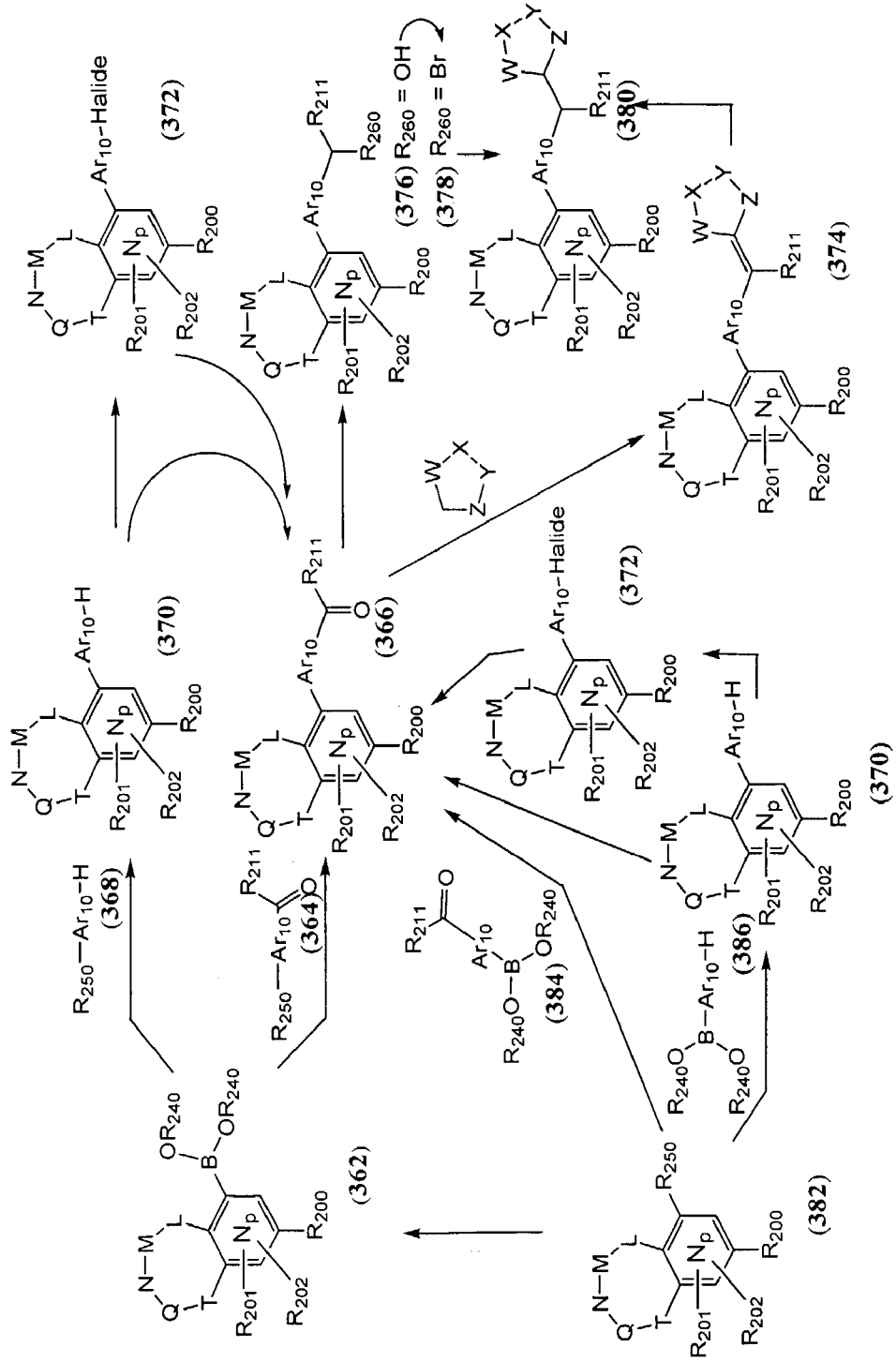
FIG. 8 shows examples of methods for coupling various synthetic precursors so as to synthesize the final product heterocycles disclosed herein.

Various synthetic methods can be employed in coupling the aryl or heteroaryl together with $Ar_{10}$ of Formula (300). A representative set of synthetic pathways is shown in FIG. 8. One method, for example, includes coupling a boronic acid of Formula (362), $R_{240}$=H, with a suitable carbonyl-containing aryl of Formula (364), such as $R_{250}$=Br, I, Cl, triflate or the like, to give biaryl (366) that is substituted with a carbonyl group, such as a formyl group (i.e., $R_{211}$=H). Alternatively, boronic acid (362) can be coupled with aryl (368), such as when $R_{250}$=Br, I, Cl, triflate or the like, to give biaryl (370) that is subsequently formylated using techniques known in the art, such as the Vilsmeier or the Vilsmeier-Haack reaction, the Gatterman reaction, the Duff reaction, the Reimer-Tiemann reaction or a like reaction. Coupling reactions such as that described for the formation of Biaryl (366) and (370) can also be conducted using boronic esters, such as where $R_{240}$ together with the boron from a pinacol borate ester (formation of pinacol esters: Ishiyama, T., et al., J. Org. Chem. 1995, 60, 7508–7510, Ishiyama, T., et al., Tetrahedron Letters 1997, 38, 3447–3450; coupling pinacol esters: Firooznia, F. et al., Tetrahedron Letters 1999, 40, 213–216, Manickam, G. et al., Synthesis 2000, 442–446; all four citations incorporated herein by reference). In the example for aryl (368) when $R_{250}$ is a triflate, it can easily be obtained by known methods from the corresponding phenol.

Biaryl (370) can also be acylated, for example by the Friedel-Crafts Acylation reaction (using an acid chloride) or the like to give biaryl (366) where $R_{211}$ is not hydrogen. Alternatively, in a two step manner, biaryl (370) is formylated by first performing a halogenation step to give biaryl (372), such as a bromination, followed by a halogen-metal exchange reaction using an alkyl lithium or lithium tributylmagnesate complex as described by Iida, et. al. in Tetrahedron Letters 2001, 42, 4841–4844 and reaction with DMF or equivalent known in the art to give biaryl (366) where $R_{211}$ is H.

In an alternative manner, the coupling can take place between aryl (382), such as where $R_{250}$=Br, I, Cl, triflate or the like, and boronic acid (384, $R_{240}$=H or alkyl) to give the above mention biaryl (366). Also aryl (382) can be coupled with boronic acid (386) to give biaryl (370). Employing the same strategy as described above biaryl (370) can be converted to biaryl (366).

Coupling of two aryl rings can be conducted using an aryl boronic acid or esters with an aryl halide (such as, iodo, bromo, or chloro), triflate or diazonium tetrafluoroborate; as described respectively in Suzuki, *Pure & Applied Chem.*, 66:213–222 (1994), Miyaura and Suzuki, *Chem. Rev.* 95:2457–2483 (1995), Watanabe, Miyaura and Suzuki, *Synlett.* 207–210 (1992), Littke and Fu, *Angew. Chem. Int. Ed.*, 37:3387–3388 (1998), Indolese, *Tetrahedron Letters*, 38:3513–3516 (1997), Firooznia, et. al., *Tetrahedron Letters* 40:213–216 (1999), and Darses, et. al., *Bull. Soc. Chim. Fr.* 133:1095–1102 (1996); all incorporated herein by reference.

According to this coupling reaction, precursors such as (362) and (364) can be employed:

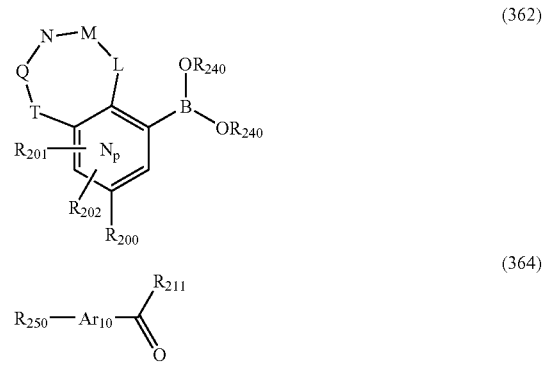

(362)

(364)

where $R_{240}$ is either alkyl, cycloalkyl (i.e., pinacol) or hydrogen and $R_{250}$ is a halide (such as, iodo, bromo, or chloro), triflate or diazonium tetrafluoroborate. Alternatively, it is understood that the coupling groups can be reversed, such as the use of (382) and (384), to achieve the same coupling product:

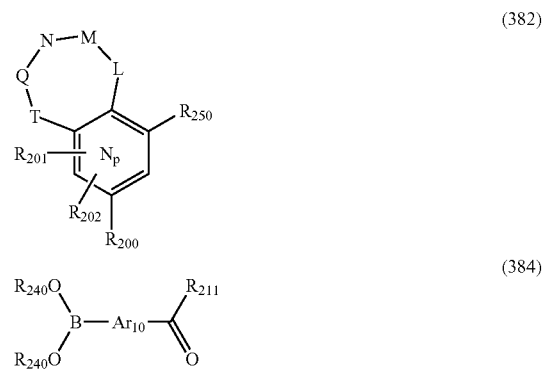

(382)

(384)

where $R_{240}$ and $R_{250}$ have the same meaning as described above. The preparation of the above mentioned precursors can be prepared by methods readily available to those skilled in the art. For example, the boronic ester can be prepared from aryl (382, where $R_{250}$=halide, such as bromo) by conversion of the halide to the corresponding aryl lithium, followed by treatment with a trialkyl borate. Methods are know in the art to prepare pinacol boronic esters from trflates, such as aryl (382, where $R_{250}$=triflate). The coupling reaction can also be conducted between an arylzinc halide and an aryl halide or triflate. Alternately, the coupling reaction can also be executed using an aryl trialkyltin derivative and an aryl halide or triflate. These coupling methods are reviewed by Stanforth, *Tetrahedron* 54:263–303 (1998) and incorporated herein by reference. In general, the utilization of a specific coupling procedure is selected with respect to available precursors, chemoselectivity, regioselectivity and steric considerations.

Condensation of the biaryl carbonyl containing derivatives (e.g., FIG. 8, compound (366)) with a suitable active methylene compound, such as, 2,4-thiazolidinedione, can be accomplished by the use of methods known in the art. For example, the biaryl carbonyl product from the coupling reaction can be condensed with an active methylene compound to give a benzylidene compound of Formula (300) (i.e., - - - is a bond) as described by Tietze and Beifuss, *Comprehensive Organic Synthesis* (Pergamon Press), 2:341–394, (1991), incorporated herein by reference. It is understood by those skilled in the art that intermediates having hydroxyl groups bonded thereto can be formed during condensation of a biaryl carbonyl containing derivative and an active methylene compound, as shown below.

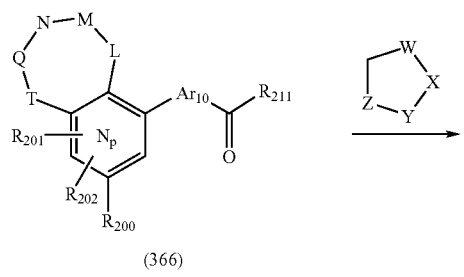

(366)

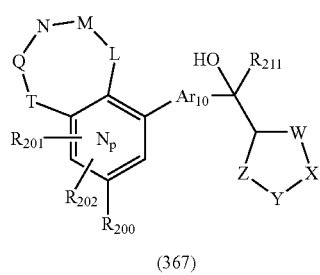

(367)

The hydroxyl groups of benzylic intermediates such as (367) are often eliminated (as water) during the condensation reaction, to form the desired benzylidene compound. Nevertheless, the conditions of the reaction can be modified for the isolation or further use of hydroxyl containing intermediates, and such embodiments are within the scope of the invention. Effective catalysts for the condensation can be selected from ammonia, primary, secondary and tertiary amines, either as the free base or the amine salt with an organic acid, such as acetic acid. Examples of catalysts include pyrrolidine, piperidine, pyridine, diethylamine and the acetate salts thereof. Inorganic catalysts can also be used for the condensation. Inorganic catalysts include, but are not limited to, titanium tetrachloride and a tertiary base, such as pyridine; and magnesium oxide or zinc oxide in an inert solvent system. This type of condensation can be strongly solvent-dependent and it is understood that routine experimentation may be necessary to identify the optimal solvent with a particular catalyst, preferable solvents include ethanol, tetrahydrofuran, dioxane or toluene; or mixtures thereof.

In order to prepare the reduced benzylic heterocycles such as compound (380), the carbonyl group of biaryl (366) can be reduced, such as with sodium borohydride, diisobutyl aluminum hydride, or the like, to give benzyl alcohol (376, $R_{260}$=OH) and converted to benzyl bromide (378, $R_{260}$=Br) with HBr or some other method known in the art, such as $PPh_3/CBr_4$ or converted to another leaving group, such as, for example, mesylate or iodide. Benzyl bromide (378, $R_{260}$=Br) or like compound is allowed to react with the anion(s) of precursors of HAr(1), HAr(2), HAr(3), or HAr (4), such as a deprotonated anion of 2,4-thiazolidinedione, to give a heterocyclic biaryl (380).

Alternatively, reduced benzylic biaryls of formula (380), can be prepared by a reduction of the benzylidene compound (374), using methods known in the art such as hydrogenation in the presence of Pd/C, Mg/MeOH, $LiBH_4$ in THF/pyridine and the like. A number of methods suitable for reducing benzylidene compounds to benzyl compounds (including hydrogenation, reaction with metal hydride reagents, or dissolving metal reductions) are known to those of skill in the art, and those methods can be applied in the methods of the instant invention.

Some of the compounds of the invention, comprise a "bicyclic" residue or radical of the following formula:

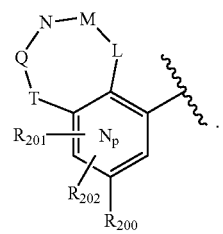

wherein the L, M, N, Q and T radicals or residues can be selected from —S—, —S(O)—, or —S(O)$_2$—. Compounds of formulas (305b) or (305e) are examples of such compounds comprising an —S— group. Such thioether compounds can be prepared from benzenethiol precursors, as will be apparent to those of ordinary skill in the art. The corresponding sulfoxides and sulfones can be readily prepared by selective oxidation of the thioether compounds. For example, appropriate thioether synthetic precursors can be oxidized in a selective manner with m-chloroperbenzoic acid to provide the sulfoxide compound. The sulfoxide can be further oxidized with additional m-chloroperbenzoic acid, or with hydrogen peroxide in acetic acid, as described by Zask et al., *J. Med. Chem.* 33:1418–1423 (1990), to provide the sulfone compounds, as is suggested below.

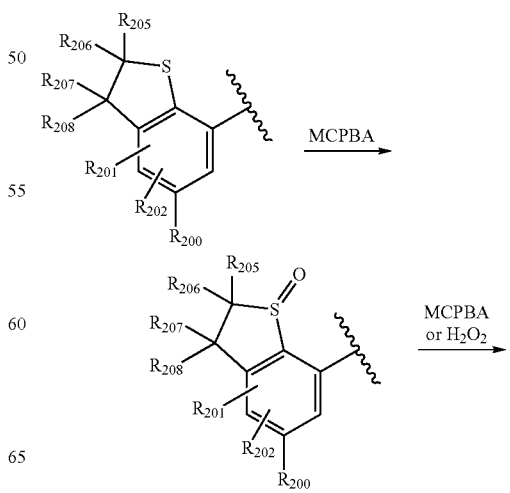

-continued

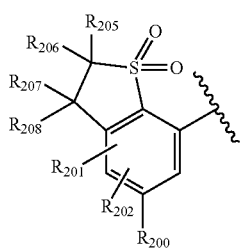

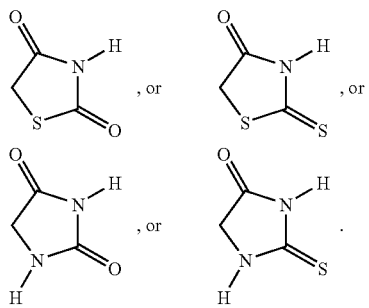

In view of the teachings and disclosures above, in some aspects, the invention relates to methods for preparing the compounds of the invention, wherein the method comprises a) coupling i) a bicyclic heterocycle precursor compound having the structure

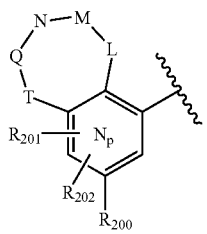

ii) with an $Ar_{10}$ precursor compound having the structure

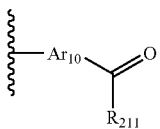

iii) to form a carbonyl containing precursor compound having the formula

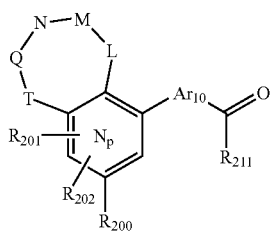

b) further reacting the carbonyl containing precursor compound so as to connect to the carbonyl of the carbonyl containing precursor the HAr heterocycle.

The methods of making the compounds of the invention can also comprise one or more additional steps, including a step wherein the further reacting comprises condensing the carbonyl containing precursor compound with a compound having the formula After the compounds of the invention have been prepared, it would be desirable for many applications of the compounds to prepare a pharmaceutically acceptable salt. Many methods for preparing pharmaceutically acceptable salts are well known to those of ordinary skill in the art. One method that can readily be employed to prepare such salts would be to react the compounds of the invention with a basic compound, such as a basic salt of a monovalent, divalent, or trivalent metal cation, or an organic amine, so as to remove an acidic hydrogen atom of the HAr group, so as to prepare a salt having the structure

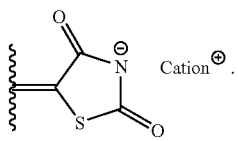

The cation obtained by such acid/base reactions would of course depend upon the nature of the base used to prepare the pharmaceutically acceptable salt. Suitable cations and/or bases have already been disclosed hereinabove in the disclosures related to the various embodiments of the active compounds themselves.

The various synthetic strategies and/or organic group transformations described hereinabove can be performed by a number of modified strategies and/or procedures other than those described above, as will be appreciated by those of ordinary skill in the art. References disclosing other synthetic procedures that can be utilized for the synthetic steps leading to the compounds disclosed herein can be found in, for example, March, J., *Advanced Organic Chemistry*, 4$^{th}$ *Edition*, Weiley-Interscience (1992); or Larock, R. C., *Comprehensive Organic Transformations, A Guide to Functional Group Preparations*, VCH Publishers, Inc. (1989), both incorporated herein in their entireties by this reference.

Pharmaceutical Compositions

Although the compounds described herein can be administered as pure chemicals, it is often preferable to present the active ingredient as a pharmaceutical composition. Thus additional embodiments of the invention relate to the use of a pharmaceutical composition comprising one or more compounds and/or one or more pharmaceutically acceptable salts thereof, together with one or more pharmaceutically acceptable carriers thereof and, optionally, other therapeutic and/or prophylactic ingredients. The carrier(s) must be 'acceptable' in the sense of being compatible with the other ingredients of the composition and not overly deleterious to the recipient thereof.

Pharmaceutical compositions include those suitable for oral, enteral, parental (including intramuscular, subcutaneous and intravenous), topical, nasal, vaginal, ophthalinical, sublingually or by inhalation administration. The compositions can, where appropriate, be conveniently presented in discrete unit dosage forms and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art., e.g., with enteric coatings.

Oral liquid preparations can be, in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The compounds can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

For topical administration to the epidermis, the compounds can be formulated as ointments, creams or lotions, or as the active ingredient of a transdermal patch. Suitable transdermal delivery systems are disclosed, for example, in Fisher et al. (U.S. Patent (U.S. Pat. No. 4,788,603, incorporated herein by reference) or Bawas et al. (U.S. Pat. Nos. 4,931,279, 4,668,504 and 4,713,224; all incorporated herein by reference). Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842; incorporated herein by reference.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention can also contain other adjuvants such as flavorings, coloring, antimicrobial agents, or preservatives.

Biological Activity of the Compounds

The compounds of the present invention have been found to be active in a number of biological assays, both in vitro and in vivo, that correlate to, or are representative of, human diseases.

In-Vitro Screening for Adipocyte Differentiation. The compounds of the invention can induce the differentiation of preadipocytes into adipocytes. Once preadipocytes become differentiated, they tend to accumulate lipids, and the increasing lipid content of the differentiated cells can be readily detected. This activity (Harris and Kletzien, *Mol. Pharmacol.*, 45:439–445 (1994); Willson et al., *J. Med. Chem.* 39:665–668 (1996)) has been observed for certain compounds that have antidiabetic activity in humans (Teboul et al., *J. Biol. Chem.* 270:28183–28187 (1995)), and assays for adipocyte diffentiation activity have been employed by those in the art to screen new compounds for anti-diabetic activity.

As illustrated in Example 21 and FIG. 1, a number of the compounds whose synthesis is detailed in Examples 1–19 were found to induce the differentiation of 3T3-L1 pre-adipocytes in in-vitro tests, when applied at concentrations of $1 \times 10^{-6}$ Molar and lower. For comparative purposes only, FIG. 1 shows the comparative adipocyte differentiation activity of compound 20 (5-[3-(3,5,5,8,8-Pentamethyl-5,6,7,8-tetrahydro-naphthalen-2-yl)-4-trifluoromethoxy-benzylidene]-thiazolidine-2,4-dione, which was disclosed as active for both adipocyte differentiation and for the treatment of diabetes in U.S. Pat. No. 6,515,003). As can be seen in FIG. 1, a number of the bicyclic compounds of the invention have adipocyte differentiation activity that is at least comparable to that of comparative compound 20.

Therefore, one method for assaying the biological activity of the compounds of the invention is conduct an assay as described in Example 21, and any compound that induces adipocyte differentiation at a concentration of less than or equal to about $1 \times 10^{-6}$ M, can be considered to have biological activity that is related to potential treatment of diabetes and/or related disorders of carbohydrate and/or lipid metabolism. In order to demonstrate the activity of the various compounds of the invention for effectiveness and/or activity for adipocyte differentiation, the compound can be applied at a concentration of about $1 \times 10^{-6}$ M for a period of about 7 days, to mouse preadipocyte 3T3-L1 cells, and measure the increase the lipid content of the cells. The compounds can be considered active for adipocyte differentiation if the lipid accumulation induced is at least about 20%, or at least about 40%, of the lipid accumulation induced by 5-[3-(3,5,5,8,8-Pentamethyl-5,6,7,8-tetrahydro-naphthalen-2-yl)-4-trifluoromethoxy-benzylidene]-thiazolidine-2,4-dione when it is applied to control cultures of mouse preadipocyte 3T3-L1 cells at a concentration of about $1 \times 10^{-7}$ M.

In-Vivo Screening for Biological Activity Using Mouse Models of Human Diseases The ability of the compounds to function as antidiabetic molecules and/or modulators of carbohydrate and/or lipid metabolism can be demonstrated in animal models. These models include among others, db/db mice, ob/ob mouse, and KKA$^y$ mice. Accordingly, the biological activity of the compounds of the invention has been demonstrated in experiments employing the KKA$^y$ mouse. A procedure for such experiments was described in detail in Iwatsuka, et al., 1970 General Survey of Diabetic Features of Yellow KK Mice. *Endocrinol. Japon.* 17: 23–35, incorporated herein by reference. The testing of the compounds of the invention was conducted as described in Example 22. The animals were treated with a single daily oral dose of 15 mg/kg of the test compound suspended in sesame oil (dose volume of 3–5 ml/kg). At the end of one and two weeks of treatment the animals were bled from the tail vein and their serum glucose and triglycerides and/or cholesterol was measured in duplicate.

Figure 2:
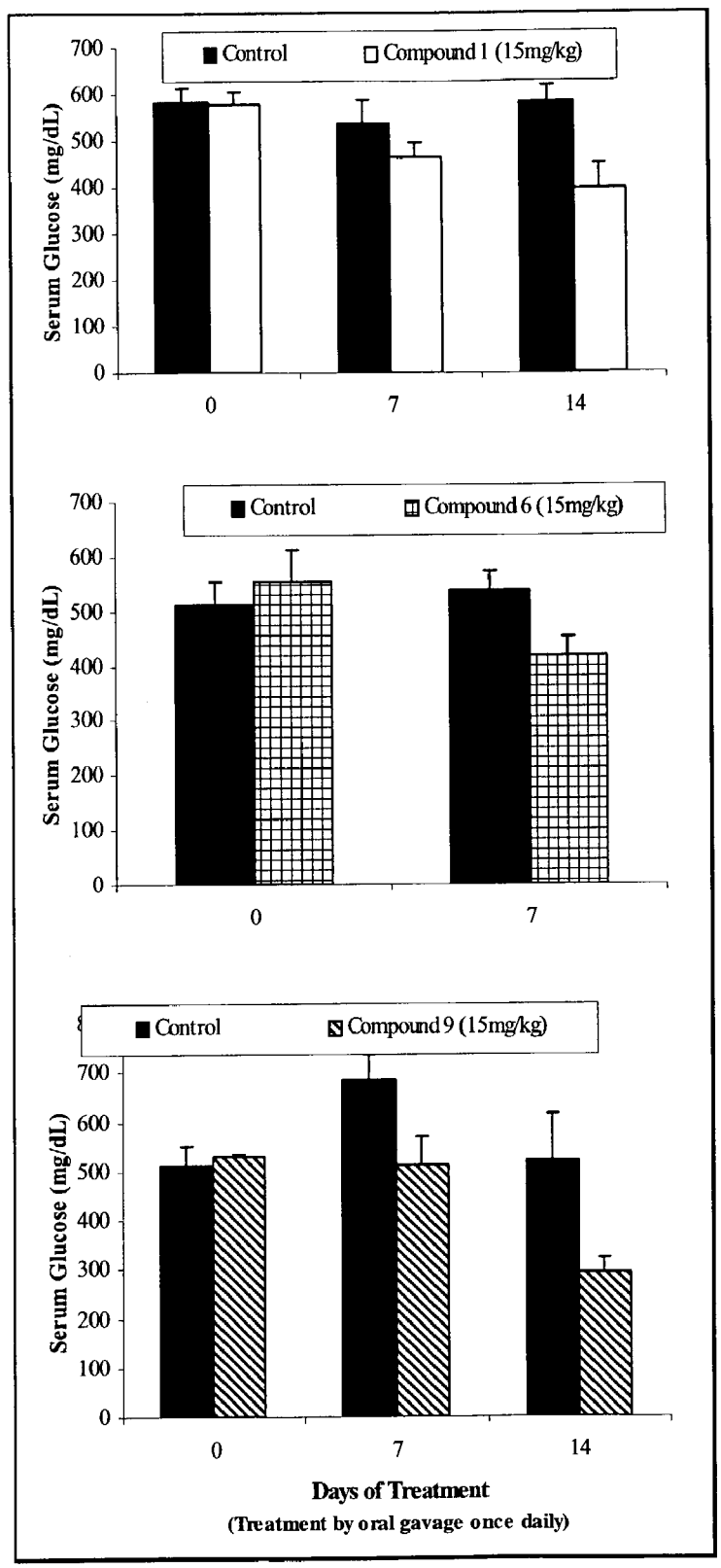
FIG. 2 shows the serum glucose lowering activity of the compounds of the present invention in the KKA$^y$ Mouse Model.
Figure 3:
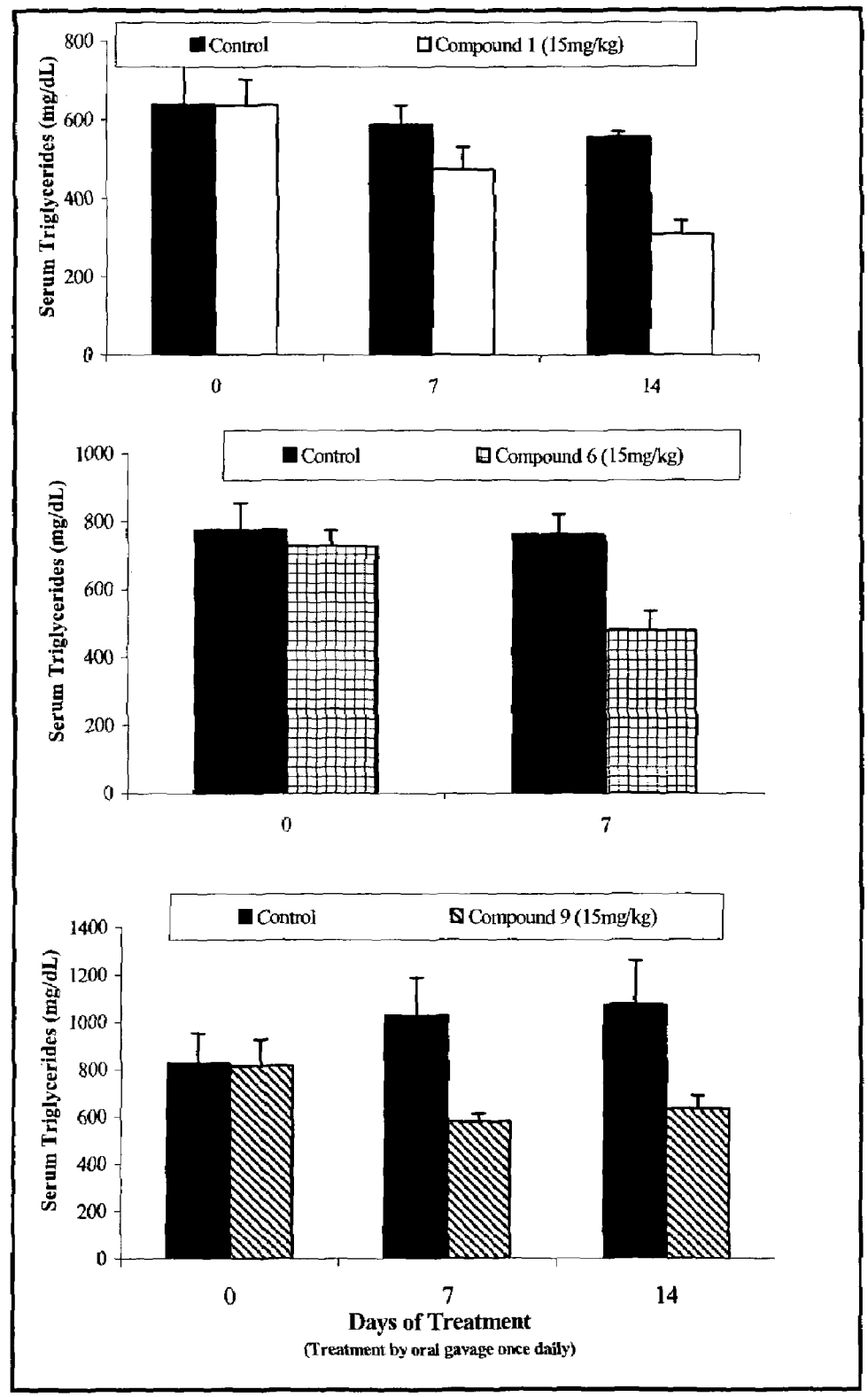
FIG. 3 shows the serum triglyceride lowering activity of the compounds of the present invention in the KKA$^y$ Mouse Model.

The results of the testing of compounds 1, 6, and 9 of the invention are shown in FIGS. 2 and 3. As can be seen in FIG. 2, all three compounds significantly lowered the serum glucose level of the treated rats, as compared to a control. Unexpectedly, as can be seen in FIG. 3, all three compounds simultaneously lowered the serum triglyceride levels of the treated animals as compared to a control. The simultaneous decrease of both serum glucose and serum triglycerides in the animals was particularly unexpected and surprising in view of the known tendency of certain already approved drugs for the treatment of diabetes to aggravate problems related to lipid metabolism.

In view of these experiments in the KKA$^y$ mice, the compounds of the invention have demonstrated oral bioavailability. Oral bioavailability allows for oral dosing for use in chronic diseases such as diabetes, with the advantage of self-administration and decreased cost over other means of administration.

Compounds showing efficacy in lowering serum glucose and which do not increase serum triglycerides, or preferably, compounds that simultaneously lower glucose and triglyceride levels in the KKA$^y$ mouse model, can be further tested in additional in vivo model animals known in the art, such as those involving, db/db, ob/ob, and Sprague Dawley rats. The ability of a compound to reduce certain lipids such as cholesterol or to change the ratio of good versus bad cholesterol, i.e. HDL versus LDL, can be measured in animal models. One model commonly used is the diet-induced hypercholesterolemic Sprague Dawley rat.

Methods for Treating Diseases

The compounds described herein can be used effectively to prevent, alleviate or otherwise treat type 2 diabetes and/or related disease states in mammals, including humans. As is well known, type 2 diabetes is related to deficiencies in carbohydrate metabolism. Patients suffering from type 2 diabetes usually still produce insulin, which is directly involved in carbohydrate metabolism, but become increasingly resistant to their own insulin and to insulin therapy. The deficiencies in carbohydrate metabolism cause damaging increases in serum glucose concentration, causing potentially deadly side effects and/or damage general metabolism and/or vital organs.

Methods of treatment comprising the administration of the compounds of the invention to an animal such a diabetic patient beneficially modulate carbohydrate metabolism. Carbohydrate metabolism can be up-regulated or down-regulated to either approach the level of carbohydrate metabolism in the animal or as compared to a control animal, or to deviate from the level of carbohydrate metabolism in an animal or as compared to a control animal.

Therefore, in some embodiments, the invention relates to methods for treating type 2 Diabetes comprising administering to an animal, a mammal, or a human diagnosed as needing such treatment one or more compounds of the invention in an amount effective to decrease the serum glucose levels of the animal, mammal, or human. In some embodiments of the methods the compound is applied in an amount effective to decrease the serum glucose levels in the animal, mammal, or human by at least about 5%, or about 10%.

Changes in carbohydrate metabolism can directly or indirectly also result in changes of lipid metabolism and, similarly, changes in lipid metabolism can lead to changes in carbohydrate metabolism. For example, in type 2 diabetes an increase in free fatty acids in the patients leads to decreased cellular uptake and metabolism of glucose.

Accordingly, the present invention also relates to methods for modulating lipid metabolism that relate to administration of a compound of the invention to an animal, mammal, or human so as to induce an increase of lipid content intracellular or extracellularly. For example, compounds of the invention can induce macrophages to increase secretion of cholesterol into the extracellar medium. Cholesterol-loaded macrophage foam cells are a hallmark of atherosclerotic lesions [Gown et al. (1986) Am. J. Phathol. 125, 191–207]. Although advanced human atherosclerotic lesions contain other cell types, it has been suggested that the lipid-rich portion of the lesion is most prone to rupture and cause myocardial infarction (Ross, 1999). Removal of cholesterol from peripheral cells including macrophages, is a key process in the maintenance of whole body cholesterol homeostasis and prevention of atherosclerosis [Oram, J. F. (2002) Trends Mol.Med. 8, 168–173]. This process involves efflux of excess cholesterol from peripheral cells towards nascent high density lipoprotein (HDL), followed by transport of the cholesterol to the liver, followed by hepatic uptake and secretion in the form of cholesterol or bile salt, and finally disposal into feces. Therefore, novel therapeutic agents that increase cholesterol efflux from macrophages in atherosclerotic lesions can be employed to treat patients with coronary artery disease, which is a disease that is often associated with diabetes.

Modulation of lipid metabolism by the compounds of the invention can also induce a decrease of lipid content intracellularly or extracellularly. Modulation of metabolism can occur directly for example, through binding of the compound of the invention with its cognate receptor, which directly affects an increase or decrease in serum lipid content by up-regulation or down-regulation of a gene involved in lipid metabolism. Modulation of metabolism can also occur indirectly, for example, through binding of the compound of the invention with its cognate receptor, which up-regulates or down-regulates cellular differentiation or growth of cells that produce lipids, thereby indirectly causing lipid metabolism to be modulated. Modulation, also includes, for example, an increase in lipid metabolism, such that the lipid metabolism approaches that of a control. Likewise, modulation of lipid metabolism could be a decrease in the rate of lipid metabolism, such that the rate of lipid metabolism is less than or decreasing towards a control.

It is also to be understood that a variety of lipid molecules can be modulated. The compounds disclosed herein can modulate a single class of lipid molecules, such as triglycerides. Therefore, in some embodiments, the invention relates to methods for treating dyslipidemia comprising administering to an animal, a mammal, or a human diagnosed as needing such treatment one or more compounds of the invention in an amount effective to decrease serum triglyceride levels in the animal, mammal, or human, or as compared to serum triglyceride levels in control animals, mammals, or humans. In some embodiments, the compounds of the invention are administered in an amount effective to decrease serum triglyceride levels by at least about 5%, or at least about 10%.

The compounds disclosed herein can also modulate multiple classes of lipid molecules, including cholesterol. Therefore, in some embodiments the invention relates to a method of treating hypercholesterolemia comprising administering to an animal, mammal, or human diagnosed as needing such treatment one or more compounds of the invention in an amount effective to treat the hypercholesterolemia. In some embodiments, the one or more compounds is applied in an amount effective to decrease serum cholesterol levels in the animal, mammal, or human, or as compared to a control animal, mammal, or human by at least about 5%, or at least about 10%.

Surprisingly and quite unexpectedly, the methods of treatment that employ compounds of the invention for the treatment of diabetes have been shown to simulultaneously decrease both serum glucose and serum triglyceride levels in animal models for diabetes.

The compounds disclosed herein can be either used singularly or plurally, and pharmaceutical compositions thereof for the treatment of mammalian diseases, particularly those related to humans. Compounds disclosed herein and compositions thereof can be administered by various methods including, for example, orally, enterally, parentally, topically, nasally, vaginally, ophthalinically, sublingually or by inhalation for the treatment of diseases related to lipid metabolism, carbohydrate metabolism, lipid and carbohydrate metabolism such as polycystic ovary syndrome, syndrome X, type 2 diabetes, including disorders related to type 2 diabetes such as, diabetic retinopathy, neuropathy, macrovascular disease or differentiation of adipocytes. Routes of administration and doseages known in the art can be found in *Comprehensive Medicinal Chemistry, Volume* 5, Hansch, C. Pergamon Press, 1990; incorporated herein by reference.

The compositions can also be used as regulators in diseases of uncontrolled proliferation. The composition can be useful in the treatment of polycystic kidney disease and cancers such as, carcinomas, lymphomas, leukemias, and sarcomas. A representative but non-limiting list of cancers is lymphoma, Hodgkin's Disease, myeloid leukemia, bladder cancer, brain cancer, head and neck cancer, kidney cancer, lung cancers such as small cell lung cancer and non-small cell lung cancer, myeloma, neuroblastoma/glioblastoma, ovarian cancer, pancreatic cancer, prostate cancer, skin cancer, liver cancer, melanoma, colon cancer, cervical carcinoma, breast cancer, and epithelial cancer. Compounds disclosed herein can be used for the treatment of inflammatory diseases such as osteoarthritis, rheumatoid arthritis, Crohn's Disease, pulmonary fibrosis, and Inflammatory Bowel Disease.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, one of skill in the art understands how to extrapolate in vivo data obtained in a model organism, such as a $KKA^y$ mouse, an ob/ob or db/db mouse, to another mammal, such as a human. These extrapolations are not simply based on the weights of the two organisms, but rather incorporate differences in metabolism, differences in pharmacological delivery, and administrative routes. Based on these types of considerations, a suitable dose will, in alternative embodiments, typically be in the range of from about 0.5 to about 100 mg/kg/day, or from about 1 to about 75 mg/kg of body weight per day, or from about 3 to about 50 mg per kilogram body weight of the recipient per day.

The compound is conveniently administered in unit dosage form; for example, in alternative embodiments, containing 0.5 to 1000 mg, 5 to 750 mg, most conveniently, or 10 to 500 mg of active ingredient per unit dosage form.

One skilled in the art will recognize that dosage and dosage forms outside these typical ranges can be tested and, where appropriate, be used in the methods of this invention.

In separate embodiments, the active ingredient can be administered to achieve peak plasma concentrations of the active compound of from about 0.5 to about 75 µM, about 1 to 50 µM, or about 2 to about 30 µM. This can be achieved, for example, by the intravenous injection of a 0.05 to 5% solution of the active ingredient, optionally in saline, or orally administered as a bolus containing about 0.5–500 mg of the active ingredient. Desirable blood levels can be maintained by continuous infusion to provide about 0.01–5.0 mg/kg/hr or by intermittent infusions containing about 0.4–15 mg/kg of the active ingredients.

The desired dose can conveniently be presented in a single dose or as divided doses administered at appropriate intervals, for example, as two, three, four or more sub-doses per day. The sub-dose itself can be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as can be applied to the essential features hereinbefore set forth, and as follows in the scope of the appended claims.

The following examples are given to illustrate the invention and are not intended to be inclusive in any manner.

EXAMPLES

Example 1

5-[3-(5-Isobutyl-3,3-dimethyl-2,3-dihydro-benzofuran-7-yl)-4-trifluoromethoxy-benzylidene]-thiazolidine-2,4-dione, which can be Referred to as "Compound 1."

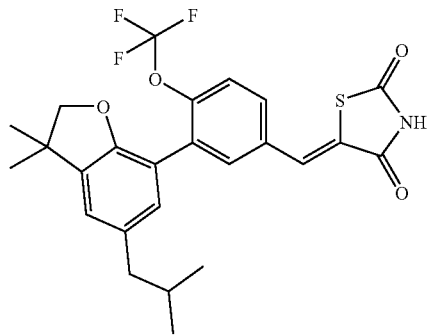

A mixture of toluene (35 mL), piperidine (145 μL), acetic acid (145 μL), 3-(5-isobutyl-3,3-dimethyl-2,3-dihydro-benzofuran-7-yl)-4-trifluoromethoxy-benzaldehyde (5.7 g, 14.53 mmol) and 2,4-thiazolidinedione (1.7 g, 14.53 mmol) was heated at reflux for 20 hrs. The reaction mixture was cooled to room temperature, diluted with ethyl acetate, washed with water and brine, dried over MgSO$_4$, filtered and evaporated. The residue was chromatographed on silica gel (0 to 20% ethylacetate in hexane) and further recrystallised from ethanol/water to afford 5.15 g (72%) of 5-[3-(5-Isobutyl-3,3-dimethyl-2,3-dihydro-benzofuran-7-yl)-4-trifluoromethoxy-benzylidene]-thiazolidine-2,4-dione. mp 142–146° C. $^1$H-NMR (300 MHz, DMSO-d-6): 0.87 (d, J=6.9 Hz, 6H), 1.31 (s, 6H), 1.81 (m, 1H), 2.44 (d, J=6.9 Hz, 2H), 4.19 (s, 2H), 6.91 (d, J=1.5 Hz, 1H), 7.07 (d, J=1.5 Hz, 1H), 7.58 (d, J=8.4 Hz, 1H), 7.70 (dd, J$_1$=8.4 Hz, J$_2$=2.4 Hz, 1H), 7.75 (d, J=2.1 Hz, 1H), 7.86 (s, 1H), 12.70 (br s, 1. The intermediate 3-(5-isobutyl-3,3-dimethyl-2,3-dihydro-benzofuran-7-yl)-4-trifluoromethoxy-benzaldehyde was prepared as follows:

a. 3-(5-isobutyl-3,3-dimethyl-2,3-dihydro-benzofuran-7-yl)-4-trifluoromethoxy-benzaldehyde.

A mixture of 3-bromo-4-trifluoromethoxy benzaldehyde (example 1h) (4.24 g, 15.75 mmol), 5-isobutyl-3,3-dimethyl-2,3-dihydro-benzofuran-7-boronic acid (4.3 g, 17.33 mmol) and potassium carbonate (4.35 g, 31.5 mmol) in toluene (39 mL), ethanol (7.5 mL) and water (2.5 mL) was degassed with argon for 15 minutes.

Tetrakis(triphenylphosphine)palladium(0) (0.728 g, 0.63 mmol) was added and the mixture heated at reflux under argon for 20 hrs. The solution was cooled to room temperature, diluted with ethyl acetate and washed successively with water and brine, dried over anhydrous magnesium sulfate, filtered and evaporated. The residue was purified on silica gel (0 to 5% ethyl acetate in hexane) to give 5.76 g of 3-(5-isobutyl-3,3-dimethyl-2,3-dihydro-benzofuran-7-yl)-4-trifluoromethoxy-benzaldehyde (93%).

$^1$H NMR (300 MHz; CDCl$_3$): 0.92 (d, J=6.9 Hz, 6H), 1.36 (s, 6H), 1.84 (m, 1H) 2.47 (d, J=7.5 Hz, 2H), 4.22 (s, 2H), 6.92 (d, J=4.8 Hz, 2H), 7.46 (dd, J=1.5 Hz and 8.7 Hz, 1H), 7.90 (dd, J=2.1 Hz and 8.7 Hz, 1H), 8.03 (d, J=2.1 Hz, 1H), 10.03 (s, 1H).

b. 5-isobutyl-3,3-dimethyl-2,3-dihydro-benzofuran-7-boronic acid.

To a mixture of 7-bromo-5-isobutyl-3,3-dimethyl-2,3-dihydro-benzofuran (9.9 g, 34.96 mmol) in THF (50 mL) cooled to −78° C. under an atmosphere of argon was added n-BuLi (25.17 mL, 2.5 M, 62.93 mmol) dropwise. The reaction mixture was stirred for 5 minutes and triisopropylborate (24.2 mL, 104.87 mmol) was added dropwise. The mixture was stirred at −50° C. for 2 hours then warmed up to room temperature and stirred overnight at room temperature. 1.0 N HCl (100 mL) was slowly added to the reaction mixture. After 1 hour the mixture was diluted with ethyl acetate and the layers separated. The organic layer was further washed with water, brine, dried (MgSO$_4$), filtered and evaporated. The residue was chromatographed on silica gel (0 to 20% ethyl acetate in hexane) to give 4.3 g of 5-isobutyl-3,3-dimethyl-2,3-dihydro-benzofuran-7-boronic acid (46%). $^1$H NMR (300 MHz; CDCL$_3$): 0.90 (d, J=6.6 Hz, 6H), 1.33 (s, 6H), 1.81 (m, 1H), 2.43 (d, J=7.5 Hz, 2H), 4.28 (s, 2H), 5.86 (br s, 2H), 6.98 (d, J=2.1 Hz, 1H), 7.33 (d, J=2.1 Hz, 1H).

c. 7-bromo-5-isobutyl-3,3-dimethyl-2,3-dihydro-benzofuran.

To a solution of 5-isobutyl-3,3-dimethyl-2,3-dihydro-benzofuran (1.59 g, 7.78 mmol) in dichloromethane (40 mL) was added pyridinium tribromide (2.49 g, 7.78 mmol) and the reaction mixture stirred at room temperature overnight. The solution was washed with water and brine, dried (MgSO$_4$), filtered and evaporated. The residue was purified on silica gel (0% to 2% ethyl acetate in hexane) to give 1.51 g of 7-bromo-5-isobutyl-3,3-dimethyl-2,3-dihydro-benzofuran (68%). $^1$H NMR (300 MHz; CDCl$_3$): δ 0.90 (d, J=6.3 Hz, 6H), 1.33 (s, 6H), 1.77 (m, 1H), 2.39 (d, J=7.5 Hz, 2H), 4.30 (s, 2H), 6.80 (d, J=1.5 Hz, 1H), 7.05 (d, J=1.5 Hz, 1H).

d. 5-isobutyl-3,3-dimethyl-2,3-dihydro-benzofuran.

To a cold solution (0° C.) of 1-(3,3-dimethyl-2,3-dihydro-benzofuran-5-yl)-2-methyl-propan-1-ol (1.97 g, 8.93 mmol) in dry dichloromethane (40 mL) was added triethylsilane (2.85 mL, 17.86 mmol). After 10 minutes, trifluoroacetic acid was added and the reaction mixture stirred at 0° C. for 30 minutes. Water was poured into the reaction mixture and the layers separated. The organic layer was further washed with water, aqueous NaHCO$_3$ and brine, dried (MgSO$_4$), filtered and evaporated. The residue was purified on silica gel (0% to 5% ethyl acetate in hexane) to give 1.6 g of 5-isobutyl-3,3-dimethyl-2,3-dihydro-benzofuran (87%). $^1$H NMR (300 MHz; CDCl$_3$): δ 0.90 (d, J=6.3 Hz, 6H), 1.32 (s, 6H), 1.79 (m, 1H), 2.40 (d, J=6.9 Hz, 2H), 4.20 (s, 2H), 6.68 (dd, J=1.2 Hz and 7.5 Hz, 1H), 6.87 (m, 2H).

e. 1-(3,3-dimethyl-2,3-dihydro-benzofuran-5-yl)-2-methyl-propan-1-ol.

To a solution of 5-bromo-3,3-dimethyl-2,3-dihydro-benzofuran (2.03 g, 8.93 mmol) in dry THF (10 mL) at −78° C., under argon, was added dropwise n-BuLi (1.6 M in hexane, 13.4 mmol, 8.38 mL). The mixture was stirred for 5 minutes then isobutyraldehyde (1.22 mL, 8.38 mmol) was added and the mixture was slowly warmed up to room temperature and stirred overnight at room temperature. Aqueous ammonium chloride was added and the solution extracted with ethylacetate and the organic extract was dried (MgSO$_4$), filtered and evaporated. The residue was purified on silica gel (0% to 20% ethyl acetate in hexane) to give 1.97 g of 1-(3,3-dimethyl-2,3-dihydro-benzofuran-5-yl)-2 -methyl-propan-1-ol(100%). $^1$H NMR (300 MHz; CDC1$_3$): δ0.77(d, J=6.6 Hz, 3H), 0.90 (d, J=6.6 Hz, 3H), 1.33 (s, 6H), 1.95 (m, 1H), 4.23 (s, 2H), 4.28 (d, J=7.2 Hz, 2H), 6.72 (d, J=8.4 Hz, 1H), 7.03 (dd, J=8.1 Hz and 1.8 Hz, 1H), 7.06 (d, J=1.5 Hz, 1H).

f. 5-bromo-3,3-dimethyl-2,3-dihydro-benzofuran.

A mixture of 4-bromo-2-(2-chloro-1,1-dimethyl-ethyl)-1-methoxy-benzene (65 g, 0.234 mol), pyridine hydrochloride (121.8 g, 1.054 mol) and quinoline (110.67 mL, 0.936 mol) was refluxed at 164° C.–167° C. under argon for 5 hrs. After cooling to room temperature the reaction mixture was treated with ice-cold 6N HCl and extracted twice with ether. The organic layers were combined, dried (MgSO$_4$), filtered and evaporated. The residue was purified on silica gel (10% ethyl acetate in hexane) to give 52 g of 5-bromo-3,3-dimethyl-2,3-dihydro-benzofuran (98%). $^1$H NMR (300 MHz; CDCl$_3$): δ 1.32 (s, 6H), 4.23 (s, 2H), 6.67 (d, J=8.1 Hz, 1H), 7.19 (m, 2H).

g. 4-bromo-2-(2-chloro-1,1-dimethyl-ethyl)-1-methoxy-benzene.

Sulfuric acid (2 mL, 0.033 mol) was added dropwise under argon to 4-bromoanisole (14.6 mL, 0.117 mol). The mixture was warmed to 40–43° C. (warm water bath) and 3-chloro-2-methyl propene was added dropwise in 4 equal portions over 2 hrs. After 2 hrs at 40–43° C. the solution was diluted with dichloromethane and washed successively with water, saturated aqueous NaHCO$_3$, water and brine, dried (MgSO$_4$), filtered and evaporated. The residue was crystallized from hexanes to give 14.1 g of 4-bromo-2-(2-chloro-1,1-dimethyl-ethyl)-1-methoxy-benzene. The mother liquor was further purified on silica gel (10% ethyl acetate in hexane) to afford additional 4.8 g of product. 58% yield. $^1$H NMR (300 MHz; CDCl$_3$): δ 1.43 (s, 6H), 3.82 (s, 3H), 3.93 (s, 2H), 6.75 (dd, J=2.4 Hz and 7.2 Hz, 1H), 7.32 (m, 2H).

h. 3-bromo-4-trifluoromethoxy benzaldehyde.

To a solution of 4-trifluoromethoxybenzaldehyde (150 g, 0.79 mol) in a mixture of TFA (400 mL) and H$_2$SO$_4$ (80 mL) was added at 40–45° C. N-bromosuccinimide (281 g, 1.579 mol) in equal portion over 2 hours. The reaction mixture was stirred at 40–45° C. overnight, poured into ice-water and extracted with CH$_2$Cl$_2$. The organic layer was washed with water then treated with saturated NaHCO$_3$ (800 mL) for 30 minutes. The layers were separated and the organic layer further washed with water and brine, dried over MgSO$_4$, filtered and evaporated. The residue was triturated with hexane and filtered. After evaporation of the solvent, the residue was distilled to give 3-bromo-4-trifluoromethoxy-benzaldehyde (150.2 g, 60° C., 0.3 mm/Hg, 70%). $^1$H NMR (300 MHz; CDCl$_3$): δ 7.49 (dd, J$_1$=1.8 Hz and J$_2$=8.7 Hz, 1H), 7.88 (dd, J$_1$=2.1 Hz and j$_2$=8.4 Hz, 1H), 8.17 (d, J=1.8 Hz, 1H), 9.97 (s, 1H).

Example 2

5-[3-(5-Isobutyryl-3,3-dimethyl-2,3-dihydro-benzofuran-7-yl)-4-trifluoromethoxy-benzylidene]-thiazolidine-2,4-dione, which can be referred to as "Compound 2."

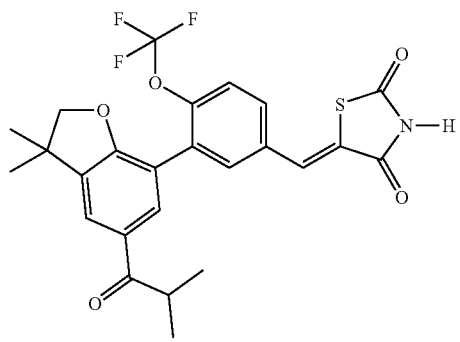

Prepared in a similar manner to example 1 using 3-(5-Isobutyryl-3,3-dimethyl-2,3-dihydro-benzofuran-7-yl)-4-trifluoromethoxy-benzaldehyde. 55% yield after crystallization from ethanol. mp 92–96° C. $^1$H-NMR (300 MHz, DMSO-d-6): 1.11 (d, J=6.4 Hz, 6H), 1.37 (s, 6H), 3.69 (m, 1H), 4.34 (s, 2H), 7.63 (d, J=8.5 Hz, 1H), 7.75 (d, J=8.5 Hz, 1H), 7.84 (s, 1H), 7.87 (s, 2H), 7.93 (s, 1H), 12.72 (br s, 1H).

The intermediate 3-(5-Isobutyryl-3,3-dimethyl-2,3-dihydro-benzofuran-7-yl)-4-trifluoromethoxy-benzaldehyde was prepared as follows:

a. 3-(5-Isobutyryl-3,3-dimethyl-2,3-dihydro-benzofuran-7-yl)-4-trifluoromethoxy-benzaldehyde.

A mixture of 3-formyl-6-trifluoromethoxy-1-phenyl boronic acid (1.27 g, 5.43 mmol), 1-(7-bromo-3,3-dimethyl-2,3-dihydro-benzofuran-5-yl)-2-methyl-propan-1-one (1.35 g, 4.53 mmol) and potassium carbonate (1.25 g, 9.06 mmol) in toluene (15 mL), ethanol (3 mL) and water (1.8 mL) was degassed with argon for 30 minutes. Tetrakis(triphenylphosphine)palladium(0) (105 mg, 0.09 mmol) was added and the mixture heated at reflux under argon for 16 hrs. The solution was cooled to room temperature, diluted with ethyl acetate and washed successively with water and brine, dried over anhydrous magnesium sulfate, filtered and evaporated. The residue was purified on silica-gel (10% ethyl acetate inhexane) to give 405 mg of 3-(5-Isobutyryl-3,3-dimethyl-2,3-dihydro-benzofuran-7-yl)-4-trifluoromethoxy-benzaldehyde (22%).

$^1$H NMR (300 MHz; CDCl$_3$): 1.22 (d, J=7.5 Hz, 6H), 1.42 (s, 6H), 3.54 (m, 1H), 4.35 (s, 2H), 7.51 (d, J=8.7 Hz, 1H), 7.85 (d, J=8.4 Hz, 1H), 7.96 (d, J=7.5 Hz, 1H), 8.03 (d, J=1.8 Hz, 1H), 10.05 (s, 1H).

b. 3-formyl-6-trifluoromethoxy-1-phenyl boronic acid.

To a mixture of 2-(3-bromo-4-trifluoromethoxy-1-phenyl)-1,3-dioxolane (7.20 g, 22.9 mmol) in THF (70 mL) cooled to −78° C. under an atmosphere of argon was added n-BuLi (13.8 mL, 2.5 M, 34.4 mmol) dropwise. The resulting suspension was stirred for 5 minutes and triisopropyllborate (15.9 mL, 68.7 mmol) was added dropwise via syringe. The mixture was stirred at −50° C. for 2 hours then warmed up to room temperature and stirred overnight at room temperature. 1.0 N HCl (50 mL) was slowly added to the reaction mixture. After 3 hours the mixture was diluted with ethyl acetate and the layers separated, the aqueous layer was extracted once with ethyl acetate and the two organic layers combined. The resulting organic layer was washed with water, brine and dried (MgSO$_4$). The mixture was filtered, evaporated and the residue stirred in hexane. The resulting white suspension was filtered and the white solid dried under high vacuum to afford 3.00 g of 3-formyl-6-trifluoromethoxy-1-phenyl boronic acid (56%). $^1$H NMR (300 MHz; CDCL$_3$): δ 7.42 (d, J=7.0 Hz, 1H), 8.07 (dd, J$_1$=2.1 Hz, J$_2$=8.7 Hz, 1H), 8.47 (d, J=1.8 Hz, 1H), 10.05 (s, 1H).

c. 2-(3-bromo-4-trifluoromethoxy-1-phenyl)-1,3-dioxolane.

To a solution of 3-bromo-4-trifluoromethoxybenzaldehyde (20 g, 74.0 mmol) in toluene (200 mL) was added ethylene glycol (82.6 mL, 1.48 mol) and p-toluenesulfonic acid monohydrate (0.84 g, 4.44 mmol). The reaction mixture was heated at reflux overnight and the water was removed using a Dean Stark apparatus. The solution was cooled to room temperature, poured into aqueous potassium carbonate (10%) and extracted with ethyl acetate. The organic layer was washed with water, brine and dried (MgSO$_4$). The residue was purified on silica gel (10% ethyl acetate in hexane) to give 15.4 g of 2-(3-bromo-4-trifluoromethoxy-1-phenyl)-1,3-dioxolane (66%). $^1$H NMR (300 MHz; CDCl$_3$): δ 4.05 (m, 2H), 4.11 (m, 2H), 5.79 (s, 1H), 7.32 (dd, J=$_1$1.5 Hz, J$_2$=8.1 Hz, 1H),7.43 (dd, J$_1$=1.8 Hz, J$_2$=8.4 Hz, 1H), 7.77 (d, J=2.1 Hz, 1H).

d. 1-(7-bromo-3,3-dimethyl-2,3-dihydro-benzofuran-5-yl)-2-methyl-propan-1-one.

To a solution of AlCl₃ (1.5 g, 11.32 mmol) in dry dichloromethane (30 mL) was added dropwise at room temperature 1-(3,3-dimethyl-2,3-dihydro-benzofuran-5-yl)-2-methyl-propan-1-one (989 mg, 4.52 mmol) in dichloromethane (15 mL) followed by bromine (0.28 mL, 5.43 mmol) and the reaction stirred for 6 hours. 1N HCl was added slowly and the layers separated. The aqueous layer was extracted twice with dichloromethane. The combined organic layers were washed successively with aq. K₂CO₃, water and brine, dried over anhydrous magnesium sulfate, filtered and evaporated to give 1.44 g of 1-(7-bromo-3,3-dimethyl-2,3-dihydro-benzofuran-5-yl)-2-methyl-propan-1-one (91%). ¹H NMR (300 MHz; CDCl₃): δ 1.21 (d, J=6.9 Hz, 6H), 1.39 (s, 6H), 3.47 (m, 1H), 4.43 (s, 2H), 7.70 (s, 1H), 7.95 (s, 1H). e. 1-(3,3-dimethyl-2,3-dihydro-benzofuran-5-yl)-2-methyl-propan-1-one.

To a solution of 1-(3,3-dimethyl-2,3-dihydro-benzofuran-5-yl)-2-methyl-propan-1-ol (example 1e) (1.13 g, 5.15 mmol) in dry dichloromethane (20 mL) was added at room temperature pyridinium chlorochromate (1.33 g, 6.18 mmol). The reaction mixture was stirred for 2 hours at room temperature then filtered over celite. Water was added and the layers separated. The aqueous layer was extracted twice with dichloromethane. The combined organic layers were washed successively with water and brine, dried over anhydrous magnesium sulfate, filtered and evaporated. The residue was chromatographed on silica gel (5% ethyl acetate in hexane) to give 530 mg of 1-(3,3-dimethyl-2,3-dihydro-benzofuran-5-yl)-2-methyl-propan-1-one (47%). ¹H NMR (300 MHz; CDCl₃): δ 1.21 (d, J=7.2 Hz, 6H), 1.38 (s, 6H), 3.52 (m, 1H), 4.32 (s, 2H), 6.80 (d, J=7.5 Hz, 1H), 7.80 (m, 2H).

Example 3

7-[5-(2,4-Dioxo-thiazolidin-5-ylidenemethyl)-2-trifluoromethoxy-phenyl]-3,3-dimethyl-2,3-dihydro-benzofuran-5-carboxylic acid methylamide, which can be referred to as "Compound 3"

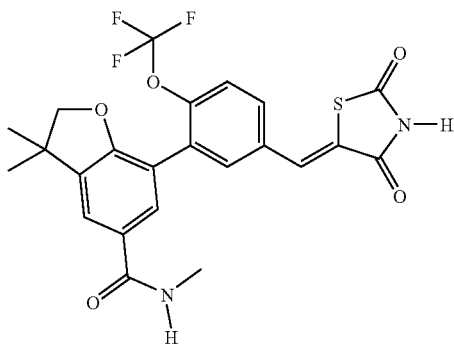

Prepared in a similar manner to example 1 using 7-[5-formyl-2-trifluoromethoxy-phenyl]-3,3-dimethyl-2,3-dihydro-benzofuran-5-carboxylic acid methylamide. 45% yield. mp 227–229° C. ¹H-NMR (300 MHz, DMSO-d-6): 1.35 (s, 6H), 2.77 (d, J=4.4 Hz, 3H), 4.30 (s, 2H), 7.63 (dd, J₁=8.8 Hz, J₂=1.8 Hz, 1H), 7.71 (d, J=1.8 Hz, 1H), 7.74 (dd, J₁=8.8 Hz, J₂=2.3 Hz, 1H), 7.79 (d, J=2.3 Hz, 1H), 7.80 (d, J=2.3 Hz, 1H), 7.87 (s, 1H), 8.32 (q, J=4.7 Hz, 1H), 12.71(br s, 1H).

The intermediate 7-[5-formyl-2-trifluoromethoxy-phenyl]-3,3-dimethyl-2,3-dihydro-benzofuran-5-carboxylic acid methylamide was prepared in a similar manner to example 2a using 7-bromo-3,3-dimethyl-2,3-dihydro-benzofuran-5-carboxylic acid methylamide and 3-formyl-6-trifluoromethoxy-1-phenyl boronic acid (example 2b). ¹H-NMR (300 MHz, (300 MHz; CDCl₃): 1.28 (s, 6H), 3.00 (d, J=5.4 Hz, 3H), 4.31 (s, 2H), 6.09 (br s, 1H), 7.51 (m, 2H), 7.55 (s, 1H), 7.66(s, 1H), 7.95(d, J₁ =8.7 Hz J₂=2.1 Hz, 1H), 8.01 (d, J=2.1 Hz, 1H), 10.03 (s, 1H).

a. 7-bromo-3,3-dimethyl-2,3-dihydro-benzofuran-5-carboxylic acid methylamide.

To a solution of 7-bromo-3,3-dimethyl-2,3-dihydro-benzofuran-5-carboxylic acid (4.99 g, 18.41 mmol) in dry THF (40 mL) was added at room temperature thionychloride (2 mL, 27.61 mmol) and DMF (0.14 mL, 1.84 mmol). The reaction mixture was stirred 1 hr then methylamine hydrochloride (2.48 g, 36.82 mmol) was added followed by slow addition of pyridine (4.5 mL, 55.23 mmol). The reaction mixture was stirred overnight then water and ethyl acetate were added. The layers were separated. The aqueous layer was extracted twice with ethyl acetate. The combined extracts were washed successively with water and brine, dried over anhydrous magnesium sulfate, filtered and evaporated. The residue was chromatographed on silica gel (50% to 100% ethyl acetate in hexane, then 40% MeOH in Ethyl acetate) to give 1.17 g of 7-bromo-3,3-dimethyl-2,3-dihydro-benzofuran-5-carboxylic acid methylamide (22%). ¹H NMR (300 MHz; CDCl₃): 1.36 (s, 6H), 2.99 (d, J=4.5 Hz, 3H), 4.39 (s, 2H), 6.25 (br s, 1H), 7.54 (d, J=1.5 Hz, 1H), 7.70 (d, J=1.5 Hz, 1H).

b. 7-bromo-3,3-dimethyl-2,3-dihydro-benzofuran-5-carboxylic acid.

A solution of 7-bromo-3,3-dimethyl-2,3-dihydro-benzofuran-5-carbaldehyde (14.61 g, 57.29 mmol) in acetone (80 mL) was added at room temperature to KMnO₄ (9.05 g, 57.29 mmol) dissolved in water (200 mL). The reaction mixture was stirred at room temperature overnight filtered over celite then H₂SO₄ in water was added and the solution extracted with ethyl acetate. The organic layer was further washed with water and brine, dried over anhydrous magnesium sulfate, filtered and evaporated to give 9.9 g of 7-bromo-3,3-dimethyl-2,3-dihydro-benzofuran-5-carboxylic acid (64%). ¹H NMR (300 MHz; CDCl₃): 1.40 (s, 6H), 4.44 (s, 2H), 7.79 (s, 1H), 8.13 (s, 1H). c. 7-bromo-3,3-dimethyl-2,3-dihydro-benzofuran-5-carbaldehyde.

To a solution of AlCl₃ (1.22 g, 9.18 mmol) in dry dichloromethane (15 mL) was added dropwise at room temperature 3,3-dimethyl-2,3-dihydro-benzofuran-5-carbaldehyde (647 mg, 3.67 mmol) in dichloromethane (15 mL) followed by bromine (0.23 mL, 4.41 mmol) and the reaction stirred for 3 hours. 1N HCl was added slowly and the layers separated. The aqueous layer was extracted twice with dichloromethane. The combined organic layers were washed successively with water and brine, dried over anhydrous magnesium sulfate, filtered and evaporated. The residue was chromatographed on silica gel (20% ethyl acetate in hexane) to give 856 mg of 7-bromo-3,3-dimethyl-2,3-dihydro-benzofuran-5-carbaldehyde (91%). ¹H NMR (300 MHz; CDCl₃): 1.40(s, 6H), 4.46 (s, 2H), 7.61 (s, 1H), 7.83 (s, 1H), 9.80 (s, 1H).

d. 3,3-dimethyl-2,3-dihydro-benzofuran-5-carbaldehyde.

To a solution of 5-bromo-3,3-dimethyl-2,3-dihydro-benzofuran (example 1f) (15.90 g, 70.01 mmol) in dry THF (100 mL) at −78° C., under argon, was added dropwise n-BuLi (1.6 M in hexane, 105 mmol, 42 mL). The mixture was stirred for 5 minutes then DMF (16.3 mL, 210 mmol) was added and the mixture was quickly warmed up to −50° C. and then to 0° C. for 3 hrs. Water was added slowly and the solution extracted with ethyl acetate. The organic layer was further washed with water, brine, dried (MgSO$_4$), filtered and evaporated to give 13.15 g of 3,3-dimethyl-2,3-dihydro-benzofuran-5-carbaldehyde use as this in the next step. $^1$H NMR (300 MHz; CDCl$_3$): 1.38 (s, 6H), 4.36 (s, 2H), 6.89 (d, J=7.8 Hz, 1H), 7.68 (m, 2H), 9.85 (s, 1H).

Example 4

7-[5-(2,4-Dioxo-thiazolidin-5-ylidenemethyl)-2-trifluoromethoxy-phenyl]-3,3-dimethyl-2,3-dihydro-benzofuran-5-carboxylic acid dimethylamide, which can be referred to as "Compound 4."

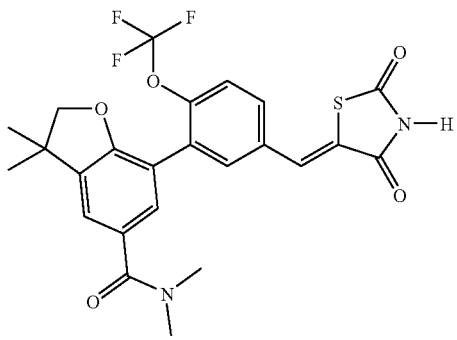

Prepared in a similar manner to example 1 using 7-[5-formyl-2-trifluoromethoxy-phenyl]-3,3-dimethyl-2,3-dihydro-benzofuran-5-carboxylic acid dimethylamide. 25% yield. mp 268–272° C. $^1$H-NMR (300 MHz, DMSO-d-6): 1.35 (s, 6H), 2.98 (s, 6H), 4.28 (s, 2H), 7.23 (d, J=1.8 Hz, 1H), 7.40 (d, J=1.8 Hz, 1H), 7.62 (dd, J=8.5 Hz and J=1.5 Hz, 1H), 7.73 (dd, J=8.8 Hz and J=2.3 Hz, 1H), 7.79 (d, J=2.3 Hz, 1H), 7.87 (s, 1H), 12.71 (br s, 1H).

The intermediate 7-[5-formyl-2-trifluoromethoxy-phenyl]-3,3-dimethyl-2,3-dihydro-benzofuran-5-carboxylic acid dimethylamide was prepared as followed:

a. 7-[5-formyl-2-trifluoromethoxy-phenyl]-3,3-dimethyl-2,3-dihydro-benzofuran-5-carboxylic acid dimethylamide.

To a solution of 7-bromo-3,3-dimethyl-2,3-dihydro-benzofuran-5-carboxylic acid dimethylamide (437 mg, 1.46 mmol) in dioxane (4 mL), were added under argon, triethylamine (0.82 mL, 5.86 mmol), Pd(OAc)$_2$ (16 mg, 0.07 mmol), 2-(dicyclohexylphosphino)biphenyl (103 mg, 0.29 mmol) and pinacolborane (0.64 mL, 4.40 mmol) dropwise. The mixture was heated at 80° C. under argon for 2 hrs then cooled to room temperature. Water (0.5 mL) was added dropwise, then Ba(OH)$_2$.8H$_2$O (1.38 g, 4.40 mmol) followed by 3-bromo-4-trifluoromethoxy benzaldehyde (example 1h) (473 mg, 1.76 mmol) dissolved in dioxane (1.2 mL). The mixture was refluxed for 4 hours then cooled to room temperature, diluted with ethyl acetate and filtered over celite. The solution was further washed with water and brine, dried over anhydrous magnesium sulfate, filtered and evaporated. The residue was purified on silica gel (5% methanol in dichloromethane) to give 264 mg of 7-[5-formyl-2-trifluoromethoxy-phenyl]-3,3-dimethyl-2,3-dihydro-benzofuran-5-carboxylic acid dimethylamide (containing 50% of 3,3-dimethyl-2,3-dihydro-benzofuran-5-carboxylic acid dimethylamide as determined by $^1$H NMR) use as this in the next step.

b. 7-bromo-3,3-dimethyl-2,3-dihydro-benzofuran-5-carboxylic acid dimethylamide.

Prepared in a similar manner to example 3a using 7-bromo-3,3-dimethyl-2,3-dihydro-benzofuran-5-carboxylic acid (example 3b) and dimethylamine hydrochloride. 45% yield. $^1$H NMR (300 MHz; CDCl$_3$): 1.36 (s, 6H), 3.05 (br s, 6H), 4.37 (s, 2H), 7.16 (d, J=1.5 Hz, 1H), 7.38 (d, J=1.5 Hz, 1H).

Example 5

5-[3-(3,3-Dimethyl-5-propionyl-2,3-dihydro-benzofuran-7-yl)-4-trifluoromethoxy-benzylidene]-thiazolidine-2,4-dione, which can be referred to as "Compound 5"

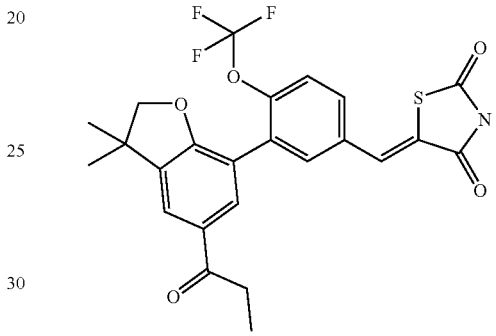

Prepared in a similar manner to example 1 using 3-(3,3-dimethyl-5-propionyl-2,3-dihydro-benzofuran-7-yl)-4-trifluoromethoxy-benzaldehyde. 74% yield, mp 105–108° C. $^1$H-NMR (300 MHz, DMSO-d-6): 1.09 (t, J=7.3 Hz, 3H), 1.37 (s, 6H), 3.03 (q, J=7.3 Hz, 2H), 4.34 (s, 2H), 7.63 (dd, J=8.8 Hz, J$_2$=1.8 Hz, 1H), 7.74 (dd, J$_1$=8.8 Hz, J$_2$=2.3 Hz, 1H), 7.83 (d, J=2.3 Hz, 1H), 7.86 (d, J=1.8 Hz, 1H), 7.88 (s, 1H), 7.92 (d, J=1.8 Hz, 1H), 12.72 (br s, 1H).

The intermediate 3-(3,3-dimethyl-5-propionyl-2,3-dihydro-benzofuran-7-yl)-4-trifluoromethoxy-benzaldehyde was prepared as followed:

a. 3-(3,3-dimethyl-5-propionyl-2,3-dihydro-benzofuran-7-yl)-4-trifluoromethoxy-benzaldehyde.

A mixture of 1-[3,3-dimethyl-7-(4,4,5,5-tetramethyl-[1,3,2]dioxaborolan-2-yl)-2,3-dihydro-benzofuran-5-yl]-propan-1-one (1.33 g, 4.05 mmol), 3-bromo-4-trifluoromethoxybenzaldehyde (example 1h) (1.09 g, 4.05 mmol) and potassium carbonate (1.12 g, 8.10 mmol) in toluene (12 mL), ethanol (2.4 mL) and water (1.5 mL) was degassed with argon for 30 minutes. Tetrakis(triphenylphosphine)palladium(0) (234 mg, 0.20 mmol) was added and the mixture heated at reflux under argon for 19 hrs. The solution was cooled to room temperature, diluted with ethyl acetate and washed successively with water and brine, dried over anhydrous magnesium sulfate, filtered and evaporated. The residue was purified on silica gel (10% ethyl acetate in hexane) to give 1.17 g of 3-(3,3-dimethyl-5-propionyl-2,3-dihydro-benzofuran-7-yl)-4-trifluoromethoxy-benzaldehyde (50%). $^1$H NMR (300 MHz; CDCl$_3$): 1.23 (t, J=7.2 Hz, 3H), 1.42 (s, 6H), 2.99 (q, J=7.2 Hz, 2H), 4.34 (s, 2H), 7.52 (dd, J$_1$=7.2 Hz, J$_2$=1.8 Hz, 1H), 7.84 (d, J=2.1 Hz, 1H), 7.85 (d, J=2.13 Hz, 1H), 7.96 (dd, J$_1$=8.4 Hz, J$_2$=2.1 Hz, 1H), 8.03 (d, J=2.1 Hz, 1H), 10.05 (s, 1H).

b. 1-[3,3-dimethyl-7-(4,4,5,5-tetramethyl-[1,3,2]dioxaborolan-2-yl)-2,3-dihydro-benzofuran-5-yl]-propan-1-one.

To a solution of 1-(7-bromo-3,3-dimethyl-2,3-dihydro-benzofuran-5-yl)-propan-1-one (1.69 g, 5.99 mmol) in dioxane (16 mL), were added under argon, triethylamine (3.34 mL, 23.96 mmol), Pd(OAc)$_2$ (67 mg, 0.30 mmol), 2-(dicyclohexylphosphino)biphenyl (420 mg, 1.20 mmol) and pinacolborane (2.61 mL, 17.97 mmol) dropwise. The mixture was heated at 85° C. under argon for 1.5 hrs then cooled to room temperature. Water (0.5 mL) was added dropwise followed by saturated aqueous NH$_4$Cl solution. The solution was extracted with ethyl acetate then washed successively with water and brine, dried over anhydrous magnesium sulfate, filtered and evaporated. The residue was purified on silica gel (10% to 20% ethyl acetate in hexane) to give 1.34 g of 1-[3,3-dimethyl-7-(4,4,5,5-tetramethyl-[1,3,2]dioxaborolan-2-yl)-2,3-dihydro-benzofuran-5-yl]-propan-1-one.

c. 1-(7-bromo-3,3-dimethyl-2,3-dihydro-benzofuran-5-yl)-propan-1-one.

To a solution of AlCl$_3$ (2.42 g, 18.18 mmol) in dry dichloromethane (30 mL) was added dropwise at room temperature 1-(3,3-dimethyl-2,3-dihydro-benzofuran-5-yl)-propan-1-one (1.48 g, 7.27 mmol) in dichloromethane (30 mL) followed by bromine (0.45 mL, 8.72 mmol) and the reaction stirred for 12 hours at room temperature. 1N HCl was added slowly and the layers separated. The aqueous layer was extracted twice with dichloromethane. The combined organic layers were washed successively with water, aq. NaHCO$_3$, water and brine, dried over anhydrous magnesium sulfate, filtered and evaporated to give 1.7 g of 1-(7-bromo-3,3-dimethyl-2,3-dihydro-benzofuran-5-yl)-1-propan-1-one (83%). $^1$H NMR (300 MHz; CDCl$_3$): δ 1.21 (t, J=7.2 Hz, 3H), 1.39 (s, 6H), 2.92 (q, J=7.2 Hz, 2H), 4.42 (s, 2H), 7.70 (s, 1H), 7.96 (s, 1H).

d. 1-(3,3-dimethyl-2,3-dihydro-benzofuran-5-yl)-propan-1-one.

To a solution of 1-(3,3-dimethyl-2,3-dihydro-benzofuran-5-yl)-propan-1-ol (2.6 g, 12.60 mmol) in dry dichloromethane (40 mL) was added at room temperature pyridinium chlorochromate (3 g, 13.86 mmol). The reaction mixture was stirred for 1 hour at room temperature then filtered over celite. Water was added and the layers separated. The aqueous layer was extracted twice with dichloromethane. The combined organic layers were washed successively with water and brine, dried over anhydrous magnesium sulfate, filtered and evaporated. The residue was chromatographed on silica gel (5% ethyl acetate in hexane) to give 530 mg of 1-(3,3-dimethyl-2,3-dihydro-benzofuran-5-yl)-propan-1-one (58%). $^1$H NMR (300 MHz; CDCl$_3$): δ 1.21 (t, J=7.2 Hz, 3H), 1.37 (s, 6H), 2.94 (q, J=7.2 Hz, 2H), 4.32 (s, 2H), 6.80 (d, J=8.4 Hz, 1H), 7.79 (s, 1H), 7.81 (d, J=8.4 Hz, 1H).

e. 1-(3,3-dimethyl-2,3-dihydro-benzofuran-5-yl)-propan-1-ol.

Prepared in a similar manner to example 1e using 5-bromo-3,3-dimethyl-2,3-dihydro-benzofuran (example 1f) and propionaldehyde. (92%). $^1$H NMR (300 MHz; CDCl$_3$): δ 0.91 (t, J=7.5 Hz, 3H), 1.33 (s, 3H), 1.34 (s, 3H), 1.77 (m, 4H), 4.23 (s, 2H), 4.54 (t, J=6.9 Hz, 1H), 6.73 (d, J=8.1 Hz, 1H), 7.07 (dd, J=7.8 Hz and 1.8 Hz, 1H), 7.10 (d, J=1.5 Hz, 1H).

Example 6

5-[2,5-Difluoro-3-(5-isobutyl-3,3-dimethyl-2,3-dihydro-benzofuran-7-yl)-4-methoxy-benzylidene]-thiazolidine-2,4-dione, which can be referred to as "Compound 6"

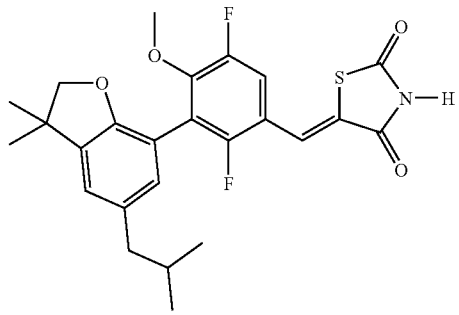

Prepared in a similar manner to example 1 using 2,5-Difluoro-3-(5-isobutyl-3,3-dimethyl-2,3-dihydro-benzofuran-7-yl)-4-methoxy-benzaldehyde. mp 165–168° C. 1H-NMR (300 MHz, CDCl3): 0.91 (d, J=6.6 Hz, 6H), 1.36 (s, 3H), 1.37 (s, 3H), 1.82 (m, 1H), 2.44 (d, J=6.9 Hz, 2H), 3.90 (2 s, 3H), 4.22 (2 s, 2H), 6.83 (s, 1H), 6.94 (d, J=6.9 and 12 Hz, 1H), 8.01 (s, 1H), 8.29 (br s, 1H).

The intermediate 2,5-Difluoro-3-(5-isobutyl-3,3-dimethyl-2,3-dihydro-benzofuran-7-yl)-4-methoxy-benzaldehyde was prepared in a similar manner as in example 1 a using 5-isobutyl-3,3-dimethyl-2,3-dihydro-benzofuran-7-boronic acid (example 1b) and 2,5-difluoro-3-iodo-4-methoxy-benzaldehyde Example 7

5-[4-Dimethylamino-3-(5-isobutyl-3,3-dimethyl-2,3-dihydro-benzofuran-7-yl)-benzylidene]-thiazolidine-2,4-dione, which can be referred to as "Compound 7"

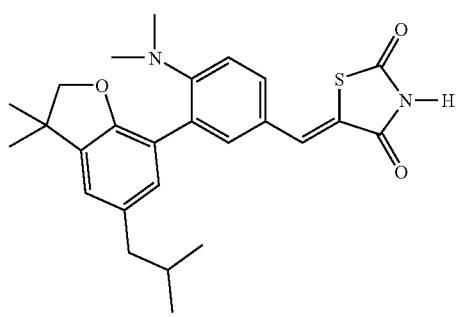

Prepared in a similar manner to example 1 using 4-Dimethylamino-3-(5-isobutyl-3,3-dimethyl-2,3-dihydro-benzofuran-7-yl)-benzaldehyde. mp 205–207° C. $^1$H-NMR (300 MHz, DMSO-d-6): 0.88 (d, J=6.6 Hz, 6H), 1.31 (s, 6H), 1.79 (m, 1H), 2.42 (d, J=6.9 Hz, 2H), 2.62 (s, 6H), 4.18 (s, 2H), 6.91 (d, J=1.8 Hz, 1H), 6.95 (d, J=1.5 Hz, 1H), 7.02 (d, J=8.57 Hz, 1H), 7.37 (d, J=2.4 Hz, 1H), 7.44 (dd, J$_1$=2.4 Hz, J$_2$=8.7 Hz, 1H), 7.70 (s, 1H), 12.41 (br s, 1H).

The intermediate 4-Dimethylamino-3-(5-isobutyl-3,3-dimethyl-2,3-dihydro-benzofuran-7-yl)-benzaldehyde was prepared in a similar manner as in example 2a using 1-(7-bromo-3,3-dimethyl-2,3-dihydro-benzofuran-5-yl)-2-methyl-propan-1-one (example 2d) and 2-dimethylamino-5-formyl-1-phenylboronic acid.

Example 8

7-[5-(2,4-Dioxo-thiazolidin-5-ylidenemethyl)-2-trifluoromethoxy-phenyl]-3,3-dimethyl-2,3-dihydro-benzofuran-5-carboxylic acid methyl ester, which can be referred to as "Compound 8"

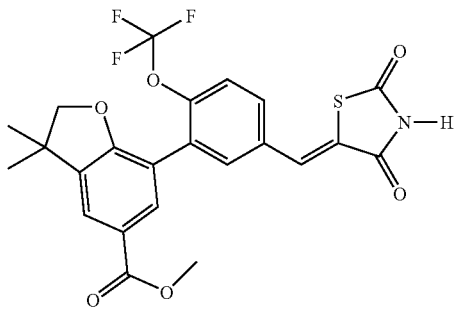

Prepared in a similar manner to example 1 using 7-(5-formyl-2-trifluoromethoxy-phenyl)-3,3-dimethyl-2,3-dihydro-benzofuran-5-carboxylic acid methyl ester. mp 307–310° C. $^1$H-NMR (300 MHz, DMSO-d-6): 1.36 (s, 6H), 3.83 (s, 3H), 4.35 (s, 2H), 7.63 (dd, J$_1$=8.5 Hz, J$_2$=1.5 Hz, 1H), 7.75 (dd, J$_1$=8.8 Hz, J$_2$=2.3 Hz, 1H), 7.81 (d, J=1.8 Hz, 1H), 7.82 (d, J=2.3 Hz, 1H), 7.87 (s, 1H), 7.88 (d, J=1.8 Hz, 1H), 12.72 (br s, 1H).

The intermediate 7-(5-formyl-2-trifluoromethoxy-phenyl)-3,3-dimethyl-2,3-dihydro-benzofuran-5-carboxylic acid methyl ester was prepared in a similar manner to example 2a using 7-bromo-3,3-dimethyl-2,3-dihydro-benzofuran-5-carboxylic acid methyl ester and 3-formyl-6-trifluoromethoxy-1-phenyl boronic acid (example 2b). 72% yield. $^1$H-NMR (300 MHz, CDCl$_3$): 1.41 (s, 3H), 3.90 (s, 3H), 4.33 (s, 2H), 7.48 (d, J=8.7 Hz, 1H), 7.87–8.01 (m, 4H), 10.04 (s, 1H).

Example 9

5-[3-(5-Furan-3-yl-3,3-dimethyl-2,3-dihydro-benzofuran-7-yl)-4-trifluoromethoxy-benzylidene]-thiazolidine-2,4-dione, which can be referred to as "Compound 9"

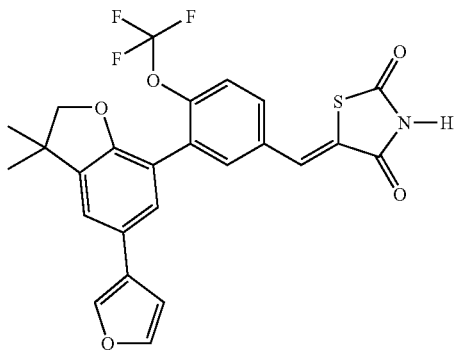

Prepared in a similar manner to example 1 using 3-(5-Furan-3-yl-3,3-dimethyl-2,3-dihydro-benzofuran-7-yl)-4-trifluoromethoxy-benzaldehyde. 68% yield. $^1$H-NMR (300 MHz, DMSO-d-6): 1.34 (s, 6H), 4.21 (s, 2H), 6.94 (m, 1H), 7.38 (d, J=1.8 Hz, 1H), 7.54 (d, J=1.8 Hz, 1H), 7.59 (m, 2H), 7.79 (d, J=2.4 Hz, 1H), 7.85 (s, 1H), 12.68 (br s, 1H).

The intermediate 3-(5-Furan-3-yl-3,3-dimethyl-2,3-dihydro-benzofuran-7-yl)-4-trifluoromethoxy-benzaldehyde was prepared as followed:

a. 3-(5-Furan-3-yl-3,3-dimethyl-2,3-dihydro-benzofuran-7-yl)-4-trifluoromethoxy-benzaldehyde.

A mixture of 3-(5-bromo-3,3-dimethyl-2,3-dihydro-benzofuran-7-yl)-4-trifluoromethoxy-benzaldehyde (580 mg, 1.40 mmol), 3-furanboronic acid (316 mg, 2.8 mmol) and potassium carbonate (387 mg, 2.8 mmol) in DME (10 mL) and water (1 mL) was degassed with argon for 15 minutes.

Tetrakis(triphenylphosphine)palladium(0) (81 mg, 0.07 mmol) was added and the mixture heated at reflux under argon for 20 hrs. The solution was cooled to room temperature, diluted with ethyl acetate and washed successively with water and brine, dried over anhydrous magnesium sulfate, filtered and evaporated. The residue was purified on silica gel (10% ethyl acetate in hexane) to give 148 mg of 3-(5-Furan-3-yl-3,3-dimethyl-2,3-dihydro-benzofuran-7-yl)-4-trifluoromethoxy-benzaldehyde (26%). $^1$H NMR (300 MHz; CDCl$_3$): 1.41 (s, 6H), 4.28 (s, 2H), 6.67 (m, 1H), 7.26 (m, 2H), (m, 7.50(m, 2H), 7.68 (m, 2H), 7.93 (dd, J$_1$=2.4 Hz, J$_2$=8.5 Hz, 1H), 8.05 (d, J=2 Hz, 1H), 10.05 (s, 1H).

b. 3-(5-bromo-3,3-dimethyl-2,3-dihydro-benzofuran-7-yl)-4-trifluoromethoxy-benzaldehyde.

A mixture of 5-bromo-7-iodo-3,3-dimethyl-2,3-dihydro-benzofuran (2.85 g, 8.07 mmol), 3-formyl-6-trifluoromethoxy-1-phenyl boronic acid (1.72 g, 7.34 mmol) and potassium carbonate (2.03 g, 14.7 mmol) in toluene (25 mL), ethanol (5 mL) and water (3 mL) was degassed with argon for 20 minutes. Tetrakis(triphenylphosphine)palladium(0) (844 mg, 0.73 mmol) was added and the mixture heated at reflux under argon for 21 hrs. The solution was cooled to room temperature, diluted with ethyl acetate and washed successively with water and brine, dried over anhydrous magnesium sulfate, filtered and evaporated. The residue was purified on silica gel (10% ethyl acetate in hexane) to give 585 mg of 3-(5-bromo-3,3-dihydro-benzofuran-7-yl)-4-trifluoromethoxy-benzaldehyde (19%). $^1$H NMR (300 MHz; CDCl$_3$): 1.39 (s, 6H), 4.26 (s, 2H), 7.28 (m, 2H), 7.51 (m, 2H), 7.92–7.98 (m, 2H), 10.04 (s, 1H).

c. 5-bromo-7-iodo-3,3-dimethyl-2,3-dihydro-benzofuran.

5-Bromo-3,3-dimethyl-2,3-dihydro-benzofuran (example 1f) (10 g, 44 mmol) was dissolved in glacial acetic acid (40 mL), iodine monochloride (10.86 g, 66.9 mmol) was added and the reaction mixture was heated at reflux for 72 hours then cooled to 0° C., and 1N NaOH was slowly added until pH=8 followed by Na$_2$CO$_3$ until the solution become colorless. The solution was extracted with ethyl acetate and the organic layer further washed with water and brine, dried over anhydrous magnesium sulfate, filtered and evaporated. The residue was purified on silica gel (10% ethyl acetate in hexane) to give 8.7 g of 5-bromo-7-iodo-3,3-dimethyl-2,3-dihydro-benzofuran (56%). $^1$H NMR (300 MHz; CDCl$_3$): 1.34 (s, 6H), 4.32 (s, 2H), 7.13 (d, J=2 Hz, 1H), 7.58 (d, J=2 Hz, 1H).

Example 10

2-[3,3-Dimethyl-7-(2-trifluoromethoxy-5-vinyl-phenyl)-2,3-dihydro-benzofuran -5-ylmethoxy]-ethanol; compound with thiazolidine-2,4-dione, which can be referred to as "Compound 10"

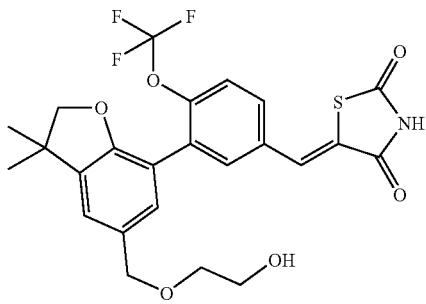

Prepared in a similar manner to example 1 using 3-[5-(2-Hydroxy-ethoxymethyl)-3,3-dimethyl-2,3-dihydro-benzofuran-7-yl]-4-trifluoromethoxy-benzaldehyde. 75% yield, mp 166–169° C. $^1$H-NMR (300 MHz, DMSO-d-6): 1.33 (s, 6H), 3.50 (m, 4H), 4.22 (s, 2H), 4.46 (s, 2H), 4.64 (m, 1H), 7.12 (s, 1H), 7.27 (s, 1H), 7.60 (d, J=8.8 Hz, 1H), 7.72 (d, J=8.8 Hz, 1H), 7.75 (s, 1H), 7.86 (s, 1H), 12.70 (br s, 1H).

The intermediate 3-[5-(2-Hydroxy-ethoxymethyl)-3,3-dimethyl-2,3-dihydro-benzofuran-7-yl]-4-trifluoromethoxy-benzaldehyde was prepared as follows:

a. 3-[5-(2-Hydroxy-ethoxymethyl)-3,3-dimethyl-2,3-dihydro-benzofuran-7-yl]-4-trifluoromethoxy-benzaldehyde.

A mixture of 2-[7-(5-[1,3]dioxolan-2-yl-2-trifluoromethoxy-phenyl)-3,3-dimethyl-2,3-dihydro-benzofuran-5-ylmethoxy]-ethanol (393 mg, 0.89 mmol) and 1N HCl (9 mL) in tetrahydrofuran (4 mL) was stirred for 1 hour at room temperature. The mixture was diluted with ethyl acetate and the layers were separated. The aqueous layer was neutralized with an aqueous solution of sodium bicarbonate and the mixture was extracted with ethyl acetate. The organic combined extract was further washed with water, brine, dried (MgSO$_4$), filtered and evaporated. The residue was used as this in the next step. $^1$H-NMR (300 MHz, CDCl$_3$): 1.39 (s, 6H), 1.97 (t, J=6.2 Hz, 1H), 3.63 (t, J=4.4 Hz, 2H), 3.79 (m, 2H), 4.26 (s, 2H), 4.54 (s, 2H), 7.15 (d, J=8.5 Hz, 2H), 7.49 (d, J=8.8 Hz, 1H), 7.91 (dd, J$_1$=8.8 Hz, J$_2$=2.1 Hz, 1H), 8.02 (d, J=2.1 Hz, 1H), 10.03 (s, 1H).

b. 2-[7-(5-[1,3]Dioxolan-2-yl-2-trifluoromethoxy-phenyl)-3,3-dimethyl-2,3-dihydro-benzofuran-5-ylmethoxy]-ethanol.

A mixture of 3-(5-hydroxymethyl-3,3-dimethyl-2,3-dihydro-benzofuran-7-yl)-4-trifluoromethoxy-benzaldehyde (1.76 g, 4.82 mmol) and 12N HCl (12 mL) in toluene (45 mL) was heated at reflux for 1 hour. The solution was cooled to room temperature and the layers were separated. The aqueous layer was extracted twice with ethyl acetate. The organic combined extract was washed with water, brine, dried (MgSO$_4$), filtered and evaporated. To the residue obtained (3-[5-chloromethyl-3,3-dimethyl-2,3-dihydro-benzofuran-7-yl]-4-trifluoromethoxy-benzaldehyde), diluted in toluene (20 mL), were added ethylene glycol (2.5 mL, 44.34 mmol) and p-toluenesulfonic acid monohydrate (0.44 mmol, 84 mg). The mixture was heated at reflux overnight using a Dean Stark apparatus. The solution was cooled to room temperature, poured into an aqueous solution of sodium bicarbonate, and extracted with ethyl acetate. The organic combined extract was washed with water, brine, dried (MgSO$_4$), filtered and evaporated. The residue was chromatographed on silica gel (50% ethyl acetate in hexane) to afford 830 mg of 2-[7-(5-[1,3]dioxolan-2-yl-2-trifluoromethoxy-phenyl)-3,3-dimethyl-2,3-dihydro-benzofuran-5-ylmethoxy]-ethanol. 38% yield. $^1$H-NMR (300 MHz, CDCl$_3$): 1.37 (s, 6H), 1.99 (t, J=6.2 Hz, 1H), 3.62 (t, J=4.5 Hz, 2H), 3.78 (m, 2H), 4.02–4.15 (m, 4H), 4.24 (s, 2H), 4.53 (s, 2H), 5.86 (s, 1H), 7.11 (d, J=8.5 Hz, 2H), 7.34 (d, J=8.5 Hz, 1H), 7.49 (d, J=8.5 Hz, 1H), 7.58 (s, 1H).

c. 3-(5-Hydroxymethyl-3,3-dimethyl-2,3-dihydro-benzofuran-7-yl)-4-trifluoromethoxy-benzaldehyde.

The intermediate 3-(5-hydroxymethyl-3,3-dihydro-benzofuran-7-yl)-4-trifluoromethoxy-benzaldehyde was prepared in a similar manner to example 1a using [3,3-dimethyl-7-(4,4,5,5-tetramethyl-[1,3,2]dioxaborolan-2-yl)-2,3-dihydro-benzofuran-5-yl]-methanol and 3-bromo-4-trifluoromethoxy benzaldehyde. 59% yield. $^1$H-NMR (300 MHz, CDCl$_3$): 1.39 (s, 6H), 1.71 (m, 1H), 4.26 (s, 2H), 4.68 (s, 2H), 7.14 (d, J=2.3 Hz, 1H), 7.21 (d, J=1.5 Hz, 1H), 7.49 (dd, J$_1$=8.5 Hz, J$_2$=1.5 Hz, 1H), 7.91 (dd, J$_1$=8.5 Hz, J$_2$=2.1 Hz, 1H), 8.01 (d, J=2.3 Hz, 1H), 10.03 (s, 1H).

d. [3,3-Dimethyl-7-(4,4,5,5-tetramethyl-[1,3,2]dioxaborolan-2-yl)-2,3-dihydro-benzofuran-5-yl]-methanol.

The intermediate [3,3-dimethyl-7-(4,4,5,5-tetramethyl-[1,3,2]dioxaborolan-2-yl)-2,3-dihydro-benzofuran-5-yl]-methanol was prepared in a similar manner to example 5b using 7-bromo-3,3-dimethyl-2,3-dihydro-benzofuran-5-carbaldehyde (example 3c). 55% yield. $^1$H-NMR (300 MHz, CDCl$_3$): 1.33 (s, 6H), 1.36 (s, 12H), 1.55 (m, 1H), 4.33 (s, 2H), 4.61 (br s, 2H), 7.23 (d, J=2.1 Hz, 1H), 7.52 (d, J=8.5 Hz, 1H).

e. 3-[5-Chloromethyl-3,3-dimethyl-2,3-dihydro-benzofuran-7-yl]-4-trifluoromethoxy-benzaldehyde.

$^1$H-NMR (300 MHz, CDCl$_3$): 1.40 (s, 6H), 4.28 (s, 2H), 4.63 (s, 2H), 7.20 (m, 2H), 7.50 (d, J=8.5 Hz, 1H), 7.93 (dd, J$_1$=8.5 Hz, J$_2$=2.1 Hz, 1H), 8.02 (d, J=2.1 Hz, 1H), 10.04 (s, 1H).

Example 11

5-[3-(5-Methoxymethyl-3,3-dimethyl-2,3-dihydro-benzofuran-7-yl)-4-trifluoromethoxy-benzylidene]-thiazolidine-2,4-dione, which can be referred to as "Compound 11"

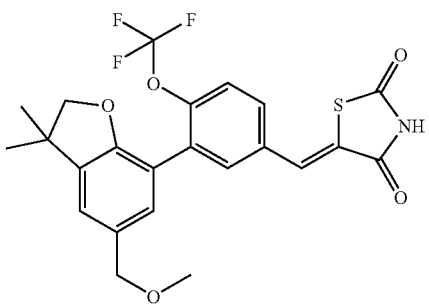

Prepared in a similar manner to example 1 using 3-(5-Methoxymethyl-3,3-dimethyl-2,3-dihydro-benzofuran-7-yl)-4-trifluoromethoxy-benzaldehyde. 78% yield, mp 148–151° C. $^1$H-NMR (300 MHz, CDCl$_3$): 1.40 (s, 6H), 2.11 (s, 3H), 4.28 (s, 2H), 5.09 (s, 2H), 7.17 (s, 2H), 7.44 (d, J=8.8 Hz, 1H), 7.51 (dd, J$_1$=8.8 Hz, J$_2$=2.1 Hz, 1H), 7.65 (d, J=2.1 Hz, 1H), 7.86 (s, 1H), 8.44 (br s, 1H).

The intermediate 3-(5-Methoxymethyl-3,3-dimethyl-2,3-dihydro-benzofuran-7-yl)-4-trifluoromethoxy-benzaldehyde was prepared as follows:

a. 3-(5-Methoxymethyl-3,3-dimethyl-2,3-dihydro-benzofuran-7-yl)-4-trifluoromethoxy-benzaldehyde.

To a cold solution (0° C.) of sodium hydride in tetrahydrofuran (4 mL), under an atmosphere of argon, was added 3-(5-hydroxymethyl-3,3-dimethyl-2,3-dihydro-benzofuran-7-yl)-4-trifluoromethoxy-benzaldehyde (example 10c) (246 mg, 0.67 mmol) in tetrahydrofuran (6 mL). The mixture was stirred at 0° C. for 15 minutes, then the argon flow was stopped and methyl iodide was added. After 3 hours at room temperature, the mixture was diluted with ethyl acetate. Water was slowly added and the layers separated. The organic layer was further washed with water, brine, dried (MgSO$_4$), filtered and evaporated. The residue was chromatographed on silica gel (20% ethyl acetate in hexane) to afford 99 mg of 3-(5-Methoxymethyl-3,3-dimethyl-2,3-dihydro-benzofuran-7-yl)-4-trifluoromethoxy-benzaldehyde. 39% yield. $^1$H-NMR (300 MHz, CDCl$_3$): 1.39 (s, 6H), 2.11 (s, 3H), 4.27 (s, 2H), 5.09 (s, 2H), 7.17 (s, 2H), 7.49 (d, J=8.5 Hz, 1H), 7.93 (dd, J$_1$=8.5 Hz, J$_2$=2.1 Hz, 1H), 8.02 (d, J=2.1 Hz, 1H), 10.03 (s, 1H).

Example 12

7-[5-(2,4-Dioxo-thiazolidin-5-ylidenemethyl)-2-trifluoromethoxy-phenyl]-3,3-dimethyl-2,3-dihydro-benzofuran-5-carboxylic acid, which can be referred to as "Compound 12"

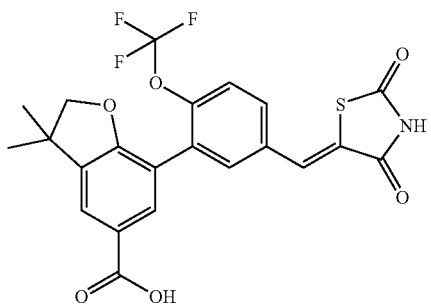

Prepared in a similar manner to example 1 using 7-(5-formyl-2-trifluoromethoxy-phenyl)-3,3-dimethyl-2,3-dihydro-benzofuran-5-carboxylic acid. 35% yield, mp 223–226° C. $^1$H-NMR (300 MHz, DMSO-d-6): 1.36 (s, 6H), 4.33 (s, 2H), 7.62 (d, J=8.5 Hz, 1H), 7.74 (d, J=8.5 Hz, 1H), 7.80 (d, J=5.3 Hz, 2H), 7.86 (s, 2H), 12.71 (br s, 1H), 12.77 (br s, 1H).

The intermediate 7-(5-formyl-2-trifluoromethoxy-phenyl)-3,3-dimethyl-2,3-dihydro-benzofuran-5-carboxylic acid was prepared as follows:

a. 7-(5-Formyl-2-trifluoromethoxy-phenyl)-3,3-dimethyl-2,3-dihydro-benzofuran-5-carboxylic acid.

A mixture of 7-(5-Formyl-2-trifluoromethoxy-phenyl)-3,3-dimethyl-2,3-dihydro-benzofuran-5-carboxylic acid methyl ester (1.76 g, 4.82 mmol) (example 8) and 5N potassium hydroxide (2 mL) in methanol (20 mL) was heated at reflux for 1 hour. The solvent was then evaporated. The mixture was diluted with water and washed twice with diethyl ether. The aqueous layers were acidified with 1N HCl and extracted twice with ethyl acetate. The organic combined extract was further washed with water, brine, dried (MgSO$_4$), filtered and evaporated. The residue was chromatographed on silica gel (30% ethyl acetate in hexane) to afford 112 mg of 7-(5-formyl-2-trifluoromethoxy-phenyl)-3,3-dimethyl-2,3-dihydro-benzofuran-5-carboxylic acid. 10% yield. $^1$H-NMR (300 MHz, CDCl$_3$): 1.43 (s, 6H), 4.36 (s, 2H), 7.51 (d, J=8.2 Hz, 1H), 7.92–8.04 (m, 4H), 10.05 (s, 1H).

Example 13

5-[3-(5-Dimethylaminomethyl-3,3-dimethyl-2,3-dihydro-benzofuran-7-yl)-4-trifluoromethoxy-benzylidene]-thiazolidine-2,4-dione, which can be referred to as "Compound 13"

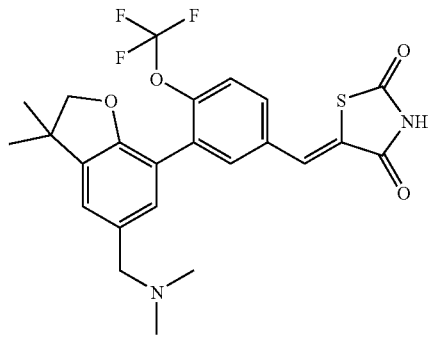

Prepared in a similar manner to example 1 using 3-(5-Dimethylaminomethyl-3,3-dimethyl-2,3-dihydro-benzofuran-7-yl)-4-trifluoromethoxy-benzaldehyde. 65% yield, mp 233–235° C. $^1$H-NMR (300 MHz, DMSO-d-6): 1.34 (s, 6H), 2.57 (s, 6H), 4.00 (s, 2H), 4.26 (s, 2H), 7.22 (d, J=1.8 Hz, 1H), 7.33 (d, J=1.7 Hz, 1H), 7.49 (s, 1H), 7.53 (d, J=7.9 Hz, 1H), 7.67 (dd, J$_1$=7.9 Hz, J$_2$=2.3 Hz, 1H), 7.69 (s, 1H).

The intermediate 3-(5-dimethylaminomethyl-3,3-dimethyl-2,3-dihydro-benzofuran-7-yl)-4-trifluoromethoxy-benzaldehyde was prepared as follows:

a. 3-(5-Dimethylaminomethyl-3,3-dimethyl-2,3-dihydro-benzofuran-7-yl)-4-trifluoromethoxy-benzaldehyde.

A mixture of 3-(5-hydroxymethyl-3,3-dimethyl-2,3-dihydro-benzofuran-7-yl)-4-trifluoromethoxy-benzaldehyde (1.25 g, 3.41 mmol) (example 10c) and 12N HCl (8.5 mL) in toluene (35 mL) was heated at reflux for 1 hour. The solution was cooled to room temperature and the layers were separated. The aqueous layer was extracted twice with ethyl acetate. The organic combined extract was washed with water, brine, dried (MgSO$_4$), filtered and evaporated. To the residue obtained (3-[5-chloromethyl-3,3-dimethyl-2,3-dihydro-benzofuran-7-yl)-4-trifluoromethoxy-benzaldehyde) (example 10e), diluted in dimethylformamide (35 mL), were added potassium carbonate (3.49 g, 25.25 mmol) then dimethylamine hydrochloride (1.47 g, 18.04 mmol). The mixture was stirred at room temperature for 3 hours. Water was added and the layers separated. The mixture was extracted with ethyl acetate and the organic combined extract was washed with water, brine, dried (MgSO$_4$), filtered and evaporated. The residue was chromatographed on silica gel (10% methanol in dichloromethane) to afford 742 mg of 3-(5-Dimethylaminomethyl-3,3-dimethyl-2,3-dihydro-benzofuran-7-yl)-4-trifluoromethoxy-benzaldehyde. 56% yield. $^1$H-NMR (300 MHz, CDCl$_3$): 1.38 (s, 6H), 2.30 (s, 6H), 3.47

(s, 2H), 4.25 (s, 2H), 7.06 (s, 1H), 7.16 (s, 1H), 7.48 (d, J=8.5 Hz, 1H), 7.90 (dd, J$_1$=8.5 Hz, J$_2$=2.1 Hz, 1H), 8.03 (d, J=2.1 Hz, 1H), 10.03 (s, 1H).

Example 14

7-[5-(2,4-Dioxo-thiazolidin-5-ylidenemethyl)-2-trifluoromethoxy-phenyl]-3,3-dimethyl-2,3-dihydro-benzofuran-5-sulfonic acid Methylamide, which can be referred to as "Compound 14"

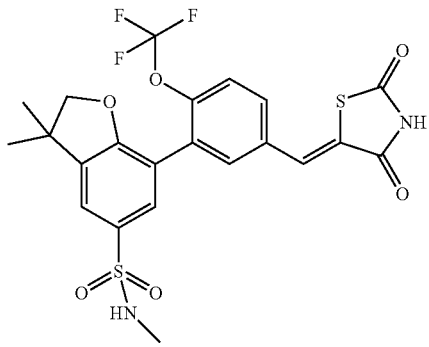

Prepared in a similar manner to example 1 using 7-(5-formyl-2-trifluoromethoxy-phenyl)-3,3-dimethyl-2,3-dihydro-benzofuran-5-sulfonic acid methylamide. 45% yield. $^1$H-NMR (300 MHz, DMSO-d-6): 1.38 (s, 6H), 2.43 (d, J=5.0 Hz, 3H), 4.37 (s, 2H), 7.32 (q, J=5.0 Hz, 1H), 7.59 (d, J=1.8 Hz, 1H), 7.65 (dd, J$_1$=8.8 Hz, J$_2$=1.5 Hz, 1H), 7.69 (d, J=1.8 Hz, 1H), 7.76 (dd, J$_1$=8.8 Hz, J$_2$=2.3 Hz, 1H), 7.83 (d, J=2.1 Hz, 1H), 7.88 (s, 1H), 12.72 (br s, 1H).

The intermediate 7-(5-formyl-2-trifluoromethoxy-phenyl)-3,3-dimethyl-2,3-dihydro-benzofuran-5-sulfonic acid methylamide was prepared in a similar manner to example 2a using 7-bromo-3,3-dimethyl-2,3-dihydro-benzofuran-5-sulfonic acid methylamide and 3-formyl-6-trifluoromethoxy-1-phenyl boronic acid (example 2b). 90% yield. $^1$H-NMR (300 MHz, CDCl$_3$): 1.43 (s, 6H), 2.70 (d, J=5.6 Hz, 3H), 4.31 (m, 1H), 4.37 (s, 2H), 7.52 (dd, J$_1$=8.5 Hz, J$_2$=1.8 Hz, 1H), 7.66 (d, J=2.1 Hz, 1H), 7.71 (d, J=2.1 Hz, 1H), 7.97 (dd, J$_1$=8.5 Hz, J$_2$=2.1 Hz, 1H), 8.03 (d, J=2.1 Hz, 1H), 10.05 (s, 1H).

a. 7-Bromo-3,3-dimethyl-2,3-dihydro-benzofuran-5-sulfonic acid methylamide.

To a solution of 3,3-dimethyl-2,3-dihydro-benzofuran-5-sulfonic acid methylamide (215 mg, 0.89 mmol) in trifluoroacetic acid (5 mL) and sulfuric acid (1 mL) was added portionwise N-bromosuccinimide (317 mg, 1.78 mmol). The mixture was stirred at room temperature overnight, poured into a solution of ice-water and rinsed with dichloromethane. The layers were separated. The aqueous layer was extracted twice with dichloromethane and the organic combined extract was washed with water, an aqueous solution of sodium bicarbonate, brine, dried (MgSO$_4$), filtered and evaporated. The residue was chromatographed on silica gel (30% ethyl acetate in hexane) to afford 91 mg of 7-bromo-3,3-dimethyl-2,3-dihydro-benzofuran-5-sulfonic acid methylamide. 32% yield. $^1$H-NMR (300 MHz, CDCl$_3$): 1.40 (s, 6H), 2.68 (d, J=5.3 Hz, 3H), 4.21 (m, 1H), 4.45 (s, 2H), 7.52 (d, J=1.8 Hz, 1H), 7.83 (d, J=1.8 Hz, 1H).

b. 3,3-Dimethyl-2,3-dihydro-benzofuran-5-sulfonic acid methylamide.

To a solution of 3,3-dimethyl-2,3-dihydro-benzofuran (160 mg, 1.08 mmol) in dichloromethane (2 mL) at −10° C. was added chlorosulfonic acid (72 µL, 1.08 mmol). The mixture was stirred at −10° C. for 15 minutes, then the solvent was evaporated to give 3,3-dimethyl-2,3-dihydro-benzofuran-5-sulfonic acid [$^1$H-NMR (300 MHz, CDCl$_3$): 1.37 (s, 6H), 4.35 (s, 2H), 6.85 (d, J=8.2 Hz, 1H), 7.67 (d, J=2.1 Hz, 1H), 7.73 (dd, J$_1$=8.5 Hz, J$_2$=2.1 Hz, 1H), 10.12 (br s, 1H)]. The residue was diluted with thionyl chloride (1 mL, 13.71 mmol) and one drop of dimethylformamide was added. After 45 minutes reflux and evaporation of the solvent, the solid compound was washed in a mixture of dichloromethane/hexane to give 3,3-dimethyl-2,3-dihydro-benzofuran-5-sulfonyl chloride [$^1$H-NMR (300 MHz, CDCl$_3$): 1.41 (s, 6H), 4.41 (s, 2H), 6.92 (d, J=8.8 Hz, 1H), 7.74 (d, J=2.3 Hz, 1H), 7.87 (dd, J$_1$=8.5 Hz, J$_2$=2.1 Hz, 1H)]. A solution of methylamine 2.0 M in tetrahydrofuran (0.81 mL, 1.62 mmol) was then slowly added and the mixture was stirred at room temperature for 15 minutes. The solvent was evaporated to afford 215 mg of 3,3-dimethyl-2,3-dihydro-benzofuran-5-sulfonic acid methylamide. 83% yield. $^1$H-NMR (300 MHz, CDCl$_3$): 1.38 (s, 6H), 2.66 (d, J=5.3 Hz, 3H), 4.21 (m, 1H), 4.34 (s, 2H), 6.86 (d, J=8.5 Hz, 1H), 7.60 (d, J=2.1 Hz, 1H), 7.66 (dd, J$_1$=8.5 Hz, J$_2$=1.8 Hz, 1H).

c. 3,3-Dimethyl-2,3-dihydro-benzofuran.

To a solution of 5-bromo-3,3-dimethyl-2,3-dihydro-benzofuran (example 1f) (3.3 g, 14.53 mmol) in tetrahydrofuran (30 mL) was added dropwise, at −78° C., under an atmosphere of argon, a solution of n-butyllithium in hexane (8.8 mL, 22 mmol). The mixture was stirred at −78° C. for 5 minutes, then water was added and the mixture was warmed up to room temperature and stirred for 30 minutes. The layers were separated. The aqueous layer was extracted twice with ethyl acetate and the organic combined extract was washed with water, brine, dried (MgSO$_4$), and filtered. The solvent was evaporated to afford 2.13 g of 3,3-dimethyl-2,3-dihydro-benzofuran. 99% yield. $^1$H-NMR (300 MHz, CDCl$_3$): 1.35 (s, 6H), 4.23 (s, 2H), 6.79 (d, J=7.6 Hz, 1H), 6.88 (t, J=7.3 Hz, 1H), 7.11 (d, J=7.6 Hz, 2H).

Example 15

5-[3-(5-Methanesulfonyl-3,3-dimethyl-2,3-dihydro-benzofuran-7-yl)-4-trifluoromethoxy-benzylidene]-thiazolidine-2,4-dione, which can be referred to as "Compound 15"

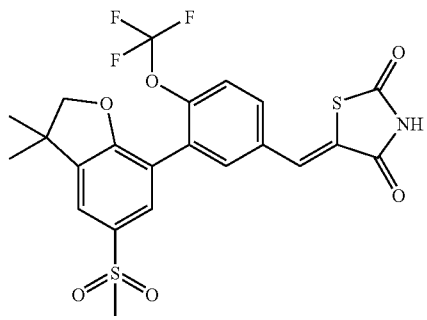

Prepared in a similar manner to example 1 using 3-(5-methanesulfonyl-3,3-dimethyl-2,3-dihydro-benzofuran-7- yl)-4-trifluoromethoxy-benzaldehyde. 22% yield, mp 215–227° C. $^1$H-NMR (300 MHz, DMSO-d-6): 1.39 (s, 6H), 3.23 (s, 3H), 4.38 (s, 2H), 7.62–7.68 (m, 1H), 7.74–7.79 (m, 2H), 7.86–7.89 (m, 3H), 12.72 (br s, 1H).

The intermediate 3-(5-methanesulfonyl-3,3-dimethyl-2,3-dihydro-benzofuran-7-yl)-4-trifluoromethoxy-benzaldehyde was prepared in a similar manner to example 2a using 7-bromo-5-methanesulfonyl-3,3-dimethyl-2,3-dihydro-benzofuran and 3-formyl-6-trifluoromethoxy-1-phenyl boronic acid (example 2b). 30% yield. $^1$H-NMR (300 MHz, CDCl$_3$): 1.44 (s, 6H), 3.10 (s, 3H), 4.38 (s, 2H), 7.52 (d, J=8.8 Hz, 1H), 7.73 (d, J=2.1 Hz, 1H), 7.79 (d, J=2.1 Hz, 1H), 7.98 (dd, J$_1$=8.5 Hz, J$_2$=2.1 Hz, 1H), 8.02 (d, J=2.1 Hz, 1H), 10.06 (s, 1H).

The intermediate 7-bromo-5-methanesulfonyl-3,3-dimethyl-2,3-dihydro-benzofuran was prepared in a similar manner to example 14a using 5-methanesulfonyl-3,3-dimethyl-2,3-dihydro-benzofuran. 27% yield. $^1$H-NMR (300 MHz, CDCl$_3$): 1.41 (s, 6H), 3.06 (s, 3H), 4.46 (s, 2H), 7.60 (d, J=1.8 Hz, 1H), 7.92 (d, J=1.8 Hz, 1H).

a. 5-Methanesulfonyl-3,3-dimethyl-2,3-dihydro-benzofuran.

A mixture of 3,3-dimethyl-2,3-dihydro-benzofuran (example 14c) (870 mg, 5.87 mmol), trifluoromethanesulfonic acid (0.1 mL, 1.17 mmol) and methanesulfonic anhydride (2.04 g, 11.74 mmol) was heated to 135° C. After reaching this temperature, the heater was removed and the mixture was cooled down to room temperature. The mixture was poured into a solution of ice-water. The aqueous layer was extracted twice with ethyl acetate and the organic combined extract was washed with water, an aqueous solution of sodium bicarbonate, brine, dried (MgSO$_4$), filtered, and evaporated. The residue was chromatographed on silica gel (30% to 50% ethyl acetate in hexane) to afford 317 mg of 5-Methanesulfonyl-3,3-dimethyl-2,3-dihydro-benzofuran. 24% yield. $^1$H-NMR (300 MHz, CDCl$_3$): 1.39 (s, 6H), 3.04 (s, 3H), 4.36 (s, 2H), 6.90 (d, J=8.2 Hz, 1H), 7.67 (d, J=2.1 Hz, 1H), 7.74 (dd, J$_1$=8.5 Hz, J$_2$=2.1 Hz, 1H).

Example 16

5-[3-(5-Acetyl-3,3-dimethyl-2,3-dihydro-benzofuran-7-yl)-4-trifluoromethoxy-benzylidene]-thiazolidine-2,4-dione, which can be referred to as "Compound 16"

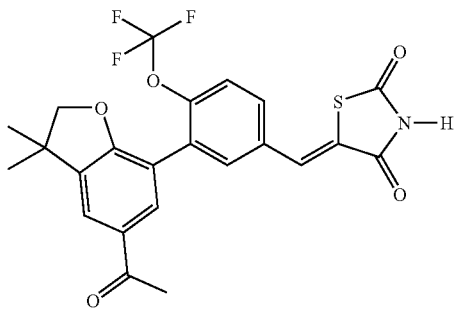

Prepared in a similar manner to example 1 using 3-(5-acetyl-3,3-dimethyl-2,3-dihydro-benzofuran-7-yl)-4-trifluoromethoxy-benzaldehyde. (yield: 66%). $^1$H-NMR (300 MHz, DMSO-d-6): $^1$H NMR(DMSO-d$_6$, ppm) 1.37 (s, 6H), 2.57 (s, 3H), 4.34 (s, 2H), 7.62–7.65 (m, 1H), 7.73–7.77 (m, 1H), 7.83–7.85 (m, 2H), 7.87 (s, 1H), 7.92 (m, 1H), 12.71 (bs, 1H).

The intermediate 3-(5-acetyl-3,3-dimethyl-2,3-dihydro-benzofuran-7-yl)-4-trifluoromethoxy-benzaldehyde was prepared as follows:

a. 3-(5-acetyl-3,3-dimethyl-2,3-dihydro-benzofuran-7-yl)-4-trifluoromethoxy-benzaldehyde.

1-(7-Bromo-3,3-dimethyl-2,3-dihydro-benzofuran5-yl)-ethanone (925 mg, 3.44 mmol) and 3-formyl-6-trifluoromethoxy-1-phenyl boronic acid (example 2b) (1207 mg, 5.16 mmol) were mixed with toluene (30 mL), EtOH (6 mL) and water (4 mL). Argon was bubbled through the mixture for 20 minutes before adding tetrakis(triphenylphosphine) palladium(0) (398 mg, 0.34 mmol) and potassium carbonate (951 mg, 6.88 mmol). The mixture was heated to reflux under argon for 15 hours then cooled to room temperature and water (20 mL) was added. The mixture was extracted with EtOAc, washed with brine, dried over MgSO$_4$, filtered and evaporated under reduced pressure. The residue was purified by column chromatography on silica gel (hexane: EtOAc/6:1) to give 1.08 g of 3-(5-acetyl-3,3-dimethyl-2,3-dihydro-benzofuran-7-yl)-4-trifluoromethoxy-benzaldehyde (83%). $^1$H NMR (300 MHz, CDCl$_3$, ppm): δ: 1.42 (s, 6H), 2.59 (s, 3H), 4.35 (s, 2H), 7.50–7.54 (m, 1H), 7.82 (d, J=1.76 Hz, 1H), 7.84 (d, J=1.76 Hz, 1H), 7.95 (dd, J$_1$=2.05 Hz, J$_2$=5.57 Hz, 1H), 8.03 (d, J=2.05 Hz), 10.05 (s, 1H).

b. 1-(7-Bromo-3,3-dimethyl-2,3-dihydro-benzofuran5-yl)-ethanone.

To a solution of 1-(3,3-dimethyl-2,3-dihydro-benzofuran5-yl)-ethanone (1.69 g, 8.88 mmol) in dichloromethane (25 mL) was slowly added a suspension of AlCl$_3$ (2.96 g, 22.2 mmol) in dichloromethane (30 mL). Bromine (1.61 g, 10.7 mmol) was added dropwise and the mixture was stirred at room temperature for 6 hours then cooled to 0° C. and aqueous HCl (1N) was added and the mixture extracted with dichloromethane, washed with brine, dried over MgSO$_4$, filtered and evaporated under reduced pressure. The residue was purified by column chromatography on silica gel (hexane: EtOAc/10:1 to 2:1) to give 1.94 g 1-(7-Bromo-3,3-dimethyl-2,3-dihydro-benzofuran5-yl)-ethanone (81%). $^1$H NMR (300 MHz, CDCl$_3$, ppm): δ: 1.39 (s, 6H), 2.56 (s, 3H), 4.37 (s, 2H), 7.69 (d, J=1.76 Hz, 1H), 7.95 (d, J=1.76 Hz, 1H).

c. 1-(3,3-dimethyl-2,3-dihydro-benzofuran5-yl)-ethanone.

To a solution of i-(3,3-dimethyl-2,3-dihydro-benzofuran5-yl)-ethanol (3.39 g, 15.4 mmol) in dichloromethane (100 mL), was added at 0° C. pyridinium chlorochromate (4.32 g, 20 mmol) and the mixture was stirred at room temperature for 4 hours then filtered through Celite. The filtrate was washed with brine, dried over MgSO$_4$, filtered and evaporated under reduced pressure. The residue was purified by column chromatography on silica gel (hexane: EtOAc/5:1 to 3:1) to give 1.69 g of 1-(3,3-dimethyl-2,3-dihydro-benzofuran5-yl)-ethanone (58%). $^1$H NMR (300 MHz, CDCl$_3$, ppm): δ: 1.37 (s, 6H), 2.56 (s, 3H), 4.32 (s, 2H), 6.80 (m, 1H), 7.78–7.82 (m, 2H).

d. 1-(3,3-dimethyl-2,3-dihydro-benzofuran5-yl)-ethanol.

To a solution of 5-bromo-3,3-dimethyl-2,3-dihydro-benzofuran (example 1f) (3.50 g, 15.4 mmol) in dry THF (20 mL) at −78° C., under argon, was added dropwise n-BuLi (1.6 M in hexane, 23.1 mmol, 14.4 mL). The mixture was stirred for 2 hours then acetaldehyde (0.95 mL) was added and the mixture was slowly warmed up to room temperature and stirred overnight at room temperature. 1N HCl was added and the solution extracted with ethyl acetate and the organic extract was dried (MgSO$_4$), filtered and evaporated to give 3.3 g of 1-(3,3-dimethyl-2,3-dihydro-benzofuran5-yl)-ethanol. $^1$H NMR (300 MHz; CDCl$_3$): δ 1.35 (s, 6H), 1.49 (d, J=6.5 Hz, 3H), 4.24 (s, 2H), 4.86 (q, J=6.5 Hz, 1H), 6.75 (d, J=8.2 Hz, 3H), 7.10–7.15 (m, 2H).

Example 17

5-[3-(5-Isoxazol-5-yl-3,3-dimethyl-2,3-dihydro-benzofuran-7-yl)-4-trifluoromethoxy-benzylidene]-thiazolidine-2,4-dione, which can be referred to as "Compound 17"

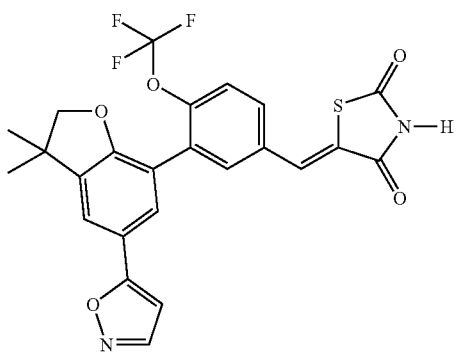

Prepared in a similar manner to example 1 using 3-(5-Isoxazol-5-yl-3,3-dimethyl-2,3-dihydro-benzofuran-7-yl)-4-trifluoromethoxy-benzaldehyde. (yield: 51%). $^1$H NMR (DMSO-d$_6$, ppm) 1.37 (s, 6H), 4.23 (s, 2H), 6.92 (s, 1H), 7.61–7.70 (m, 3H), 7.84 (m, 3H), 8.59 (s, 1H), 12.69 (bs, 1H).

The intermediate 3-(5-Isoxazol-5-yl-3,3-dimethyl-2,3-dihydro-benzofuran-7-yl)-4-trifluoromethoxy-benzaldehyde was prepared as follows:

a. 3-(5-Isoxazol-5-yl-3,3-dimethyl-2,3-dihydro-benzofuran-7-yl)-4-trifluoromethoxy-benzaldehyde.

3-(5-acetyl-3,3-dimethyl-2,3-dihydro-benzofuran-7-yl)-4-trifluoromethoxy-benzaldehyde(example 16a) (780 mg, 2.06 mmol), ethylene glycol (2.56 g, 41.2 mmol) and p-toluenesulfonic acid monohydrate (24 mg, 0.12 mmol) were mixed with toluene (10 mL) in a flask equipped with a Dean-Stark trap. The mixture was heated to reflux for 3 hours then cooled to room temperature and water was added. The solution was extracted with EtOAc, washed with 1N HCl, brine, dried over MgSO$_4$, filtered and evaporated under reduced pressure to give 850 mg of 1-[7-(5-[1,3]dioxolan-2-yl-2-trifluoromethoxy-phenyl)-3,3-dimethyl-2,3-dihydro-benzofuran-5-yl]-ethanone used as this in the next step.

1-[7-(5-[1,3]dioxolan-2-yl-2-trifluoromethoxy-phenyl)-3,3-dimethyl-2,3-dihydro-benzofuran-5-yl]-ethanone (850 mg) was mixed with N,N-dimethylformamide diethyl acetal (5 mL) in a dry flask under argon and heated to reflux for 24 hours. The solution was cooled to room temperature and excess of N,N-dimethylformamide diethyl acetal was removed under reduced pressure to afford 3-Dimethylamino-1-[7-(5-[1,3]dioxolan-2-yl-2-trifluoromethoxy-phenyl)-3,3-dimethyl-2,3-dihydro-benzofuran-5-yl]-propenone as a brown oil (1.1 g) use as this in the next step.

To a solution of 3-Dimethylamino-1-[7-(5-[1,3]dioxolan-2-yl-2-trifluoromethoxy-phenyl)-3,3-dimethyl-2,3-dihydro-benzofuran-5-yl]-propenone (1.1 g) in EtOH (10 mL) was added hydroxylamine hydrochloride (147 mg, 2.11 mmol).

The mixture was heated to reflux for 14 hours then cooled to room temperature and the solvent removed under reduced pressure. 15 mL of THF and 15 mL of 1N aqueous HCl were added and the solution was heated to reflux for 4 hours. The solution was then cooled to room temperature, extracted with EtOAc, washed with brine, dried over MgSO$_4$, filtered and evaporated under reduced pressure. The residue was purified by column chromatography on silica gel (hexane: EtOAc/10:1 to 5:1) to give 220 mg of 3-(5-Isoxazol-5-yl-3,3-dimethyl-2,3-dihydro-benzofuran-7-yl)-4-trifluoromethoxy-benzaldehyde (27% for the three steps). $^1$H NMR (300 MHz, CDCl$_3$, ppm): δ: 1.44 (s, 6H), 4.33(s, 2H), 6.42 (d, J=2.05 Hz, 1H), 7.49–7.54 (m, 1H), 7.60–7.62 (m, 2H), 7.96 (dd, J$_1$=2.05 Hz, J$_2$=8.50 Hz, 1H), 8.04 (d, J=2.05 Hz, 1H), 8.27 (d, J=2.05 Hz, 1H), 10.05 (s, 1H).

Example 18

5-[3-(6-isobutyl-benzo[1,3]dioxol-4-yl)-4-trifluoromethoxy-benzylidene]-thiazolidine-2,4-dione, which can be referred to as "Compound 18"

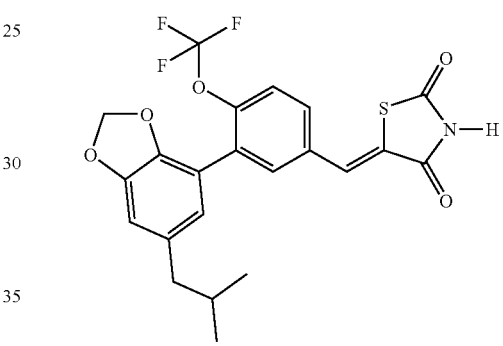

Prepared in a similar manner to example 1 using 3-(6-isobutyl-benzo[1,3]dioxol-4-yl)-4-trifluoromethoxy-benzaldehyde. $^1$H-NMR (300 MHz, CDCl$_3$): 0.94 (d, J=6.7 Hz, 6H), 1.86 (m, 1H), 2.46 (d, J=7.0 Hz, 2H), 5.99 (s, 2H), 6.68 (s, 1H), 7.72 (s, 1H), 7.46 (d, J=8.8 Hz, 1H), 7.53 (dd, J1 =8.8 Hz, J$_2$=2.3 Hz, 1H), 7.67 (d, J=2.1 Hz, 1H), 7.87 (s, 1H), 8.61 (s, 1H).

The intermediate 3-(6-isobutyl-benzo[1,3]dioxol-4-yl)-4-trifluoromethoxy-benzaldehyde was prepared as follows:

a. 3-(6-isobutyl-benzo[1,3]dioxol-4-yl)-4-trifluoromethoxy-benzaldehyde.

A mixture of 6-isobutyl-benzo[1,3]dioxole-4-boronic acid (110 mg, 0.50 mmol), 3-bromo-4-trifluoromethoxy benzaldehyde (example 1 h) (133 mg, 0.50 mmol), and potassium carbonate (137 mg, 0.99 mmol) in toluene (1.5 mL), ethanol (0.4 mL) and water (0.2 mL) was degassed with argon for 15 minutes.

Tetrakis(triphenylphosphine)palladium(0) (29 mg, 0.02 mmol) was added and the mixture heated at reflux under argon for 18 hrs. The solution was cooled to room temperature, diluted with ethyl acetate and washed successively with water and brine, dried over anhydrous magnesium sulfate, filtered and evaporated. The residue was purified on silica gel (5% ethyl acetate in hexane) to give 69 mg of 3-(6-isobutyl-benzo[1,3]dioxol-4-yl)-4-trifluoromethoxy-benzaldehyde. $^1$H NMR (300 MHz; CDCl$_3$): 0.92 (d, J=6.9 Hz, 6H), 1.84 (m, 1H), 2.45 (d, J=7.2 Hz, 2H), 5.96 (s, 2H), 6.65 (s, 1H), 6.70 (s, 1H), 7.50 (d, J=6.9 Hz, 1H), 7.92 (dd, J=2.1 Hz and 8.4 Hz, 1H), 8.18 (d, J=2.1 Hz, 1H), 10.04 (s, 1H).

b. 6-isobutyl-benzo[1,3]dioxole-4-boronic acid.

To a mixture of 4-bromo-6-isobutyl-benzo[1,3]dioxole (232 mg, 0.90 mmol) in THF (3 mL) cooled to −78° C. under an atmosphere of argon was added n-BuLi (0.72 mL, 2.5 M, 1.80 mmol) dropwise. The reaction mixture was stirred for 5 minutes and triisopropylborate (0.62 mL, 2.71 mmol) was added dropwise. The mixture was stirred at −50° C. for 2 hours then warmed up to room temperature and stirred overnight at room temperature. 2.0 N HCl was slowly added to the reaction mixture. After 30 minutes the mixture was diluted with ethyl acetate and the layers separated. The organic layer was further washed with water, brine, dried (MgSO$_4$), filtered and evaporated. The residue was chromatographed on silica gel (30% ethyl acetate in hexane) to give 110 mg of 6-isobutyl-benzo[1,3]dioxole-4-boronic acid (55%).

c. 4-bromo-6-isobutyl-benzo[1,3]dioxole.

To a solution of 7-bromo-benzo[1,3]dioxole-5-carbaldehyde (437 mg, 1.91 mmol) in dry ether (6 mL) was added slowly under argon at −30° C. isopropylmagnesium chloride (1.15 mL, 2.0 M in ether, 2.29 mmol) and the solution stirred for 30 minute. A solution of aqueous ammonium chloride was added and the layers separated. The aqueous layer was extrated with ethyl acetate and the organic combined and washed with water, brine, dried (MgSO$_4$), filtered and evaporated to give 503 mg of 1-(7-bromo-benzo[1,3]dioxol-5-yl)-2-methyl-propan-1-ol.

To a cold solution (0° C.) of 1-(7-bromo-benzo[1,3]dioxol-5-yl)-2-methyl-propan-1-ol (498 mg, 1.82 mmol) in dry dichloromethane (10 mL) was added triethylsilane (0.6 mL, 3.65 mmol). After 15 minutes, trifluoroacetic acid was added to the reaction and the mixture stirred at 0° C. for 45 minutes. Water was poured into the reaction mixture and the layers separated. The organic layer was further washed with water, aqueous NaHCO$_3$ and brine, dried (MgSO$_4$), filtered and evaporated. The residue was purified on silica gel (5% ethyl acetate in hexane) to give 242 mg of 4-bromo-6-isobutyl-benzo[1,3]dioxole (52%). $^1$H NMR (300 MHz; CDCl$_3$): δ 0.90 (d, J=6.3 Hz, 6H), 1.81 (m, 1H), 2.39 (d, J=7.5 Hz, 2H), 6.01 (s, 2H), 6.58 (s, 1H), 6.76 (s, 1H).

d. 7-bromo-benzo[1,3]dioxole-5-carbaldehyde.

To a solution of 3-bromo-5-hydroxy-4-methoxy-benzaldehyde (5.98 g, 25.89 mmol) in dichloromethane (200 mL) at −78° C., under argon, was added dropwise boron tribromide (4.9 mL, 51.79 mmol). The mixture was slowly warmed up to room temperature over 2 hours then poured into ice-water and extracted with ethyl acetate. The organic layer was further washed with water, dried (MgSO$_4$), filtered and evaporated. Crystallisation from ethyl acetate and hexane afford 4.4 g of 3-bromo-4,5-dihydroxy-benzaldehyde (78%).

To a solution of 3-bromo-4,5-dihydroxy-benzaldehyde (1.52 g, 7.02 mmol) in DMF (20 mL), were added KF (4.077 g, 70.18 mmol) followed by dibromomethane (1 mL, 14.04 mmol) and the mixture heated at 140° C. for 4 hours. The solution was cooled to room temperature, water was added and the mixture extracted with ether. The organic layer was further washed with saturated aqueous NaHCO$_3$, dried (MgSO$_4$), filtered and evaporated to give 973 mg of 7-bromo-benzo[1,3]dioxole-5-carbaldehyde. $^1$H NMR (300 MHz; CDCl$_3$): δ 6.16 (s, 2H), 7.26 (s, 1H), 7.54 (s, 1H), 9.76

Example 19

5-[3-(3,3-Dimethyl-5-oxazol-2-yl-2,3-dihydro-benzofuran-7-yl)-4-trifluoromethoxy-benzylidene]-thiazolidine-2,4-dione, which can be referred to as "Compound 19"

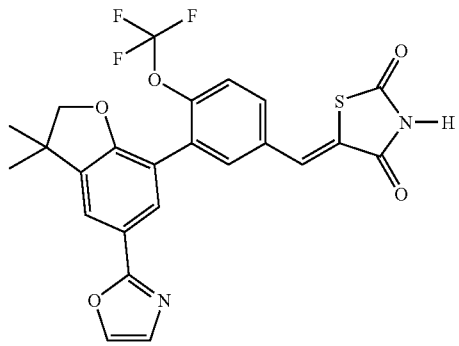

Prepared in a similar manner to example 1 using 3-(3,3-Dimethyl-5-oxazol-2-yl-2,3-dihydro-benzofuran-7-yl)-4-trifluoromethoxy-benzaldehyde. $^1$H-NMR (300 MHz, CDCl$_3$): 1.39 (s, 6H), 4.33 (s, 2H), 7.34 (m, 1H), 7.63–7.66 (m, 1H), 7.34–7.77 (m, 1H), 7.79 (d, J=1.76 Hz, 1H), 7.85 (d, J=2.1 Hz, 1H), 7.87 (s, 1H), 7.90 (d, J=1.5 Hz, 1H), 8.17 (m, 1H), 12.7 (bs, 1H).

The intermediate 3-(3,3-Dimethyl-5-oxazol-2-yl-2,3-dihydro-benzofuran-7-yl)-4-trifluoromethoxy-benzaldehyde was prepared as follows:

a. 3-(3,3-Dimethyl-5-oxazol-2-yl-2,3-dihydro-benzofuran-7-yl)-4-trifluoromethoxy-benzaldehyde.

To a solution of 2-(7-Bromo-3,3-dimethyl-2,3-dihydro-benzofuran-5-yl)-oxazole (550 mg, 1.87 mmol) in 1,4-dioxane (10 mL) flushed with Argon was added triethylamine (754 mg, 1.94 ml, 7.48 mmol), 2-(dicyclohexylphosphino) biphenyl (131 mg, 0.37 mmol), palladium(II) acetate(21 mg, 0.09 mmol) and 4,4,5,5-tetramethyl-1,3,2-dioxaborolane (718 mg, 0.82 mL, 5.61 mmol). The mixture was heated to 80° C. under argon for 2 hours and cooled to room temperature. Water (1 mL) was added followed by Ba(OH)$_2$.8H$_2$O (1.77 g, 5.05 mmol.), 3-bromo-4-trifluomethoxy-benzaldehyde (600 mg, 2.23 mmol), palladium(II) acetate (10 mg, 0.05 mmol) and 2-(dicyclohexylphosphino) biphenyl (65 mg, 0.18 mmol). The mixture was heated to reflux for 12 hours and cooled to room temperature. The solution was extracted with EtOAc, washed with brine, dried over MgSO$_4$, filtered and evaporated under reduced pressure. The residue was purified by column chromatography on silica gel (hexane: EtOAc/10:1 to 5: 1) to give 340 mg 3-(3,3-Dimethyl-5-oxazol-2-yl-2,3-dihydro-benzofuran-7-yl)-4-trifluoromethoxy-benzaldehyde (45%). $^1$H NMR (300 MHz, CDCl$_3$, ppm): δ: 1.44 (s, 6H), 4.33 (s, 2H), 7.21 (s, 1H), 7.50–7.53 (m, 1H), 7.68 (s, 1H), 7.88 (d, J=1.76 Hz, 1H), 7.89 (d, J=1.76 Hz, 1H), 7.96 (dd, J$_1$=2.05 Hz, J$_2$=8.50 Hz, 1H), 8.05 (d, J=2.34 Hz, 1H), 10.05 (s, 1H).

b. 2-(7-Bromo-3,3-dimethyl-2,3-dihydro-benzofuran-5-yl)-oxazole.

To a solution of 7-bromo-3,3-dimethyl-2,3-dihydrobenzofuran-5-carboxylic acid (example 3b) (1.8 g, 6.64 mmol) in dichloromethane (40 mL) was added several drops of DMF followed by a solution of thionyl chloride in dichloromethane (2.0M, 6.64 mL, 13.3 mmol) at 0° C. under argon. After the addition, the mixture was stirred at room temperature for 5 hours. The solvent and excess of thinoyl chloride were removed under reduced pressure. The residue was dissolved in tetramethylene sulfone (10 mL) and potassium carbonate (1.84 g, 13.3 mmol) and 1H-1,2,3-triazole (504 mg, 7.3 mmol) were added under argon and the mixture was heated to 140° C. for 16 hours. The solution was cooled to room temperature, water was added and the mixture was extracted with EtOAc, washed with brine, dried over $MgSO_4$, filtered and evaporated under reduced pressure. The residue was purified by column chromatography on silica gel (hexane: EtOAc/5:1) to give 900 mg of 2-(7-Bromo-3,3-dimethyl-2,3-dihydro-benzofuran-5-yl)-oxazole (46%). $^1$H NMR (300 MHz, $CDCl_3$, ppm): δ: 1.40 (s, 6H), 4.41 (s, 2H), 7.19 (s, 1H), 7.67 (s, 1H), 7.75 (d, J=0.88 Hz, 1H), 8.01 (d, J=0.88 Hz).

Example 20

5-[3-(3,5,5,8,8-Pentamethyl-5,6,7,8-tetrahydro-naphthalen-2-yl)-4-trifluoromethoxy-benzylidene]-thiazolidine-2,4-dione, which can be referred to as "Compound 20"

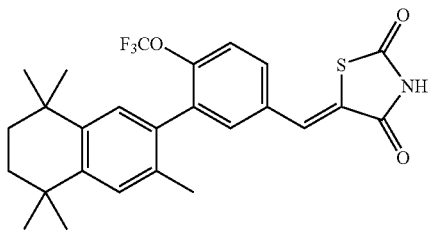

Compound 20 was disclosed in U.S. Pat. No. 6,515,003, issued Feb. 4, 2003, which is hereby incorporated by reference in it's entirety for its disclosures of the synthesis and biological activity of the Compound 20, which is employed herein for comparative purposes only.

Example 21

Differentiation of 3T3-L1 Pre-adipocytes in an In Vitro Assay

Mouse pre-adipocyte 3T3-L1 cells obtained from ATCC (American Tissue Culture Collection, MD) were initially grown in DME Dulbecco's modified Eagle's medium containing 4500 mg/L glucose; 4 mM L-glutamine; 10 U/ml Pen-G; 10 mcg/ml Streptomycin and 10% Bovine Calf Serum (CS) at 37° C. and 10% $CO_2$. Cells were plated in 96 well plates at a density of approximately 3,000 cells/well and grown to confluence (when cells use 100% of the available space on the well) in the same medium. Differentiation experiments were conducted two days after confluence in a differentiation medium (DM) consisting of DME Dulbecco's modified Eagle's medium containing 4500 mg/L glucose; 4 mM L-glutamine; 10 U/ml Pen-G; 10 mcg/ml Streptomycin and 10% Fetal Calf Serum (FCS) and 1 μg/mL of insulin. Cells were then treated with the test compound at a concentration of $10^{-10}$ to $10^{-6}$ M, or with a control for fully-differentiated adipocytes, such as Dexamethasone/Insulin (2.5 μM; 10 μg/ml, respectively). Differentiation medium containing the compounds, with no further addition of insulin, was replaced every 2–3 days for a total of 7 days. Compound 24 was used as a standard for differention activity, and its ability to differentiate 3T3-L1 cells at 0.1 μM was taken as reference for 100% differentiation. Upon termination of the experiments the treated cells were washed once with PBS (Phosphate Buffer Saline, Irvine Scientific, Irvine, Calif.) and lysed in situ with 50 μL 10% Hecameg (Detergent, Calbiochem, San Diego). The cellular lysates were analyzed for their lipid content using the Triglyceride-GPO Trinder reagent from Sigma. The compounds are compared against an internal standard known as 5-[3-(3,5,5,8,8-Pentamethyl-5,6,7,8-tetrahydro-naphthalen-2-yl)-4-trifluoromethoxy-benzylidene]-thiazolidine-2,4-dione (referred to as Compound 20 herein). As shown in FIG. 1, compounds of the invention induce differenciation of 3T3-L1 cells.

Example 22

Oral Administration of Compound of the Invention in the Treatment of Type 2 Diabetes in $KKA^y$ Mice Experimental Procedure: Six to eight week-old male $KKA^y$ mice (available from Jackson Labs of Bar Harbour, Me.) were housed in a fixed 12–12-hr artificial light-dark cycle, and maintained on a standard rodent diet provided ad libitum. Animals were allowed two days to acclimate in this experimental environment prior to the initiation of the study. Prior to initiation of treatment, the animals were bled from the tail vein (100–200 μL of whole blood) and serum levels of glucose and triglycerides were measured in duplicate (Trinder kits; Sigma, St.Louis, Mo.). Based on these initial measures, animals were sorted into groups with approximately the same average serum triglyceride levels. Once sorted, the animals were housed one per cage and provided rodent diet ad libitum.

Treatment group A (n=6/group):
1) $KKA^y$ control (sesame oil)
2) Compound 1 (15 mg/kg)
Treatment group B (n=6/group):
1) $KKA^y$ control (sesame oil)
2) Compound 6 (15 mg/kg)
Treatment group C (n=6/group):
1) $KKA^y$ control (sesame oil)
2) Compound 9 (15 mg/kg)

All compounds were suspended in sesame oil, and administered to animals in a volume of 3 ml/kg/dose. All treatments were administered by oral gavage once daily.

To monitor the effect of the tested Compounds, animals were bled at the end of the dark cycle on days 7 and/or 14 of the treatment period. Serum glucose and triglyceride levels were measured in duplicate. The blood was kept at room temperature to allow coagulation, after which the serum was separated and assayed for glucose and triglyceride levels. As shown in FIGS. 2 and 3, Compounds 1, 6 and 9 showed a reduction in both serum glucose and triglyceride levels when administered once a day.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the structure

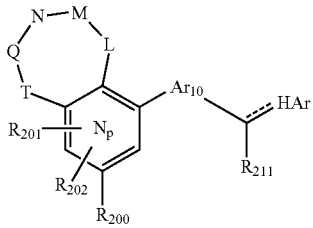

wherein:
a) p is 0, 1 or 2;
b) L, M, N, Q and T residues are independently selected from, —O—, —S(O)—, —S(O)—, —S(O)$_2$—, —N(R$_{203}$)—, —N(R$_{204}$)—, —C(R$_{205}$)(R$_{206}$)—, —C(R$_{207}$) (R$_{208}$)—, or —C(R$_{209}$)(R$_{210}$)— radicals, with the proviso that one or two of the L, M, N, Q or T radicals can be absent;
c) R$_{200}$, R$_{201}$, R$_{202}$, R$_{203}$, R$_{204}$, R$_{205}$, R$_{206}$, R$_{207}$, R$_{208}$, R$_{209}$, and R$_{210}$ are independently selected from hydrogen, hydroxyl, a halogen, amino, or an organic radical comprising 1 to 12 carbon atoms;
d) Ar10 is an aryl, substituted aryl, heteroaryl, or substituted heteroaryl radical comprising 2 to 18 carbon atoms;
e) the radical

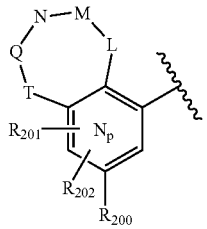

comprises from 6 to 20 carbon atoms;
f) R$_{211}$ is hydrogen, hydroxy, or an organic residue comprising 1 to 10 carbon atoms;
g) - - - is either present or absent; and
h) HAr has the structure

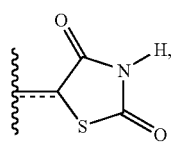 or 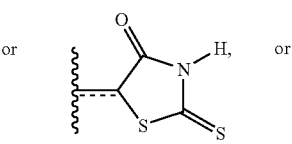

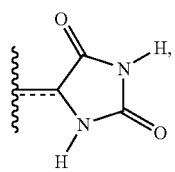

or a pharmaceutically acceptable salt thereof.

2. The compound of claim 1 wherein p is 0.

3. The compound of claim 1 wherein the radical

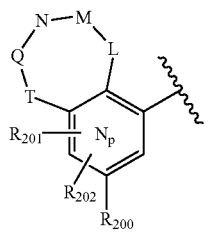

has the structure

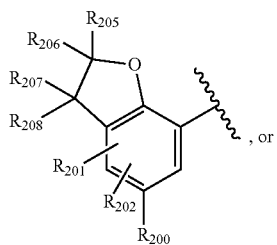, or

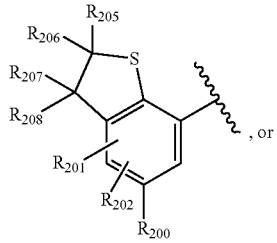, or

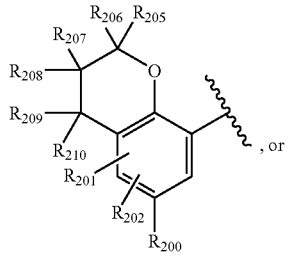, or

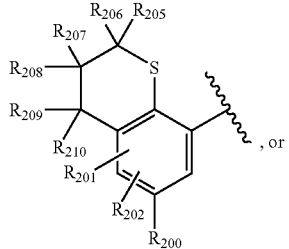, or

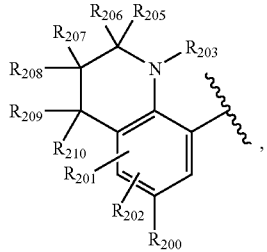,

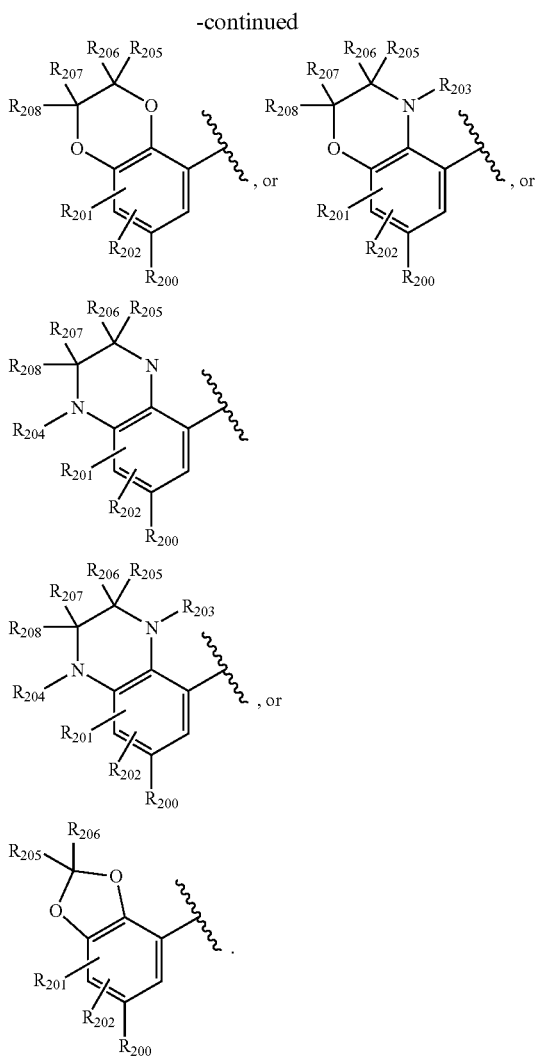

wherein $R_{200}$ comprises 1 to 8 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide;

$R_{201}$ and $R_{202}$ are independently selected from hydrogen or a halogen; and $R_{203}$, $R_{207}$ and $R_{208}$ are independently selected from hydrogen or an alkyl comprising 1 to 4 carbon atoms.

5. The compound of claim 1 wherein the radical has the structure wherein $R_{200}$ comprises 1 to 10 carbon atoms and is selected from an ailcyl, hydroxyalkyl, alkoxyalkyl, haloalkyl, halogen, cyano, nitro, hydroxyl, acyloxy, amino, mono-alkylamino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide.

6. The compound of claim 1 wherein the radical

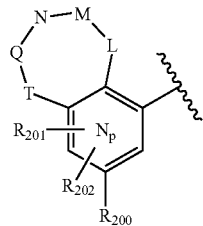

has the structure

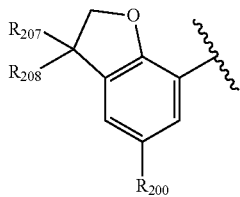

wherein $R_{200}$ comprises 1 to 4 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkyithiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide; and $R_{207}$ and $R_{208}$ are independently selected from hydrogen or an alkyl comprising 1 to 10 carbon atoms.

7. The compound of claim 4 wherein the $R_{207}$ and $R_{208}$, residues are connected together to form an exocyclic substituent residue comprising 3 to 6 ring carbon atoms and from 1 to 3 optional ring heteroatoms selected from O, S, or N.

8. The compound of claim 1 wherein the radical

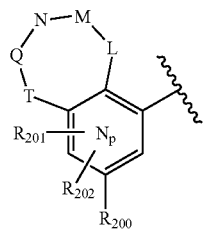

has the structure

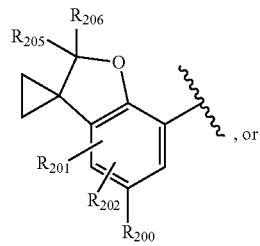

, or

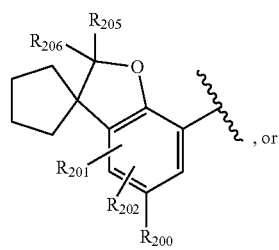

, or

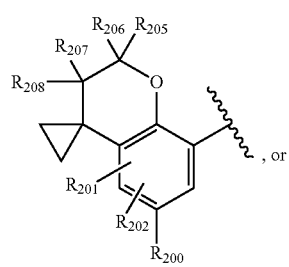

, or

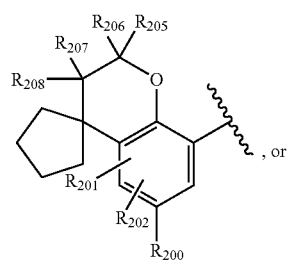

, or wherein $R_{200}$ comprises 1 to 10 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, substituted aryl, heteroaryl, substituted heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide; and $R_{201}$ and $R_{202}$ are independently selected from hydrogen or a halogen; and $R_{205}$, $R_{206}$, $R_{207}$, and $R_{208}$ are independently selected from hydrogen or an alkyl comprising 1 to 4 carbon atoms.

9. The compound of claim 1 wherein the radical

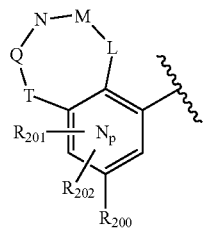

has the structure

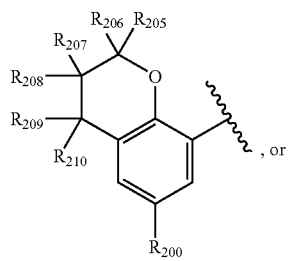, or

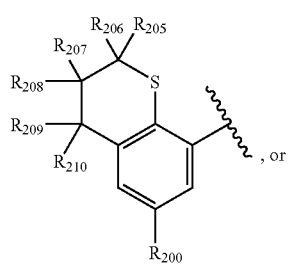, or

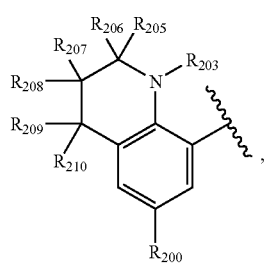, wherein $R_{200}$ comprises 1 to 10 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide; and $R_{205}$, $R_{206}$, $R_{207}$, $R_{208}$ $R_{209}$, and $R_{210}$ are independently selected from hydrogen or an alkyl comprising 1 to 4 carbon atoms.

10. The compound of claim 1 wherein the radical

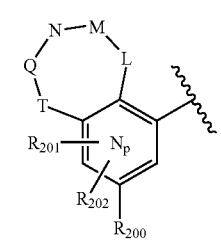

has the structure

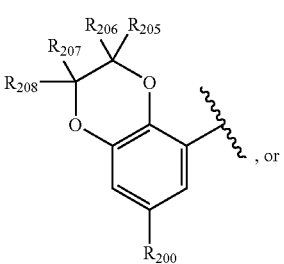, or

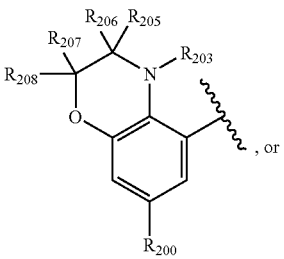, or

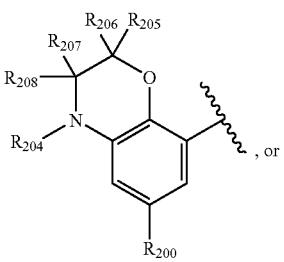, or

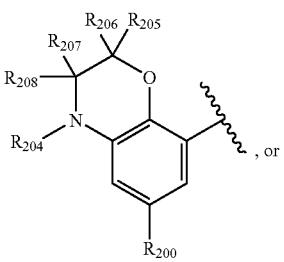, or

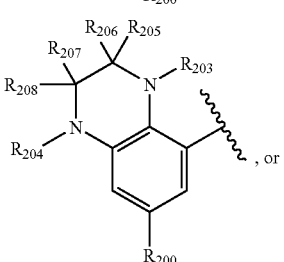, or

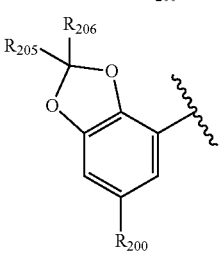

wherein $R_{200}$ comprises 1 to 10 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkyithiocarbamate, aryl, substituted aryl, heteroaryl, substituted heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide; and $R_{203}$, $R_{204}$, $R_{205}$, $R_{206}$, $R_{207}$, and $R_{208}$ are independently selected from hydrogen or an alkyl comprising 1 to 4 carbon atoms.

11. The compound of claim 1 wherein the radical

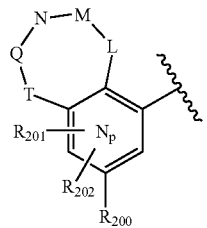

has the structure

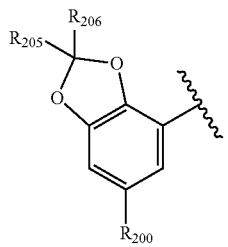

wherein $R_{200}$ comprises 1 to 10 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide; and $R_{205}$ and $R_{206}$ are independently selected from hydrogen or an alkyl comprising 1 to 4 carbon atoms.

12. The compound of claim 1 wherein p is 1 or 2.

13. The compound of claim 1 wherein the radical

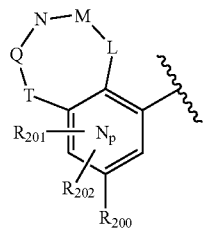

has the structure

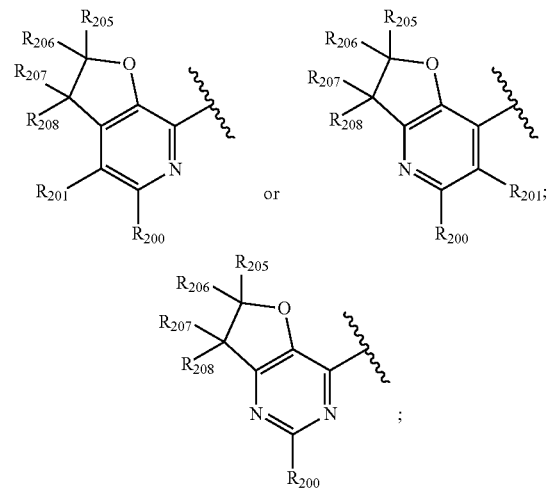

wherein $R_{200}$ comprises 1 to 10 carbon atoms and is selected from the group consisting of an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, substituted aryl, heteroaryl, substituted heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide, $R_{201}$ is hydrogen or a halide; and $R_{205}$, $R_{206}$, $R_{207}$, and $R_{208}$ are independently selected from hydrogen or an alkyl comprising 1 to 4 carbon atoms.

14. The compound of claim 1 wherein $R_{200}$ comprises to 8 carbon atoms and is selected from an alkyl, hydroxyalkyl, alkoxyalkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, alkoxy, haloalkoxy, thioalkyl, alkylsulfoxide, alkylsulfonyl, thiohaloalkyl, carboxy, carboalkoxy, alkylcarboxamide, or dialkylcarboxamide.

15. The compound of claim 1 wherein $R_{200}$ is an aryl, substituted aryl, heteroaryl, or substituted aryl having the structure

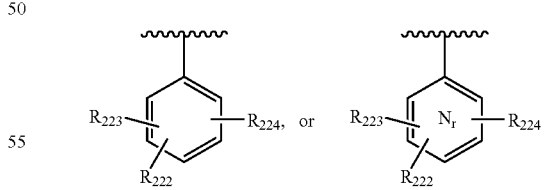

wherein $R_{222}$, $R_{223}$ and $R_{223}$ are independently selected from hydrogen, an alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkyithiocarbamate, substituted alkyithiocarbamate, aryithiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

and r is 1, 2 or 3.

16. The compound of claim 1 wherein $R_{200}$ is a heteroaryl, or substituted aryl having the structure

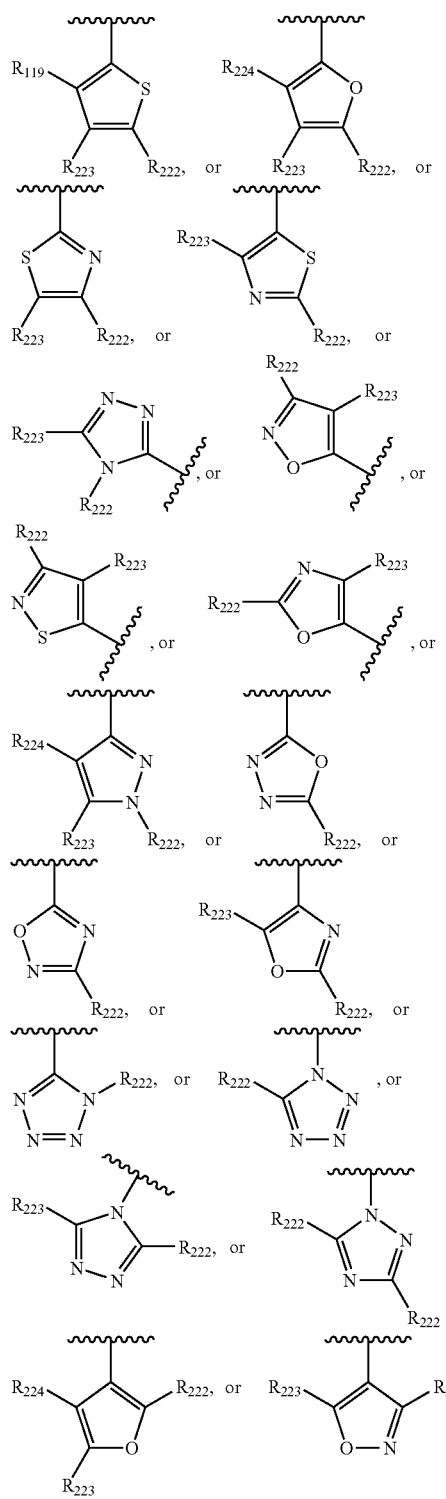

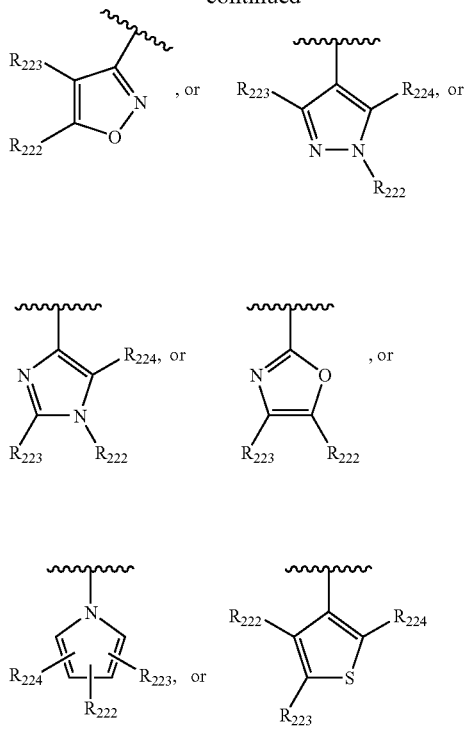

wherein $R_{222}$, $R_{223}$ and $R_{224}$ are independently selected from hydrogen, an alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkyithiocarbamate, substituted alkyithiocarbamate, aryithiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide.

17. The compound of claim 1 wherein $R_{200}$ is a heteroaryl, or substituted aryl having the structure

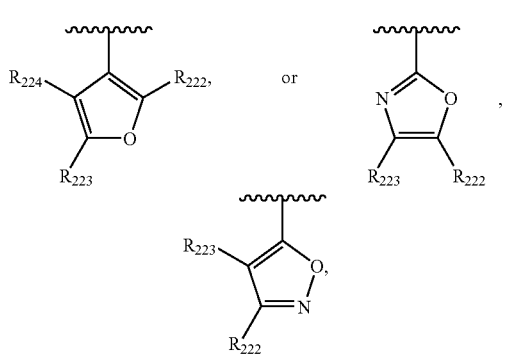

wherein $R_{222}$, $R_{223}$ and $R_{224}$ are independently selected from hydrogen or an alkyl comprising 1 to 4 carbon atoms.

18. The compound of claim 1 wherein $R_{200}$ has the structure

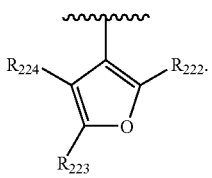

19. The compound of claim 1 wherein $Ar_{10}$ comprises from 3 to 6 ring carbon atoms and optionally 1 to 3 ring heteroatoms selected from O, S, or N.

20. The compound of claim 1 wherein $Ar_{10}$ comprises a benzene or pyridine ring.

21. The compound of claim 1 wherein $Ar_{10}$ has the structure

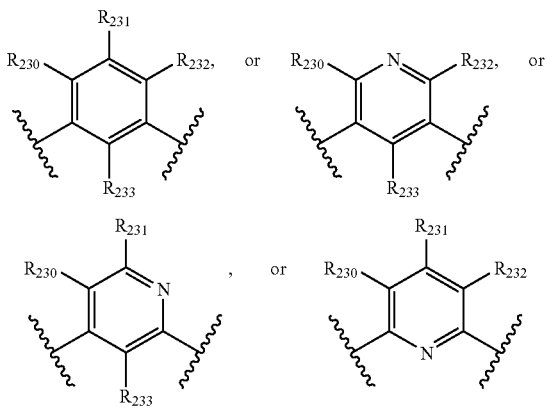

wherein $R_{230}$, $R_{231}$, $R_{232}$ and $R_{233}$ are independently selected from hydrogen, alkyl, haloalkyl, halogen, cyano, nitro, hydroxyl, acyloxy, amino, mono-substituted amino, di-substituted amino, alkylsulfonamide, arylsulfonamide, heteroarylsulfonamide, alkylurea, alkylthiourea, arylurea, acyl, alkylcarbamate, arylcarbamate, alkylthiocarbamate, substituted alkylthiocarbamate, arylthiocarbamate, alkoxy, haloalkoxy, thioalkyl, alkylsulfoxide, alkylsulfonyl, carboxy, carboalkoxy, alkylcarboxamide, or dialkylcarboxamide.

22. The compound of claim 21 wherein $R_{230}$ is not hydrogen.

23. The compound of claim 1 wherein $Ar_{10}$ has the structure

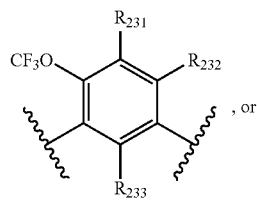

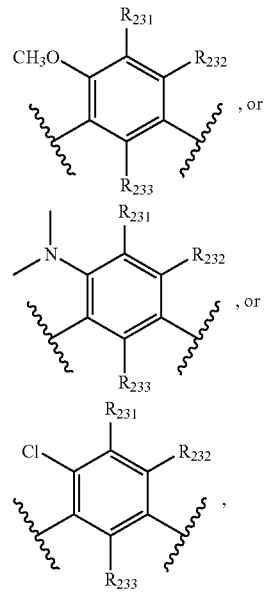

wherein $R_{231}$, $R_{232}$ and $R_{233}$ are independently selected from hydrogen or a halogen.

24. The compound of claim 1 wherein $R_{211}$ is hydrogen or an alkyl having from 1 to 4 carbon atoms.

25. The compound of claim 1 wherein $R_{211}$ is hydrogen.

26. The compound of claim 1 wherein - - - is present.

27. The compound of claim 1 wherein HAr has the structure

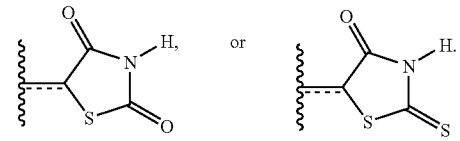

28. The compound of claim 27 wherein - - - is present.

29. The compound of claim 27 wherein - - - is absent.

30. The compound of claim 1 wherein HAr has the structure

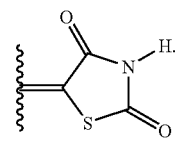

31. The compound of claim 4 wherein HAr has the structure

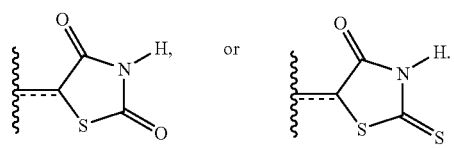

32. The compound of claim 31 wherein $Ar_{10}$ has the structure

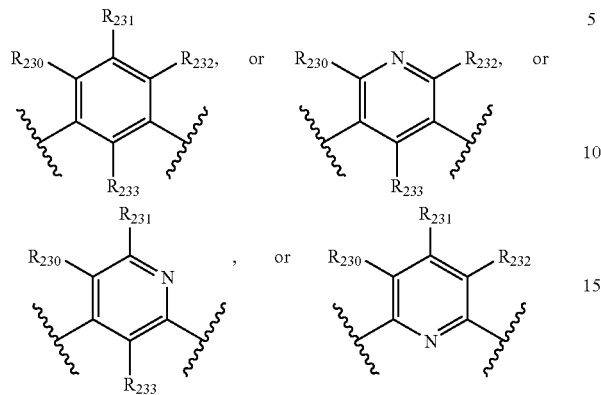

wherein $R_{230}$, $R_{231}$, $R_{232}$ and $R_{233}$ are independently selected from hydrogen, halogen, hydroxyl, amino, or a radical comprising 1 to 4 carbon atoms selected from alkyl, haloalkyl, acyloxy, mono-substituted amino, di-substituted amino, acyl, alkoxy, haloalkoxy, thioalkyl, alkylsulfoxide, alkylsulfonyl, carboxy, carboalkoxy, alkylcarboxamide, or dialkylcarboxamide; with the proviso that $R_{230}$ is not hydrogen.

33. The compound of claim 32 wherein $R_{211}$ is hydrogen and wherein - - - is present.

34. A compound of claim 1 that is effective, when applied at a concentration of about 1 μM for a period of about 7 days, to induce differentiation of mouse preadipocyte 3T3-L1 cells.

35. A compound of claim 1 that is effective, when orally administered to KKA$^y$ mice at a concentration of about 15 mg/kg for a period of about 7 days to decrease the serum glucose levels of the KKA$^y$ mice by at least about 10%.

36. A compound of claim 1 that is effective, when orally administered to KKA$^y$ mice at a concentration of about 15 mg/kg for a period of about 7 days to decrease the serum triglyceride levels of the KKA$^y$ mice by at least about 10%.

37. A pharmaceutical composition comprising one or more pharmaceutically acceptable carriers, and one or more compounds of claim 1 in an amount effective for treating diabetes or obesity, or modulating lipid metabolism, carbohydrate metabolism, lipid and carbohydrate metabolism in a mammal.

38. A method of making the compound of claim 1 comprising
   a) coupling
      i) a bicyclic heterocycle precursor compound having the structure

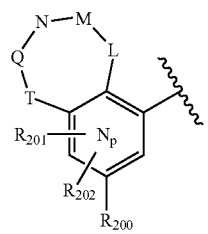

ii) with an $Ar_{10}$ precursor compound having the structure

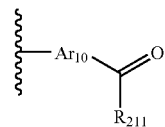

iii) to form a carbonyl containing precursor compound having the formula

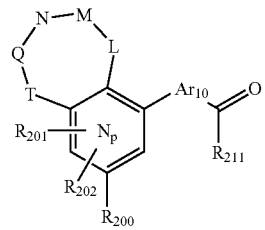

b) further reacting the carbonyl containing precursor compound so as to connect to the carbonyl of the carbonyl containing precursor the HAr heterocycle.

39. The method of claim 38 wherein the further reacting comprises condensing the carbonyl containing precursor compound with a compound having the formula

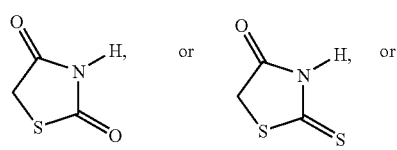

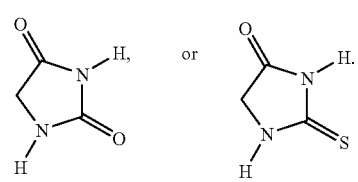

40. A compound having the structure

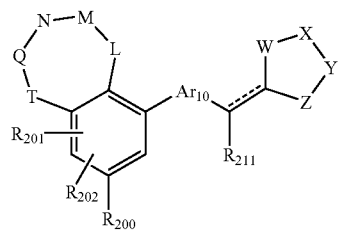

wherein:
a) the bicyclic radical

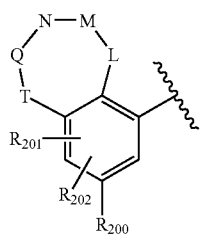

has the structure

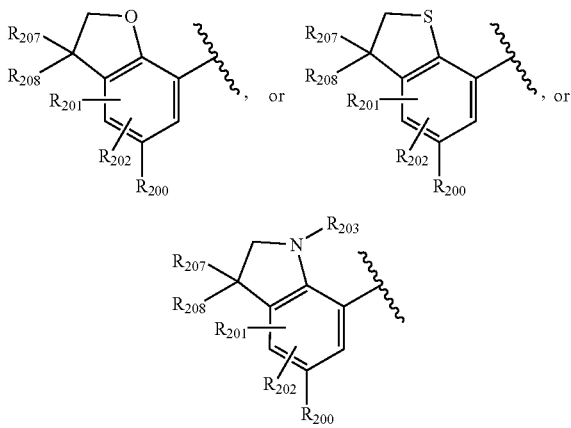

wherein $R_{200}$ comprises 1 to 8 carbon atoms and is selected from the group consisting of an alkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide;

$R_{201}$ and $R_{202}$ are independently selected from hydrogen or a halogen; and $R_{203}$, $R_{207}$ and $R_{208}$ are independently selected from hydrogen or an alkyl comprising 1 to 4 carbon atoms;

b) W, X, Y and Z form a heterocycle having the structure

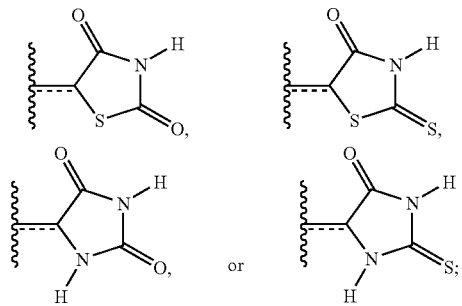

c) - - - is either present or absent;

d) $Ar_{10}$ has the structure

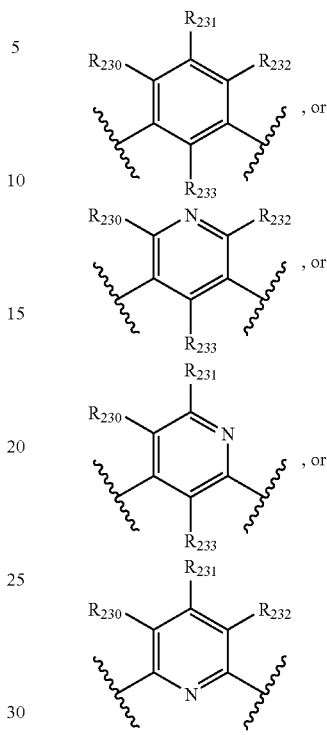

wherein $R_{230}$, $R_{231}$, $R_{232}$ and $R_{233}$ are independently selected from hydrogen, alkyl, haloalkyl, halogen, hydroxyl, acyloxy, amino, mono-substituted amino, di-substituted amino, acyl, alkoxy, haloalkoxy, thioalkyl, alkylsulfoxide, alkylsulfonyl, carboxy, carboalkoxy, alkylcarboxamide, or dialkylcarboxamide, with the proviso that $R_{230}$ is not hydrogen; and e) $R_{211}$ is hydrogen or an alkyl having from 1 to 4 carbon atoms;

or a pharmaceutically acceptable salt thereof.

41. A compound having the structure

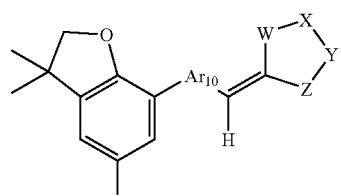

wherein:
a) $R_{200}$ comprises 1 to 4 carbon atoms and is selected from the group consisting of an alkyl, haloalkyl, halogen, cyano, nitro, hydroxyl, acyloxy, amino, mono-alkyl-amino, dialkyl-amino, alkylsulfonamide, arylsulfonamide, heteroarylsulfonamide, acyl, alkylcarbamate, arylcarbamate, alkylthiocarbamate, aryl, heteroaryl, alkoxy, haloalkoxy, thioalkyl, alkylsulfoxide, alkylsulfonyl, thiohaloalkyl, carboxy, carboalkoxy, alkylcarboxamide, or dialkylcarboxamide;

b) W, X, Y and Z form a heterocycle having the structure

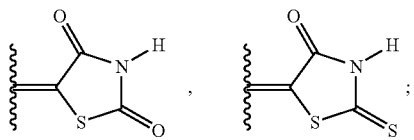

c) $Ar_{10}$ has the structure

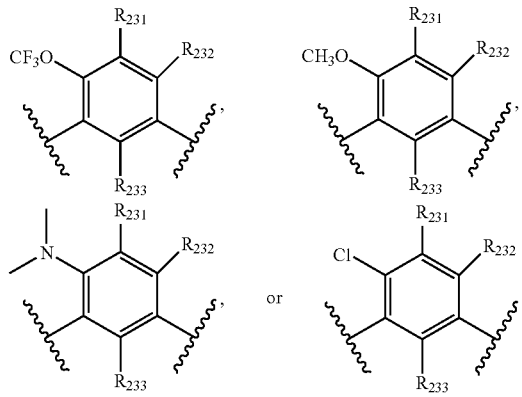

wherein $R_{231}$, $R_{232}$ and $R_{233}$ are independently selected from hydrogen or a halogen.

42. A compound of Formula (300):

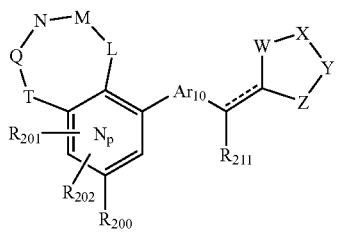

wherein:
a) $R_{200}$, $R_{201}$ and $R_{202}$ are independently selected from hydrogen, hydroxyl, a halogen, amino, or an organic residue comprising 1 to 12 carbon atoms;
b) $N_p$ are the number of heteroaryl ring nitrogens selected from 0, 1 or 2;
c) L, M, N, Q and T residues are independently selected from —C(O)—, —C(S)—, —O—, —S—, —N($R_{203}$)—, —N($R_{204}$)—, —C($R_{205}$)($R_{206}$)—, —C($R_{207}$)($R_{208}$)—, or —C($R_{209}$)($R_{210}$)— residues, and from zero to two of the L, M, N, Q or T residues can be absent;
wherein
  i) $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic residue comprising 1 to 12 carbon atoms; or two of the $R_{203}$, $R_{204}$, $R_{205}$, $R_{206}$, $R_{207}$, $R_{208}$, $R_{209}$ and $R_{210}$ residues can be connected together to form an exocyclic substituent residue comprising 1 to 6 ring carbon atoms and from 0 to 3 optional ring heteroatoms selected from O, S, or N; and (ii) L, M, N, Q and T do not form an amide residue;
d) $Ar_{10}$ is an aryl, substituted aryl, heteroaryl, or substituted heteroaryl residue comprising from 3 to 6 ring carbon atoms and from 0 to 3 optional ring heteroatoms selected from O, S, or N;
e) $R_{211}$ is hydrogen, hydroxy, or an organic residue comprising 1 to 10 carbon atoms;
f) - - - is either present or absent;
g) W, X, Y and Z form a 2,4-thiazolidinedione, 2-thioxo-thiazolidine-4-one, 2,4-imidazolidinedione or 2-thioxo-imidazolidine-4-one residue;

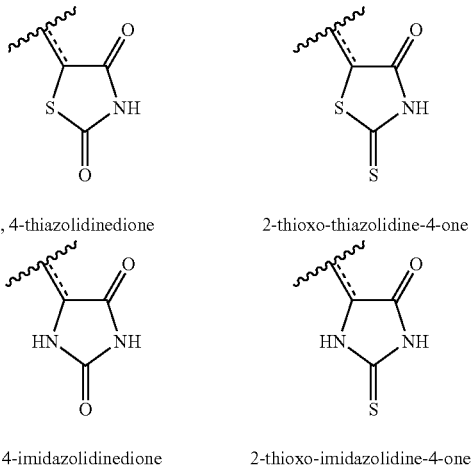

2,4-thiazolidinedione 2-thioxo-thiazolidine-4-one 2,4-imidazolidinedione 2-thioxo-imidazolidine-4-one or a pharmaceutically acceptable salt thereof.

43. A compound having the formula:
  5-[3-(5-Isobutyl-3,3-dimethyl-2,3-dihydro-benzofuran-7-yl)-4-trifluoromethoxy-benzylidene]-thiazolidine-2,4-dione;
  5-[2,5-Difluoro-3-(5-isobutyl-3,3-dimethyl-2,3-dihydro-benzofuran-7-yl)-4-methoxy-benzylidene]-thiazolidine-2,4-dione; or
  5-[3-(5-Furan-3-yl-3,3-dimethyl-2,3-dihydro-benzofuran-7-yl)4-trifluoromethoxy-benzylidene]-thiazolidine-2,4-dione, or a pharmaceutically acceptable salt thereof.

44. A compound having the formula:
  5-[3-(5-Isobutyryl-3,3-dimethyl-2,3-dihydro-benzofuran-7-yl)-4-trifluoromethoxy-benzylidene]-thiazolidine-2, 4-dione,
  7-[5-(2,4-Dioxo-thiazolidin-5-ylidenemethyl)-2-trlfluoromethoy-phenyl]-3,3-dimethyl-2,3-dihydro-benzofuran-5-carboxylic acid methylamide,
  7-[5-(2,4-Dioxo-thiazolidin-5-ylidenemethyl)-2-trifluoromethoxy-phenyl]-3,3-dimethyl-2,3-dihydro-benzofuran-5-carboxylic acid dimethylamide,
  5-[3-(3,3-Dimethyl-5-propionyl-2,3-dihydro-benzofuran-7-yl)-4-trifluoromethoxy-benzylidene]-thiazolidine-2, 4-dione,
  5-[4-Dimethylamino-3-(5-isobutyl-3,3-dimethyl-2,3-dihydro-benzofiiran-7-yl)-benzylidene]-thiazolidine-2,4-dione,
  7-[5-(2,4-Dioxo-thiazolidin-5-ylidenemethyl)-2-trifluoromethoxy-phenyl]-3,3-dimethyl-2,3-dihydro-benzofuran-5-carboxylic acid methyl ester,
  2-[3,3-Dimethyl-7-(2-trifluoromethoxy-5-vinyl-phenyl)-2,3-dihydro-benzofuran-5-ylmethoxy]-ethanol, 5-[3-(5-Methoxymethyl-3,3-dimethyl-2,3-dihydro-benzofuran-7-yl)-4-trifluoromethoxy-benzylidene]-thiazolidine-2,4-dione, 7-[5-(2,4-Dioxo-thiazolidin-5-ylidenemethyl)-2-trifluoromethoxy-phenyl]-3,3-dimethyl-2,3-dihydro-benzofuran-5-carboxylic acid, 5-[3-(5-Dimethylaminomethyl-3,3-dimethyl-2,3-dihydro-benzofuran-7-yl)-4-trifluoromethoxy-benzylidene]-thiazolidine-2,4-dione, 7-[5-(2,4Dioxo-thiazolidin-5-ylidenemethyl)-2-trifluoromethoxy-phenyl]-3,3-dimethyl-2,3-dihydro-benzofuran-5-sulfonic acid methylamide, 5-[3-(5-Methanesulfonyl-3,3-dimethyl-2,3-dihydro-benzofuran-7-yl)-4-trifluoromethoxy-benzylidene]-thiazolidine-2,4-dione, 5-[3-(5-Acetyl-3,3-dimethyl-2,3-dihydro-benzofurafl-7-yl)-4-trifluoromethoxy-benzylidene]-thiazolidine-2,4-dione, 5-[3-(5-Isoxazol-5-yl-3,3-dimethyl-2,3-dihydro-benzofuran-7-yl)-4-trifluoromethoxy-benzylidene]-thiazolidine-2,4-dione, 5-[3-(6-isobutyl-benzo[1,3]dioxol-4-yl)-4-trifluoromethoxy-benzylidene]-thiazolidine-2,4-dione, or 5-[3-(3,3-Dimethyl-5-oxazol-2-yl-2,3-dihydro-benzofuran-7-yl)-4-trifluoromethoxy-benzylidene]-thiazolidine-2,4-dione;

or a pharmaceutically acceptable salt thereof.

45. The compound of claim 42 wherein p is 0.

46. The compound of claim 45 wherein $R_{200}$ is a $C_1$–$C_8$ straight or branched alkyl and $R_{201}$ and $R_{202}$ are hydrogen.

47. The compound of claim 46 wherein $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic residue comprising 1 to 4 carbon atoms.

48. The compound of claim 42 wherein the radical

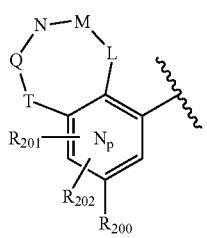

has the structure

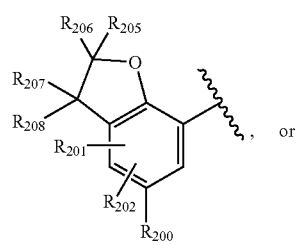

49. The compound of claim 48 wherein $R_{200}$ is a C1–C8 straight or branched alkyl and $R_{201}$ and $R_{202}$ are hydrogen; and $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic radical comprising 1 to 4 carbon atoms.

50. The compound of claim 42 wherein the radical

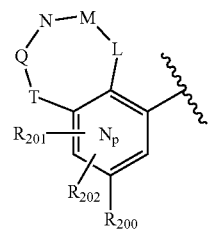

has the structure

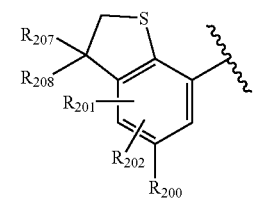

wherein:
$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, ailcyithiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{207}$ and $R_{208}$ are an alkyl or substituted alkyl comprising from 1 to 4 carbon atoms.

51. The compound of claim 42 wherein the radical

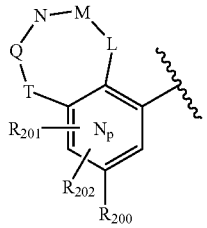

has the structure

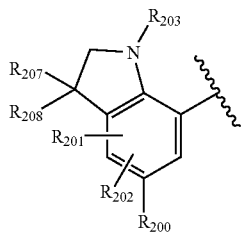

wherein:

$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkyithiocarbamate, substituted alkyithiocarbamate, aryithiocarbamate, heteroaryl, substituted heteroaryl, alkoxy, substituted alkoxy, haloalkoxy, thioalkyl, alkylsulfoxide, alkylsulfonyl, thiohaloallcyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{203}$, $R_{207}$, and $R_{208}$ are an alkyl or substituted alkyl comprising from 1 to 4 carbon atoms.

52. The compound of claim 42 wherein the radical

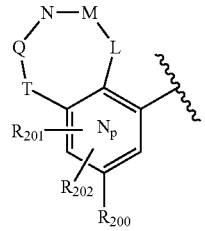

has the structure

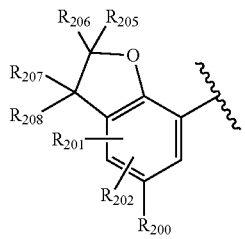

wherein $R_{200}$ is an organic radical comprising 1 to 8 carbon atoms selected from an alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide radical; and $R_{201}$ and $R_{202}$ are hydrogen; and $R_{203}$, $R_{204}$, $R_{205}$, $R_{206}$, $R_{207}$, $R_{208}$, $R_{209}$, and $R_{210}$ are independently selected from hydrogen, hydroxyl, a halogen, amino, or an organic radical comprising 1 to 4 carbon atoms.

53. The compound of claim 42 wherein the radical

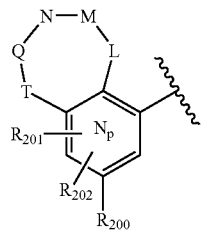

has the structure

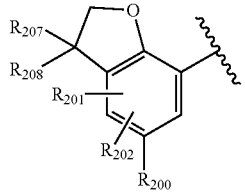

wherein:

$R_{200}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide;

$R_{201}$ and $R_{202}$ are hydrogen or halogen; and $R_{207}$ and $R_{208}$ are an alkyl or substituted alkyl comprising from 1 to 4 carbon atoms.

54. The compound of claim 42 wherein $Ar_{10}$ has the structure

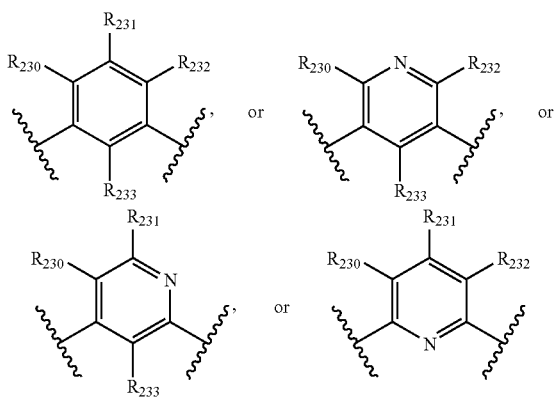

wherein $R_{230}$, $R_{231}$, $R_{232}$ and $R_{233}$ are independently selected from hydrogen, alkyl, haloalkyl, halogen, cyano, nitro, hydroxyl, acyloxy, amino, mono-substituted amino, di-substituted amino, alkylsulfonamide, arylsulfonamide, heteroarylsulfonamide, alkylurea, alkylthiourea, arylurea, acyl, alkylcarbamate, arylcarbamate, alkylthiocarbamate, substituted alkylthiocarbamate, arylthiocarbamate, alkoxy, haloalkoxy, thioalkyl, alkylsulfoxide, alkylsulfonyl, carboxy, carboalkoxy, alkylcarboxamide, or dialkylcarboxamide.

55. The compound of claim 54 wherein $R_{230}$ is not hydrogen.

56. The compound of claim 42 wherein $Ar_{10}$ has the structure

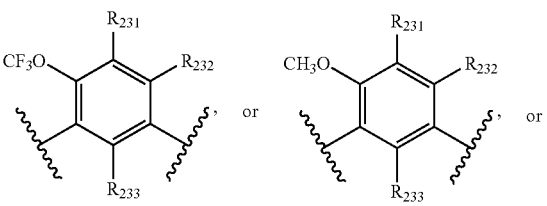

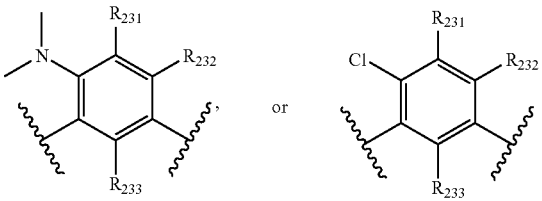

wherein $R_{231}$, $R_{232}$ and $R_{233}$ are independently selected from hydrogen or a halogen.

57. The compound of claim 53 wherein $Ar_{10}$ has the structure

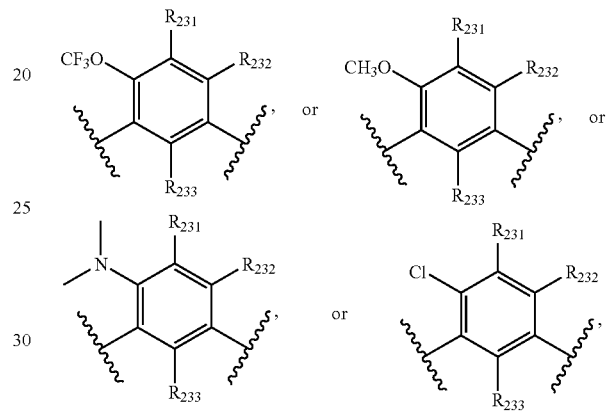

wherein $R_{231}$, $R_{232}$ and $R_{233}$ are independently selected from hydrogen or a halogen.

58. The compound of claim 57 wherein $R_{211}$ is hydrogen.
59. The compound of claim 58 wherein - - - is present.
60. The compound of claim 59 wherein the heterocycle comprising W, X, Y and Z has the structure

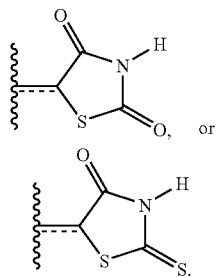

61. A pharmaceutical composition comprising one or more pharmaceutically acceptable carriers, and one or more compounds of claim 42 in an amount effective for treating diabetes, or modulating lipid metabolism or carbohydrate metabolism in a mammal.

* * * * *